US012799179B2

(12) United States Patent
Miyakawa et al.

(10) Patent No.: US 12,799,179 B2
(45) Date of Patent: Nov. 17, 2026

(54) INTERLEUKIN-2 MUTEINS AND USES THEREOF

(71) Applicant: TAKEDA PHARMACEUTICAL COMPANY LIMITED, Osaka (JP)

(72) Inventors: Shuichi Miyakawa, Kanagawa (JP); Dnyaneshwar Eknath Warude, Kanagawa (JP); Ertan Eryilmaz, Cambridge, MA (US)

(73) Assignee: Takeda Pharmaceutical Company Limited, Osaka (JP)

(*) Notice: Subject to any disclaimer, the term of this patent is extended or adjusted under 35 U.S.C. 154(b) by 706 days.

(21) Appl. No.: 18/022,669

(22) PCT Filed: Aug. 31, 2021

(86) PCT No.: PCT/JP2021/032566
§ 371 (c)(1),
(2) Date: Feb. 22, 2023

(87) PCT Pub. No.: WO2022/050401
PCT Pub. Date: Mar. 10, 2022

(65) Prior Publication Data

US 2023/0340054 A1 Oct. 26, 2023

Related U.S. Application Data

(60) Provisional application No. 63/231,471, filed on Aug. 10, 2021, provisional application No. 63/073,208, filed on Sep. 1, 2020.

(51) Int. Cl.

| | |
|---|---|
| ***C07K 14/55*** | (2006.01) |
| ***A61K 38/00*** | (2006.01) |
| ***A61P 37/00*** | (2006.01) |

(52) U.S. Cl.
CPC .............. *C07K 14/55* (2013.01); *A61P 37/00* (2018.01); *A61K 38/00* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 2004/0175357 A1 | 9/2004 | Shanafelt et al. | |
| 2006/0160187 A1 | 7/2006 | Denis-Mize et al. | |
| 2006/0269515 A1 | 11/2006 | Denis-Mize et al. | |
| 2008/0254026 A1* | 10/2008 | Long ......................... | A61P 3/10 435/375 |
| 2019/0062395 A1 | 2/2019 | Merchant et al. | |

FOREIGN PATENT DOCUMENTS

| | | |
|---|---|---|
| CA | 3098930 A1 | 3/2020 |
| CA | 3112989 A1 | 4/2020 |

(Continued)

OTHER PUBLICATIONS

Norris, et al. Type 1 diabetes—early life origins and changing epidemiology. Lancet Diabetes Endocrinology (Mar. 2020), 8:3, p. 1-27.*

(Continued)

*Primary Examiner* — Joanne Hama
*Assistant Examiner* — Jami Michelle Gurley
(74) *Attorney, Agent, or Firm* — Foley & Lardner LLP

(57) ABSTRACT

The present invention provides, among other things, compositions and methods for prophylaxis and treatment of autoimmune disease. The present invention is based, in part, on the surprising discovery that a human interleukin-2 mutein activates proliferation of regulatory T cells. In one aspect, the present invention provides compositions and methods for proliferation of regulatory T cells. In another aspect, a human interleukin-2 (IL-2) mutein comprising an amino acid sequence that is at least 90% identical to the wild type IL-2 protein is described, wherein the IL-2 mutein has (Continued)

WT IL-2

K77A mutant IL-2
-Similar binding as WT at least one amino acid substitution selected from a group consisting of T111H, T37Y, E15T, M23L, P34F, E68F and E62A.

20 Claims, 46 Drawing Sheets
(45 of 46 Drawing Sheet(s) Filed in Color)

Specification includes a Sequence Listing.

(56) References Cited

FOREIGN PATENT DOCUMENTS

| | | | | | |
|---|---|---|---|---|---|
| JP | 2020-524174 | A | | 8/2020 | |
| TW | 1906467 | B | * | 12/2025 | ......... C07K 14/7155 |
| WO | 2005/086798 | A2 | | 9/2005 | |
| WO | WO-2005/086751 | A2 | | 9/2005 | |
| WO | WO-2010/085495 | A1 | | 7/2010 | |
| WO | WO-2015/118016 | A1 | | 8/2015 | |
| WO | WO-2016/164937 | A2 | | 10/2016 | |
| WO | WO-2017/044464 | A1 | | 3/2017 | |
| WO | WO-2017/127514 | A1 | | 7/2017 | |
| WO | WO-2019/028425 | A1 | | 2/2019 | |
| WO | WO-2019173832 | A2 | * | 9/2019 | ......... A61K 47/6851 |
| WO | WO-2020057646 | A1 | * | 3/2020 | ............. A61K 47/68 |
| WO | WO-2020069398 | A1 | * | 4/2020 | ............. C07K 14/55 |
| WO | WO-2020131547 | A1 | * | 6/2020 | ........... A61K 40/428 |
| WO | WO-2020201095 | A1 | * | 10/2020 | ......... A61K 38/2013 |
| WO | WO-2020252418 | A2 | * | 12/2020 | .............. A61P 35/00 |
| WO | WO-2021/119534 | A2 | | 6/2021 | |

OTHER PUBLICATIONS

Barnes and Gray. Bioinformatics for geneticists. John Wiley & Sons Ltd, The Atrium, Southern Gate, Chichester, West Sussex PO19 8SQ, England. 2003, p. 1-411.*

Chinen et al. An essential role for IL-2 receptor in regulatory T cell function. Nature Immunology (2016), 17: 11, p. 1322-1333.*

Gasteiger et al. Foxp3+ regulatory T-cells and IL-2: the Moirai of T-cell fates? Frontiers in Immunology (2012), 3:179, p. 1-4.*

Carmenate et al., "Human IL-2 Mutein with Higher Antitumor Efficacy Than Wild Type IL-2", The Journal of Immunology, vol. 190, No. 12, Jun. 15, 2013, pp. 6230-6238, DOI: 10.4049/jimmunol.1201895, (10 pages).

International Search Report and Written Opinion for PCT/US2021/032566 dated Nov. 29, 2022 (36 pages).

Lin et al., "The role of Stat5a and Stat5b in signaling by IL-2 family cytokines", Oncogene, vol. 19, No. 21, 2000, pp. 2566-2576, DOI: 10.1038/sj.onc.1203523, (11 pages).

Peterson et al., "A long-lived IL-2 mutein that selectively activates and expands regulatory T cells as a therapy for autoimmune disease", Journal of Autoimmunity, vol. 95, Nov. 13, 2018, pp. 1-14, DOI: 10.1016/j.jaut.2018.10.017, (14 pages).

Rojas et al., "Molecular dissection of the interactions of an antitumor interleukin-2-derived mutein on a phage display-based platform", Journal of Molecular Recognition, vol. 28, No. 4, 2015, pp. 261-268, DOI: 10.1002/jmr.2440, (8 pages).

Ye et al., "Targeting IL-2: an unexpected effect in treating immunological diseases", Signal Transduction and Targeted Therapy, vol. 3, Article No. 2, 2018, DOI: 10.1038/s41392-017-0002-5, (10 pages).

Khan, "Gene Expression in Mammalian Cells and its Applications", Advanced Pharmaceutical Bulletin, 2013, vol. 3(2), DOI: http://dx.doi.org/10.5681/apb.2013.042 http://apb.tbzmed.ac.ir/ pp. 257-263 (7 pages).

Muller, et al., "Spliceosomal Peptide P140 for Immunotherapy of Systemic Lupus Erythematosus: results of an Early Phase II Clinical Trial", Arthritis & Rheumatism: Official Journal of the American College of Rheumatology, Dec. 2008, vol. 58, 12 pp. 3873-3883 (11 pages).

Viola, et al., "Non-viral Nanovectors for Gene Delivery: Factors that Govern Successful Therapeutics", Expert Opinion Drug Deliv., 2010, v. 7(6), pp. 721-735 (15 pages).

* cited by examiner

WT IL-2

K77A mutant IL-2
-Similar binding as WT

E96A mutant IL-2

| Clone | EC50 (pM) | Emax (fold) |
|---|---|---|
| WT | 4.9 | 2 |
| M23L | 0.7 | 2.5 |
| T111H | 0.8 | 2.5 |
| E68F | 12.3 | 2.6 |

| Clone | EC50 (pM) | Emax (fold) |
|---|---|---|
| WT | 6.8 | 2.5 |
| E15T | 1.4 | 2.7 |
| P34F | 14.3 | 2.8 |
| T37Y | 8.2 | 2.4 |

Blood Data-96hr

Lymph Node Data-96hr

Spleen Data-96hr

Tumor Data-96hr

Cell number change in T111H treated monkey

SEQUENCE LISTING

<160> NUMBER OF SEQ ID NOS: 12

<210> SEQ ID NO 1
<211> LENGTH: 133
<212> TYPE: PRT
<213> ORGANISM: Homo sapiens

<400> SEQUENCE: 1

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130
```

<210> SEQ ID NO 2
<211> LENGTH: 133
<212> TYPE: PRT
<213> ORGANISM: Homo sapiens

<400> SEQUENCE: 2

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu His Ala
            100                 105                 110

Thr Ile Val Glu Phe Leu Asn Arg Trp Ile Thr Phe Ala Gln Ser Ile
        115                 120                 125

Ile Ser Thr Leu Thr
    130
```

<210> SEQ ID NO 3
<211> LENGTH: 133
<212> TYPE: PRT
<213> ORGANISM: Homo sapiens

<400> SEQUENCE: 3

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Tyr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
    130


<210> SEQ ID NO 4
<211> LENGTH: 133
<212> TYPE: PRT
<213> ORGANISM: Homo sapiens

<400> SEQUENCE: 4

Ala Pro Thr Ser Ser Ser Thr Lys Lys Thr Gln Leu Gln Leu Thr His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
    130


<210> SEQ ID NO 5
<211> LENGTH: 133
<212> TYPE: PRT
<213> ORGANISM: Homo sapiens

<400> SEQUENCE: 5

Ala Pro Thr Ser Ser Ser Thr Lys Lys Thr Gln Leu Gln Leu Glu His
1               5                   10                  15

Leu Leu Leu Asp Leu Gln Leu Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45
```

```
Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
    130


<210> SEQ ID NO 6
<211> LENGTH: 133
<212> TYPE: PRT
<213> ORGANISM: Homo sapiens

<400> SEQUENCE: 6

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Phe Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
    130


<210> SEQ ID NO 7
<211> LENGTH: 133
<212> TYPE: PRT
<213> ORGANISM: Homo sapiens

<400> SEQUENCE: 7

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Phe Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95
```

```
Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
    130


<210> SEQ ID NO 8
<211> LENGTH: 133
<212> TYPE: PRT
<213> ORGANISM: Homo sapiens

<400> SEQUENCE: 8

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Ala Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130


<210> SEQ ID NO 9
<211> LENGTH: 227
<212> TYPE: PRT
<213> ORGANISM: Homo sapiens

<400> SEQUENCE: 9

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140
```

```
Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 10
<211> LENGTH: 227
<212> TYPE: PRT
<213> ORGANISM: Homo sapiens

<400> SEQUENCE: 10

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 11
<211> LENGTH: 227
<212> TYPE: PRT
<213> ORGANISM: Homo sapiens

<400> SEQUENCE: 11
```

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu Lys Phe His Tyr Thr Gln Lys Ser Leu Ser Leu Ser
    210                 215                 220

Pro Gly Lys
225
```

<210> SEQ ID NO 12
<211> LENGTH: 227
<212> TYPE: PRT
<213> ORGANISM: Homo sapiens

<400> SEQUENCE: 12

```
Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
```

-continued

```
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu Lys Phe His Tyr Thr Gln Lys Ser Leu Ser Leu Ser
    210                 215                 220

Pro Gly Lys
225
```

INTERLEUKIN-2 MUTEINS AND USES THEREOF

CROSS-REFERENCE TO RELATED APPLICATIONS

This application is a 35 U.S.C. § 371 National Stage Application of International Application No. PCT/JP2021/032566, filed on Aug. 31, 2021, which claims benefit of, and priority to, U.S. Ser. No. 63/073,208 filed on Sep. 1, 2020 and U.S. Ser. No. 63/231,471 filed on Aug. 10, 2021 the entire contents of which are incorporated herein by reference.

INCORPORATION BY REFERENCE OF THE SEQUENCE LISTING

The instant application contains a Sequence Listing which has been filed electronically in ASCII format and is hereby incorporated by reference in its entirety. Said ASCII copy created on Feb. 16, 2023, is named "TKJ-001US1_SL.txt" and is 17,957 bytes in size.

BACKGROUND OF THE INVENTION

Autoimmune diseases result from a failure of the immune system to distinguish between self and non-self-tissue, thereby attacking and destroying cells and tissues of the body.

One of the functions of regulatory T cells (Treg) is to suppress pathological activation of the immune system and prevent autoimmune disease. Regulatory T cells (Treg) are CD4+CD25+ T cells that suppress the activity of other immune cells, and play an important role in maintaining tolerance to self-antigens, modulating responses to foreign antigens and regulation of the immune system. Treg cell numbers or cell function are seen to be reduced in several autoimmune and inflammatory diseases including, for example, Type 1 diabetes (TID), Systemic Lupus Erythematosus (SLE) and Graft vs. Host Disease (GVHD).

Interleukin-2 (IL-2) is a potent stimulator of the immune system activating T cells, B cells and monocytes besides stimulating growth of regulatory T cells (Treg). Therapeutic administration of IL-2 results in undesirable toxicity, for example, due to the non-specific activation of NK cells.

T cells require the expression of CD25 to respond to low concentrations of IL-2 that typically exist in tissues. T cells that express CD25 include both FOXP3+ CD4+ regulatory T cells (Treg cells), which are essential for suppressing autoimmune inflammation. On the other hand, FOXP3− T effector cells activated to express CD25, which may be either CD4+ or CD8+ and contribute to inflammation, autoimmunity, organ graft rejection, or graft-versus-host disease. IL-2-stimulated STAT5 signaling is believed to be important for normal T-reg cell growth and survival and for high FOXP3 expression.

SUMMARY OF INVENTION

There is a need for therapies that selectively stimulate the production and/or activity of Treg cells for immune system regulation. The present invention provides, among other things, compositions and methods for proliferation of regulatory T cells (Tregs). The present invention provides, among other things, human interleukin-2 (IL-2) muteins and IgG Fc fusion proteins thereof that activate proliferation of regulatory T cells. The present invention provides, among other things, compositions and methods for prophylaxis and treatment of autoimmune disease.

One approach for treating autoimmune diseases is the transplantation of autologous, ex vivo expanded Treg cells. Although successful in animal models and early stage human clinical trials, this approach is challenging since it is technically complex and invasive because it requires personalized treatment with the patient's own T-cells.

Recombinant IL-2, Proleukin (Prometheus Laboratories, San Diego) is approved for treatment of metastatic melanoma and metastatic renal cancer, but it is associated with severe side-effects due to high toxicity. Clinical treatment with low dose IL-2 has been used in chronic GVHD and HCV-associated autoimmune vasculitis and demonstrated increased Treg levels. However, even clinical trials of low dose IL-2 resulted in safety and tolerability issues. Therefore, there is a need for a therapeutic agent for preventing and/or treating autoimmune disease that specifically targets and activates Treg cells that is safe and tolerable for treating humans.

IL-2 receptors are broadly expressed on many types of immune cells, including T cells, NK cells, eosinophils, and monocytes, resulting in pleiotropic effects and high systemic toxicity due to IL-2 administration. IL-2 receptors exist in three forms: α (alpha) (also called IL-2Ra, CD25, or Tac antigen), β (beta) (also called IL-2Rb, or Cd122), and γ (gamma).

When administered to human patients, IL-2 has a short half-life of 85 minutes for intravenous administration and 3.3 hours subcutaneous administration (Kirchner, G. I. et al., 1998, Br J. Clin. Pharmacol. 46:5-10). Since in vitro studies showed that at least 5-6 hours of exposure to IL-2 was required to stimulate T cell proliferation, high doses are generally thought to be necessary.

In one aspect, the present invention identifies an improved method of treating autoimmune diseases using IL-2 variants that are selective for Treg cells relative to other types of immune cells.

In one aspect, the IL-2 mutein is fused to the Fc region of IgG to increase the half-life of circulating IL-2.

Although IL-2 targets many types of immune cells, Treg cells respond to lower concentrations of IL-2 than many other cell types because of the expression of high levels of the high affinity receptor IL2Rαβγ, which is composed of IL2Rα (CD25), IL2Rβ (CD122) and IL2Rγ (CD132) receptors. Treg growth is responsive to IL-2. Treg cells (CD4 positive cells) express IL2Rα (known also as CD25), while other non-Treg T cells that are CD8 positive express IL2Rβ (CD122).

The present invention is based, in part, on the surprising discovery that exemplary IL-2 muteins preferentially expand or stimulate Treg cells. The present invention provides human interleukin-2 muteins comprising at least one amino acid substitution selected from a group consisting of T111H, T37Y, E15T, M23, P34F, E68F and E62A in relation to wild type IL-2 (SEQ ID NO: 1) that can selectively activate proliferation of regulatory T cells.

In one aspect, the present invention provides a human interleukin-2 (IL-2) mutein comprising an amino acid sequence that is at least 90% identical to the amino acid sequence set forth in SEQ ID NO:1, wherein said IL-2 mutein has at least one amino acid substitution selected from a group consisting of T111H, T37Y, E15T, M23L, P34F, E68F and E62A. Accordingly, in some embodiments, the IL-2 mutein has at least one amino acid substitution characterized by a T111H substitution. In some embodiments, the IL-2 mutein has at least one amino acid substitution characterized by a T37Y substitution. In some embodiments, the IL-2 mutein has at least one amino acid substitution characterized by a E15T substitution. In some embodiments, the IL-2 mutein has at least one amino acid substitution characterized by a M23L substitution. In some embodiments, the IL-2 mutein has at least one amino acid substitution characterized by a P34F substitution. In some embodiments, the IL-2 mutein has at least one amino acid substitution characterized by a E68F substitution. In some embodiments, the IL-2 mutein has at least one amino acid substitution characterized by a E62A substitution. In some embodiments, the IL-2 mutein has a combination of amino acid substitutions comprising one or more of the following amino acid substitutions: T111H, T37Y, E15T, M23L, P34F, E68F and E62A.

In some embodiments, the human interleukin-2 (IL-2) mutein further comprises an amino acid substitution of C125A.

In one embodiment, the present invention provides a nucleotide sequence encoding the amino acid sequence of human interleukin-2 (IL-2) mutein.

In some embodiments, the present invention provides a medicament comprising the human interleukin-2 (IL-2) mutein, or a salt thereof. In some embodiments, the IL-2 muteins are fused with an IgG Fc fusion partner.

In some embodiments, the medicament is a Treg activator.

In some embodiments, the medicament is an agent for the prophylaxis or treatment of autoimmune disease.

In some embodiments, the IL-2 mutein may comprise one or more compounds to increase the serum-half-life of the IL-2 mutein when administered to a patient. Such half-life extending molecules include water soluble polymers (e.g., polyethylene glycol (PEG)), low- and high-density lipoproteins, antibody Fc (monomer or dimer), transthyretin (TTR), and TGF-β latency associated peptide (LAP). Also contemplated are IL-2 variants comprising a combination of serum half-life extending molecules, such as PEGylated TTR (from US Pat. Appl. Publ. No. 2003/0195154).

In some embodiments, the present invention provides a method of proliferating regulatory T cells (Treg cells) in a mammal, which comprises administering an effective amount of the human interleukin-2 (IL-2) mutein, or a salt thereof to the mammal.

In some embodiments, the present invention provides a method for the prophylaxis or treatment of autoimmune disease in a mammal, which comprises administering an effective amount of the human interleukin-2 (IL-2) mutein, or a salt thereof to the mammal.

In some embodiments, the present invention provides the human interleukin-2 (IL-2) mutein for use in a method for treating of autoimmune disease. Various autoimmune disease are recognized in the art, and include, for example, diseases associated with augmented inflammatory responses such as inflammatory skin diseases including psoriasis and dermatitis (e.g., atopic dermatitis); responses associated with inflammatory bowel disease (such as Crohn's disease and ulcerative colitis); dermatitis; allergic conditions such as eczema and asthma; rheumatoid arthritis; systemic lupus erythematosus (SLE) (including but not limited to lupus nephritis, cutaneous lupus); diabetes mellitus (e.g., type 1 diabetes mellitus or insulin dependent diabetes mellitus); multiple sclerosis and juvenile onset diabetes.

In some embodiments, the present invention provides use of the human interleukin-2 (IL-2) mutein, or a salt thereof for the production of an agent for the prophylaxis or treatment of autoimmune disease.

In some embodiments, the present invention provides a method of proliferation of regulatory T cells (Tregs), comprising contacting the population of T cells with an effective amount of human interleukin-2 (IL-2) mutein as described herein.

Any aspect or embodiment described herein can be combined with any other aspect or embodiment as disclosed herein. While the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

Other features and advantages of the invention will be apparent from the detailed description, drawings and claims that follow. It should be understood, however, that the detailed description, the drawings, and the claims, while indicating embodiments of the present invention, are given by way of illustration only, not limitation. Various changes and modifications within the scope of the invention will become apparent to those skilled in the art.

BRIEF DESCRIPTION OF DRAWINGS

The patent or application file contains at least one drawing executed in color. Copies of this patent or patent application publication with color drawing(s) will be provided by the Office upon request and payment of the necessary fee.

The following figures are for illustration purposes only and not for limitation.

FIG. 8A-FIG. 8C pertain to a single round of administration of IL-2 mutein or WT IL-2. FIG. 8D-FIG. 8F pertain to two rounds of administration of IL-2 mutein or WT IL-2.

DEFINITIONS

Figure 1A:
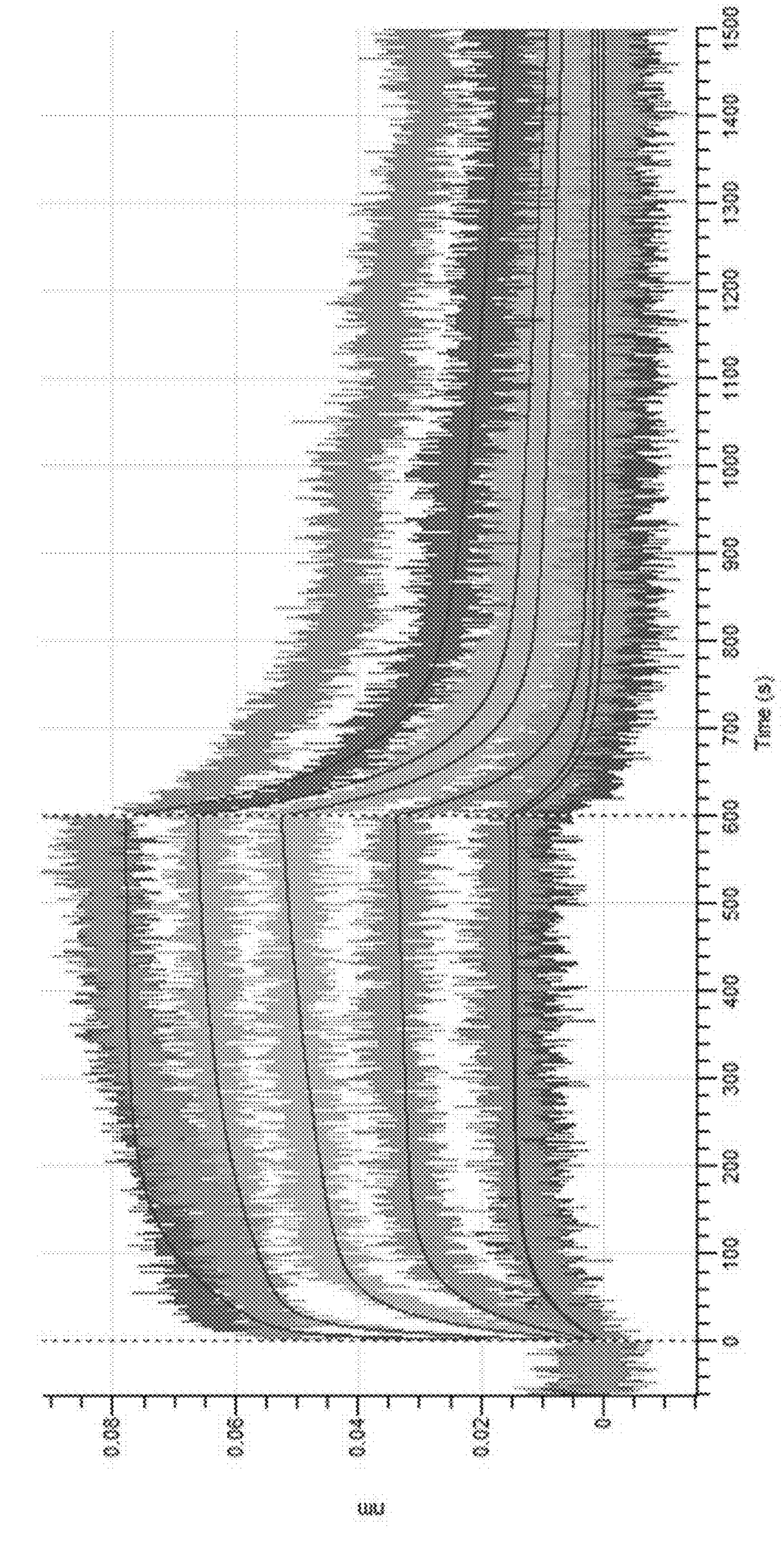
FIG. 1A is a graph showing binding affinity of WT IL-2 to IL-2Rα (CD25) for comparison with two exemplary IL-2 muteins.

In order for the present invention to be more readily understood, certain terms are first defined below. Additional definitions for the following terms and other terms are set forth throughout the Specification.

As used in this Specification and the appended claims, the singular forms “a,” “an” and “the” include plural referents unless the context clearly dictates otherwise.

Unless specifically stated or obvious from context, as used herein, the term “or” is understood to be inclusive and covers both “or” and “and”.

The terms “e.g.,” and “i.e.,” as used herein, are used merely by way of example, without limitation intended, and should not be construed as referring only those items explicitly enumerated in the specification.

The terms “or more”, “at least”, “more than”, and the like, e.g., “at least one” are understood to include but not be limited to at least 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more than the stated value. Also included is any greater number or fraction in between.

Conversely, the term "no more than" includes each value less than the stated value. For example, "no more than 100 nucleotides" includes 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, and 0 nucleotides. Also included is any lesser number or fraction in between.

The terms "plurality", "at least two", "two or more", "at least second", and the like, are understood to include but not limited to at least 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more. Also included is any greater number or fraction in between.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

Unless specifically stated or evident from context, as used herein, the term "about" is understood as within a range of normal tolerance in the art, for example within 2 standard deviations of the mean. "About" can be understood to be within 10%, 9%, 8%, 7%, 6%, 5%, 4%, 3%, 2%, 1%, 0.5%, 0.1%, 0.05%, 0.01%, or 0.001% of the stated value. Unless otherwise clear from the context, all numerical values provided herein reflects normal fluctuations that can be appreciated by a skilled artisan.

Fusion protein, as used herein, generally refers to a fusion polypeptide molecule comprising an immunoglobulin molecule and an IL-2 molecule, wherein the components of the fusion protein are linked to each other by peptide-bonds, either directly or through peptide linkers. For clarity, the individual peptide chains of the immunoglobulin component of the fusion protein may be linked non-covalently, e.g., by disulfide bonds.

Fused refers to components that are linked by peptide bonds, either directly or via one or more peptide linkers.

Specific binding means that the binding is selective for the antigen and can be discriminated from unwanted or non-specific interactions. The ability of an immunoglobulin to bind to a specific antigen can be measured either through an enzyme-linked immunosorbent assay (ELISA) or other techniques familiar to one of skill in the art, e.g., Surface Plasmon Resonance (SPR) technique (analyzed on a BIAcore instrument), and traditional binding assays. In one embodiment, the extent of binding of an immunoglobulin to an unrelated protein is less than about 10% of the binding of the immunoglobulin to the antigen as measured, e.g., by SPR. In certain embodiments, an immunoglobulin that binds to the antigen has a dissociation constant (D) of $<1$ μM, $<100$ nM, $<10$ nM, $<1$ nM, $<0.1$ nM, $<0.01$ nM, or $<0.001$ nM (e.g., $10^{-8}$ M or less, e.g., from $10^{-8}$ M to $10^{-13}$ M, e.g., from $10^{-9}$ M to $10^{-13}$ M).

Affinity or binding affinity refers to the strength of the sum total of non-covalent interactions between a single binding site of a molecule (e.g., an antibody) and its binding partner (e.g., an antigen). Unless indicated otherwise, as used herein, binding affinity refers to intrinsic binding affinity which reflects a 1:1 interaction between members of a binding pair (e.g., antibody and antigen). The affinity of a molecule X for its partner Y can generally be represented by the dissociation constant (KD), which is the ratio of dissociation and association rate constants (koff and kon, respectively). Thus, equivalent affinities may comprise different rate constants, as long as the ratio of the rate constants remains the same. Affinity can be measured by common methods known in the art, including those described herein. A particular method for measuring affinity is Surface Plasmon Resonance (SPR).

Reduced binding, for example reduced binding to an Fc receptor or an IL-2 receptor, refers to a decrease in affinity for the respective interaction, as measured for example by SPR. For clarity the term includes also reduction of the affinity to zero (or below the detection limit of the analytic method), i.e. complete abolishment of the interaction. Conversely, increased binding refers to an increase in binding affinity for the respective interaction.

Fc domain or Fc region herein is used to define a C-terminal region of an immunoglobulin heavy chain that contains at least a portion of the constant region. The term includes native sequence Fc regions and variant Fc regions. An IgG Fc region comprises an IgG CH2 and an IgG CH3 domain. The CH2 domain of a human IgG Fc region usually extends from an amino acid residue at about position 231 to an amino acid residue at about position 340. In one embodiment, a carbohydrate chain is attached to the CH2 domain. The CH2 domain herein may be a native sequence CH2 domain or variant CH2 domain. The "CH3 domain" comprises the stretch of residues C-terminal to a CH2 domain in an Fc region (i.e. from an amino acid residue at about position 341 to an amino acid residue at about position 447 of an IgG). The CH3 region herein may be a native sequence CH3 domain or a variant CH3 domain (e.g., a CH3 domain with an introduced "protuberance" ("knob") in one chain thereof and a corresponding introduced "cavity" ("hole") in the other chain thereof. Such variant CH3 domains may be used to promote heterodimerization of two non-identical immunoglobulin heavy chains as herein described. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, MD, 1991.

Effector functions refers to those biological activities attributable to the Fc region of an immunoglobulin, which vary with the immunoglobulin isotype. Examples of immunoglobulin effector functions include: C1q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g., B cell receptor), and B cell activation.

Activating Fc receptor is an Fc receptor that following engagement by an Fc region of an immunoglobulin elicits signaling events that stimulate the receptor-bearing cell to perform effector functions. Activating Fc receptors include FcγRIIIa (CD 16a), FcγRI (CD64), FcγRIIa (CD32), and FcaRI (CD89). A particular activating Fc receptor is human FcγRIIIa (see UniProt accession no. P08637 (version 141)).

Interleukin-2 or IL-2 as used herein, refers to any native IL-2 from any vertebrate source, including mammals such as primates (e.g., humans) and rodents (e.g., mice and rats), unless otherwise indicated. The term encompasses unprocessed IL-2 as well as any form of IL-2 that results from processing in the cell. The term also encompasses naturally occurring variants of IL-2, e.g., splice variants or allelic variants. The amino acid sequence of an exemplary human IL-2 is shown in SEQ ID NO: 1. Unprocessed human IL-2 additionally comprises an N-terminal 20 amino acid signal peptide, which is absent in the mature IL-2 molecule.

Wild-type IL-2 or native IL-2, also termed wild-type IL-2, is meant a naturally occurring IL-2. The sequence of a native human IL-2 molecule is shown in SEQ ID NO: 1. For the purpose of the present invention, the term wild-type also encompasses forms of IL-2 comprising one or more amino acid mutation that does not alter IL-2 receptor binding compared to the naturally occurring, native IL-2, such as e.g., a substitution of cysteine at a position corresponding to residue 125 of human IL-2 to alanine. In some embodiments wild-type IL-2 for the purpose of the present invention comprises the amino acid substitution C125A (see SEQ ID NO: 3).

CD25 or IL-2 receptor α as used herein, refers to any native CD25 from any vertebrate source, including mammals such as primates (e.g., humans) and rodents (e.g., mice and rats), unless otherwise indicated. The term encompasses "full-length", unprocessed CD25 as well as any form of CD25 that results from processing in the cell. The term also encompasses naturally occurring variants of CD25, e.g., splice variants or allelic variants. In certain embodiments CD25 is human CD25.

High-affinity IL-2 receptor as used herein refers to the heterotrimeric form of the IL-2 receptor, consisting of the receptor γ-subunit (also known as common cytokine receptor γ-subunit, yc, or CD132), the receptor β-subunit (also known as CD122 or p70) and the receptor a-subunit (also known as CD25 or p55). The term intermediate-affinity IL-2 receptor or IL-2 receptor βγ by contrast refers to the IL-2 receptor including only the γ-subunit and the β-subunit, without the α-subunit (for a review see, e.g., Olejniczak and Kasprzak, Med Sci Monit 14, RA179-189 (2008)).

Regulatory T cell or Treg cell refers to a specialized type of CD4+ T cell that can suppress the responses of other T cells (effector T cells). Treg cells are characterized by expression of CD4, the a-subunit of the IL-2 receptor (CD25), and the transcription factor forkhead box P3 (FOXP3) (Sakaguchi, Annu Rev Immunol 22, 531-62 (2004)) and play a critical role in the induction and maintenance of peripheral self-tolerance to antigens, including those expressed by tumors.

CD4+ T cells means CD4+ T cells other than regulatory T cells. Conventional CD4+ memory T cells are characterized by expression of CD4, CD3, but not FOXP3. Conventional CD4+ memory T cells are a subset of conventional CD4+ T cells, further characterized by lack of expression of CD45RA, in contrast to conventional CD4+ naive T cells which do express CD45RA.

By selective activation of Treg cells is meant activation of Treg cells essentially without concomitant activation of other T cell subsets (such as CD4+ T helper cells, CD8+ cytotoxic T cells, NK T cells) or natural killer (NK) cells. Methods for identifying and distinguishing these cell types are described in the Examples. Activation may include induction of IL-2 receptor signaling (as measured e.g., by detection of phosphorylated STAT5a), induction of proliferation (as measured e.g., by detection of Ki-67) and/or up-regulation of expression of activation markers (such as e.g., CD25).

The term peptide linker refers to a peptide comprising one or more amino acids, typically about 2-20 amino acids. Peptide linkers are known in the art or are described herein. Suitable, non-immuno genie linker peptides include, for example, (G4S)n, (SG4)n or G4 (SG4), peptide linkers, "n" is generally a number between 1 and 10, typically between 2 and 4.

The term modification refers to any manipulation of the peptide backbone (e.g., amino acid sequence) or the post-translational modifications (e.g., glycosylation) of a polypeptide.

A knob-into-hole modification refers to a modification within the interface between two immunoglobulin heavy chains in the CH3 domain, wherein i) in the CH3 domain of one heavy chain, an amino acid residue is replaced with an amino acid residue having a larger side chain volume, thereby generating a protuberance ("knob") within the interface in the CH3 domain of one heavy chain which is positionable in a cavity ("hole") within the interface in the CH3 domain of the other heavy chain, and ii) in the CH3 domain of the other heavy chain, an amino acid residue is replaced with an amino acid residue having a smaller side chain volume, thereby generating a cavity ("hole") within the interface in the second CH3 domain within which a protuberance ("knob") within the interface in the first CH3 domain is positionable. In one embodiment, the "knob-into-hole modification" comprises the amino acid substitution T366W and optionally the amino acid substitution S354C in one of the antibody heavy chains, and the amino acid substitutions T366S, L368A, Y407V and optionally Y349C in the other one of the antibody heavy chains. The knob-into-hole technology is described e.g., in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g., tyrosine or tryptophan). Compensatory cavities of identical or similar size to the protuberances are created in the interface of the second polypeptide by replacing large amino acid side chains with smaller ones (e.g., alanine or threonine). Introduction of two cysteine residues at position S354 and Y349, respectively, results in formation of a disulfide bridge between the two antibody heavy chains in the Fc region, further stabilizing the dimer (Carter, J Immunol Methods 248, 7-15 (2001)).

Amino acid substitution refers to the replacement in a polypeptide of one amino acid with another amino acid. In one embodiment, an amino acid is replaced with another amino acid having similar structural and/or chemical properties, e.g., conservative amino acid replacements.

Conservative amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. Non-conservative substitutions will entail exchanging a member of one of these classes for another class. For example, amino acid substitutions can also result in replacing one amino acid with another amino acid having different structural and/or chemical properties, for example, replacing an amino acid from one group (e.g., polar) with another amino acid from a different group (e.g., basic). Amino acid substitutions can be generated using genetic or chemical methods well known in the art. Genetic methods may include site-directed mutagenesis, PCR, gene synthesis and the like. It is contemplated that methods of altering the side chain group of an amino acid by methods other than genetic engineering, such as chemical modification, may also be useful. Various designations may be used herein to indicate the same amino acid substitution. For example, a substitution from proline at position 329 of the immunoglobulin heavy chain to glycine can be indicated as 329G, G329, G329, P329G, or Pro329Gly.

Percent (%) amino acid sequence identity with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN® (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction XIY, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program. "Polynucleotide" or "nucleic acid" as used interchangeably herein, refers to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. A sequence of nucleotides may be interrupted by non-nucleotide components. A polynucleotide may comprise modification(s) made after synthesis, such as conjugation to a label.

By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These alterations of the reference sequence may occur at the 5' or 3' terminal positions of the reference nucleotide sequence or anywhere between those terminal positions, interspersed either individually among residues in the reference sequence or in one or more contiguous groups within the reference sequence. As a practical matter, whether any particular polynucleotide sequence is at least 80%, 85%, 90%, 95%, 96%, 97%, 98% or 99% identical to a nucleotide sequence of the present invention can be determined conventionally using known computer programs, such as the ones discussed above for polypeptides (e.g., ALIGN-2).

Vector as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors". The terms "host cell", "host cell line", and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. A host cell is any type of cellular system that can be used to generate the fusion proteins of the present invention. Host cells include cultured cells, e.g., mammalian cultured cells, such as CHO cells, BH cells, NSO cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue.

Effective amount of an agent refers to the amount that is necessary to result in a physiological change in the cell or tissue to which it is administered.

Therapeutically effective amount of an agent, e.g., a pharmaceutical composition, refers to an amount effective, at dosages and for periods of time necessary, to achieve the desired therapeutic or prophylactic result. A therapeutically effective amount of an agent for example eliminates, decreases, delays, minimizes or prevents adverse effects of a disease.

Individual or subject is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). Particularly, the individual or subject is a human.

Pharmaceutical composition refers to a preparation which is in such form as to permit the biological activity of an active ingredient contained therein to be effective, and which contains no additional components which are unacceptably toxic to a subject to which the formulation would be administered.

Pharmaceutically acceptable carrier refers to an ingredient in a pharmaceutical composition, other than an active ingredient, which is nontoxic to a subject. A pharmaceutically acceptable carrier includes, but is not limited to, a buffer, excipient, stabilizer, or preservative.

Treatment (and grammatical variations thereof such as "treat" or "treating") refers to clinical intervention in an attempt to alter the natural course of a disease in the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

Autoimmune disease refers to a non-malignant disease or disorder arising from and directed against an individual's own tissues. Examples of autoimmune diseases or disorders include, but are not limited to, inflammatory responses such as inflammatory skin diseases including psoriasis and dermatitis (e.g., atopic dermatitis); responses associated with inflammatory bowel disease (such as Crohn's disease and ulcerative colitis); dermatitis; allergic conditions such as eczema and asthma; rheumatoid arthritis; systemic lupus erythematosus (SLE) (including but not limited to lupus nephritis, cutaneous lupus); diabetes mellitus (e.g., type 1 diabetes mellitus or insulin dependent diabetes mellitus); multiple sclerosis and juvenile onset diabetes. Additional examples of autoimmune diseases include, for example, multiple sclerosis (MS), lupus, ankylosing spondylitis, arthritis, colitis, type 1 diabetes, Crohn's disease, heart disease, graft versus host disease, complications from immune response in pregnancy, allergies, rejection of cell or solid organ transplant, Amyotrophic lateral sclerosis (ALS), and myasthenia gravis.

Substantially refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term substantially is therefore used herein to capture the potential lack of completeness inherent in many biological and chemical phenomena.

Unless otherwise defined, all technical and scientific terms used herein have the same meaning as commonly understood by one of ordinary skill in the art to which this application belongs and as commonly used in the art to which this application belongs; such art is incorporated by reference in its entirety. In the case of conflict, the present Specification, including definitions, will control.

DESCRIPTION OF EMBODIMENTS

The present invention provides, among other things, compositions and methods for prophylaxis and treatment of autoimmune disease. The present invention provides compositions and methods for proliferation of regulatory T cells. In one aspect, the present invention uses human interleukin-2 mutein in a method to activate proliferation of regulatory T cells.

Various aspects of the invention are described in detail in the following sections. The use of sections is not meant to limit the invention. Each section can apply to any aspect of the invention. In this application, the use of "or" means "and/or" unless stated otherwise.

IL-2 Muteins

Described herein are various IL-2 muteins that can be used to augment the presence and/or activity of Treg cells. The IL-2 muteins described herein can be used to treat autoimmune disease.

IL-2 variants (also referred to herein as "IL-2 muteins") comprise a sequence of amino acids at least 70%, at least 75%, at least 80%, at least 85%, at least 90%, at least 91%, at least 92%, at least 93% at least 94%, at least 95%, at least 96%, at least 97%, at least 98%, at least 99% identical to wild-type IL-2. IL-2 variants further include a sequence of amino acids at least 70%, at least 75%, at least 80%, at least 85%, at least 90%, at least 91%, at least 92%, at least 93% at least 94%, at least 95%, at least 96%, at least 97%, at least 98%, at least 99% identical to a functional fragment of wild-type IL-2. As used herein, "wild-type IL-2" shall mean the polypeptide having the amino acid sequence of SEQ ID NO: 1 (See Table 1).

Variants may contain one or more substitutions, deletions, or insertions within the wild-type IL-2 amino acid sequence. Residues are designated herein by the one letter amino acid code followed by the IL-2 amino acid position. Substitutions are designated herein by the one letter amino acid code followed by the IL-2 amino acid position followed by the substituting one letter amino acid code.

In one aspect the present invention provides human interleukin-2 muteins comprising at least one amino acid substitution in relation to the wild-type IL-2 selected from a group consisting of T111H, T37Y, E15T, M23L, P34F, E68F and E62A that can selectively activate proliferation of regulatory T cells. Accordingly, in some embodiments, the IL-2 mutein has at least one amino acid substitution characterized by a T111H substitution. In some embodiments, the IL-2 mutein has at least one amino acid substitution characterized by a T37Y substitution. In some embodiments, the IL-2 mutein has at least one amino acid substitution characterized by a E15T substitution. In some embodiments, the IL-2 mutein has at least one amino acid substitution characterized by a M23L substitution. In some embodiments, the IL-2 mutein has at least one amino acid substitution characterized by a P34F substitution. In some embodiments, the IL-2 mutein has at least one amino acid substitution characterized by a E68F substitution. In some embodiments, the IL-2 mutein has at least one amino acid substitution characterized by a E62A substitution.

In one aspect, the IL-2 mutations are selected from a group consisting of V91I, V91L, V91W, E95Q, E95S, E95N, L12Y, L19V, D84E, L19F, E95D, 192Y, E95T, 192V, L12V, 192W, D84T, D84S, M23L, 192F, M23I, H16Y, E15D, L12I, E15S, L12M, D20N, H16R, E15T, D20T, N88S, S87T, V91F, V91M, H16K, L19M, L19I, T111W, F42R, T111F, D109H, P34Q, P34W, D109W, T111N, T41Y, Y45W, L72W, L72F, E68Q, P34F, P65R, P65E, P65Q, E61W, T111H, F42M, T37Y, K43W, T111M, E68F, T111Y, N71W, L72R, E68W, K35T, E106W, K48V, P34Y, D109K, T111Q, E68R, K48S, K48H, P65N, E68Y, D109R, M104H, T41H, M104I, K48I or S87E. Accordingly, in some embodiments, the IL-2 mutein comprises a V91I amino acid substitution. In some embodiments, the IL-2 mutein comprises a V91L substitution. In some embodiments, the IL-2 mutein comprises a V91W substitution. In some embodiments, the IL-2 mutein comprises a E95Q substitution. In some embodiments, the IL-2 mutein comprises a E95N substitution. In some embodiments, the IL-2 mutein comprises a L12Y substitution. In some embodiments, the IL-2 mutein comprises a L19V substitution. In some embodiments, the IL-2 mutein comprises a D84E substitution. In some embodiments, the IL-2 mutein comprises a L19F substitution. In some embodiments, the IL-2 mutein comprises a E95D substitution. In some embodiments, the IL-2 mutein comprises a 192Y substitution. In some embodiments, the IL-2 mutein comprises a E95T substitution. In some embodiments, the IL-2 mutein comprises a 192V substitution. In some embodiments, the IL-2 mutein comprises a L12V substitution. In some embodiments, the IL-2 mutein comprises a 192W substitution. In some embodiments, the IL-2 mutein comprises a D84T substitution. In some embodiments, the IL-2 mutein comprises a D84S substitution. In some embodiments, the IL-2 mutein comprises a M23L substitution. In some embodiments, the IL-2 mutein comprises a 192F substitution. In some embodiments, the IL-2 mutein comprises a M23I substitution. In some embodiments, the IL-2 mutein comprises a H16Y substitution. In some embodiments, the IL-2 mutein comprises a E15D substitution. In some embodiments, the IL-2 mutein comprises a L12I substitution. In some embodiments, the IL-2 mutein comprises a E15S substitution. In some embodiments, the IL-2 mutein comprises a L12M substitution. In some embodiments, the IL-2 mutein comprises a D20N substitution. In some embodiments, the IL-2 mutein comprises a H16R substitution. In some embodiments, the IL-2 mutein comprises a E15T substitution. In some embodiments, the IL-2 mutein comprises a D20T substitution. In some embodiments, the IL-2 mutein comprises a N88S substitution. In some embodiments, the IL-2 mutein comprises a S87T substitution. In some embodiments, the IL-2 mutein comprises a V91F substitution: In some embodiments, the IL-2 mutein comprises a V91M substitution. In some embodiments, the IL-2 mutein comprises a H16K substitution. In some embodiments, the IL-2 mutein comprises a L19M substitution. L19I substitution. In some embodiments, the IL-2 mutein comprises a T111W substitution. In some embodiments, the IL-2 mutein comprises a F42R substitution. In some embodiments, the IL-2 mutein comprises a T111F substitution. In some embodiments, the IL-2 mutein comprises a D109H substitution. In some embodiments, the IL-2 mutein comprises a P34Q substitution. In some embodiments, the IL-2 mutein comprises a P34W substitution. In some embodiments, the IL-2 mutein comprises a D109W substitution. In some embodiments, the IL-2 mutein comprises a T111N substitution. In some embodiments, the IL-2 mutein comprises a T41Y substitution. In some embodiments, the IL-2 mutein comprises a Y45W substitution. In some embodiments, the IL-2 mutein comprises a L72W substitution. In some embodiments, the IL-2 mutein comprises a L72F substitution. In some embodiments, the IL-2 mutein comprises a E68Q substitution. In some embodiments, the IL-2 mutein comprises a P34F substitution. In some embodiments, the IL-2 mutein comprises a P65R substitution. In some embodiments, the IL-2 mutein comprises a P65E substitution. In some embodiments, the IL-2 mutein comprises a P65Q substitution. In some embodiments, the IL-2 mutein comprises a E61W substitution. In some embodiments, the IL-2 mutein comprises a T111H substitution. In some embodiments, the IL-2 mutein comprises a F42M substitution. In some embodiments, the IL-2 mutein comprises a T37Y substitution. In some embodiments, the IL-2 mutein comprises a K43W substitutions. In some embodiments, the IL-2 mutein comprises a T111M substitution. In some embodiments, the IL-2 mutein comprises a E68F substitution. In some embodiments, the IL-2 mutein comprises a T111Y substitution. In some embodiments, the IL-2 mutein comprises a N71W substitution. In some embodiments, the IL-2 mutein comprises a L72R substitution. In some embodiments, the IL-2 mutein comprises a E68W substitution. In some embodiments, the IL-2 mutein comprises a K35T substitution. In some embodiments, the IL-2 mutein comprises a E106W substitution. In some embodiments, the IL-2 mutein comprises a K48V substitution. In some embodiments, the IL-2 mutein comprises a P34Y substitution. In some embodiments, the IL-2 mutein comprises a D109K substitution. In some embodiments, the IL-2 mutein comprises a T111Q substitution. In some embodiments, the IL-2 mutein comprises a E68R substitution. In some embodiments, the IL-2 mutein comprises a K48S substitution. In some embodiments, the IL-2 mutein comprises a K48H substitution. In some embodiments, the IL-2 mutein comprises a P65N substitution. In some embodiments, the IL-2 mutein comprises a E68Y substitution. In some embodiments, the IL-2 mutein comprises a D109R substitution. In some embodiments, the IL-2 mutein comprises a M104H substation. In some embodiments, the IL-2 mutein comprises a T41H substitution. In some embodiments, the IL-2 mutein comprises a M104I substitution. In some embodiments, the IL-2 mutein comprises a K48I substitution. In some embodiments, the IL-2 mutein comprises a S87E substitution. In some embodiments, the IL-2 mutein comprises more than substitution selected from V91I, V91L, V91W, E95Q, E95S, E95N, L12Y, L19V, D84E, L19F, E95D, 192Y, E95T, 192V, L12V, 192W, D84T, D84S, M23L, 192F, M23I, H16Y, E15D, L12I, E15S, L12M, D20N, H16R, E15T, D20T, N88S, S87T, V91F, V91M, H16K, L19M, L19I, T111W, F42R, T111F, D109H, P34Q, P34W, D109W, T111N, T41Y, Y45W, L72W, L72F, E68Q, P34F, P65R, P65E, P65Q, E61W, T111H, F42M, T37Y, K43W, T111M, E68F, T111Y, N71W, L72R, E68W, K35T, E106W, K48V, P34Y, D109K, T111Q, E68R, K48S, K48H, P65N, E68Y, D109R, M104H, T41H, M104I, K48I and S87E.

In one aspect, the invention provides immunosuppressive IL-2 variants that have a higher affinity for IL-2Rα than wild-type IL-2. For example, in some embodiments, the IL-2 muteins that have higher affinity for IL-2Rα include IL-2 muteins that have an amino acid substitution selected from T111H, T37Y, P34F and E68F. In some embodiments, the IL-2 variants described herein have a binding affinity of between about $4.35 \times 10^{-6}$ (M) to about $7.62 \times 10^{-11}$ (M) Accordingly, in some embodiments the IL-2 variants described herein have a binding affinity of about $4 \times 10^{-6}$ (M), about $5 \times 10^{-6}$ (M), about $6 \times 10^{-6}$ (M), about $7 \times 10^{-6}$ (M), or about $8 \times 10^{-6}$ (M).

In some embodiments, IL-2 variants contain one or more mutations in positions of the IL-2 sequence that either contact IL-2Rα or alter the orientation of other positions contacting IL-2Rα, resulting in higher affinity for IL-2Rα. The mutations may be in or near areas known to be in close proximity to IL-2Rα predicted based on published crystal structures. Described herein are specific IL-2 muteins designed and tested for functional properties in in vitro binding assays and in in vivo assays.

In another aspect, the invention provides immunosuppressive IL-2 variants that have a lower affinity for IL-2Rβ than wild-type IL-2. For example, in some embodiments the IL-2 muteins that have lower affinity for IL-2Rβ include IL-2 muteins that have amino acid substitution selected from E15T and M23L. In some embodiments, the IL-2 variants have an affinity for IL-2Rβ of greater than $1.6 \times 10^{-6}$ (M).

In yet another aspect, the invention provides an immunosuppressive IL-2 mutein that have a lower affinity for IL-2Rα. In one embodiment, the IL-2 mutein that has a lower affinity for IL-2Rα comprises a E62A substitution.

In one aspect, the IL-2 muteins have higher binding affinity for IL-2Rβ than WT IL-2.

Immunosuppressive IL-2 variants also include variants that demonstrate altered signaling through certain pathways activated by wild-type IL-2 via the IL-2R and result in preferential proliferation/survival/activation of T-reg. Molecules known to be phosphorylated upon activation of the IL-2R include STAT5, p38, ERK, SYK, LCK, AKT and mTOR. Compared to wild-type IL-2, the immunosuppressive IL-2 variant can possess a reduced PI3K signaling ability in FOXP3 T cells, which can be measured by a reduction in the phosphorylation of AKT and/or mTOR as compared to wild-type IL-2. Such variants may include mutations in positions that either contact IL-2Rβ or IL-2Rγ or alter the orientation of other positions contacting IL-2Rβ or IL-2Rγ.

In certain embodiments, the IL-2 variant comprises a combination of mutations that combine mutations that increase or decrease binding to IL-2Rα or IL-2Rβ or both. In preferred embodiments, the IL-2 variant stimulates STAT5 phosphorylation in FOXP3-positive regulatory T cells but has reduced ability to induce STAT5 and AKT phosphorylation in FOXP3-negative T cells as compared to wild-type IL-2.

In some embodiments, the IL-2 variants may further comprise one or more mutations as compared to the wild-type IL-2 sequence that do not have an effect on the affinity for IL-2Rβ or IL-2Rγ, provided the IL-2 variant promotes the preferential proliferation, survival, activation or function of $FOXP3^{+}$ T-reg over that of other T cells that do not express FOXP3. In preferred embodiments, such mutations are conservative mutations.

In some embodiments, as used herein, IL-2 muteins suitable for the present invention include any wild-type and modified IL-2 variants (e.g., IL-2 proteins with amino acid mutations, deletions, insertions, and/or fusion proteins) that retain substantial IL-2 biological activity. Typically, a recombinant IL-2 protein is produced using recombinant technology. However, IL-2 proteins (wild-type or modified) purified from natural resources or synthesized chemically can be used according to the present invention.

In some embodiments, a suitable recombinant IL-2 mutein has an in vivo half-life of or greater than about 1 minute, 2 minutes, 10 minutes, 15 minutes, 30 minutes, 60 minutes, 70 minutes, 80 minutes, 90 minutes, 100 minutes, 2 hours, 3 hours, 4 hours, 5 hours, 6 hours, 7 hours, 8 hours, 9 hours, 10 hours, 12 hours, or 24 hours. In some embodiments, a suitable recombinant IL-2 mutein or a recombinant IL-2 fusion protein has an in vivo half-life of or greater than about 24 hours, 30 hours, 36 hours, 42 hours, 48 hours, 54 hours, or 60 hours. In some embodiments, a recombinant IL-2 mutein has an in vivo half-life of between 0.5 and 24 hours, between 1 day and 10 days, between 1 day and 9 days, between 1 day and 8 days, between 1 day and 7 days, between 1 day and 6 days, or between 1 day and 5 days.

In some embodiments, presented herein are engineered recombinant IL-2 variants. In some embodiments, the engineered recombinant variants are fused to IgG Fc. In some embodiments, the engineered recombinant IL-2 variants are fused to human IgG1 Fc.

As will be understood by those of skill in the art, any such heavy chain CDR sequence may be readily combined with IL-2, e.g., by techniques of molecular biology, with any other antibody sequences or domains provided herein or otherwise known in the art, including any framework regions, CDRs, or constant domains, or portions thereof as disclosed herein or otherwise known in the art, as may be present in an antibody or binding molecule of any format as disclosed herein or otherwise known in the art.

Autoimmune Diseases

Autoimmune diseases, disorders, or conditions may be amenable to treatment with or may be prevented by administration of an IL-2 mutein that promotes Treg proliferation and/or activity in a subject. In some embodiments, one or more IL-2 muteins described herein are used to treat an autoimmune disease, disorder or condition.

Such diseases, disorders, and conditions that may be diminished in onset and/or severity include, but are not limited to, inflammation, autoimmune disease, paraneoplastic autoimmune diseases, cartilage inflammation, fibrotic disease and/or bone degradation, arthritis, rheumatoid arthritis, juvenile arthritis, juvenile rheumatoid arthritis, pauciarticular juvenile rheumatoid arthritis, polyarticular juvenile rheumatoid arthritis, systemic onset juvenile rheumatoid arthritis, juvenile ankylosing spondylitis, juvenile enteropathic arthritis, juvenile reactive arthritis, juvenile Reter's Syndrome, SEA Syndrome (Seronegativity, Enthesopathy, Arthropathy Syndrome), juvenile dermatomyositis, juvenile psoriatic arthritis, juvenile scleroderma, juvenile systemic lupus erythematosus, juvenile vasculitis, pauciarticular rheumatoid arthritis, polyarticular rheumatoid arthritis, systemic onset rheumatoid arthritis, ankylosing spondylitis, enteropathic arthritis, reactive arthritis, Reter's Syndrome, SEA Syndrome (Seronegativity, Enthesopathy, Arthropathy Syndrome), dermatomyositis, psoriatic arthritis, scleroderma, systemic lupus erythematosus, vasculitis, myolitis, polymyolitis, dermatomyolitis, osteoarthritis, polyarteritis nodossa, Wegener's granulomatosis, arteritis, poloymyalgia rheumatica, sarcoidosis, scleroderma, sclerosis, primary biliary sclerosis, sclerosing cholangitis, Sjogren's syndrome, psoriasis, plaque psoriasis, guttate psoriasis, inverse psoriasis, pustular psoriasis, erythrodermic psoriasis, dermatitis, atopic dermatitis, atherosclerosis, lupus, Still's disease, Systemic Lupus Erythematosus (SLE), myasthenia gravis, inflammatory bowel disease (IBD), Crohn's disease, ulcerative colitis, celiac disease, multiple sclerosis (MS), asthma, COPD, Guillain-Barre disease, Type I diabetes mellitus, thyroiditis (e.g., Graves' disease), Addison's disease, Raynaud's phenomenon, autoimmune hepatitis, GVHD, transplantation rejection, and the like. In specific embodiments, pharmaceutical compositions comprising a therapeutically effective amount of a T-reg-selective IL-2 variant are provided.

In some embodiments, the disease is selected from a group consisting of MS, lupus, ankylosing spondylitis, arthritis, colitis, Type I diabetes, mitigate severity of inflammatory disease, Crohn's disease, heart disease, mitigate complications from immune response in pregnancy, mitigate complications from graft-versus-host disease (GVHD), mitigate severity of allergies, reduce rejection of HSC or allogeneic solid organ transplant, depression, ALS and/or myasthenia gravis.

The term "treatment" encompasses alleviation or prevention of at least one symptom or other aspect of a disorder, or reduction of disease severity, and the like. A T-reg-selective IL-2 variant need not effect a complete cure, or eradicate every symptom or manifestation of a disease, to constitute a viable therapeutic agent. As is recognized in the pertinent field, drugs employed as therapeutic agents may reduce the severity of a given disease state, but need not abolish every manifestation of the disease to be regarded as useful therapeutic agents. Similarly, a prophylactically administered treatment need not be completely effective in preventing the onset of a condition in order to constitute a viable prophylactic agent. Simply reducing the impact of a disease (for example, by reducing the number or severity of its symptoms, or by increasing the effectiveness of another treatment, or by producing another beneficial effect), or reducing the likelihood that the disease will occur or worsen in a subject, is sufficient. One embodiment of the invention is directed to a method comprising administering to a patient A T-reg-selective IL-2 variant in an amount and for a time sufficient to prevent or treat i.e. induce a sustained improvement over baseline of an indicator that reflects the severity of the particular disorder.

Regulatory T Cells (Tregs) in Suppressing Autoimmune Inflammation

Regulatory T cells (Treg) cells are FOXP3+ CD4+ cells that play an important role in maintaining self-tolerance and normal immune homeostasis, and suppressing autoimmune inflammation. Current immunosuppressive therapeutics generally target individual proinflammatory pathways and often exhibit partial efficacy or are applicable only to specific diseases. The present invention provides a method to suppress autoimmune disease involving increased selective production and activation of natural suppressor cells.

Described herein are therapeutic agents that selectively promote T-reg cell proliferation, survival, activation and/or function. By "selectively promote," it is meant the therapeutic agent promotes the activity in T-reg cells but has limited or lacks the ability to promote activity in non-regulatory T cells.

In certain embodiments, the agent is an IL-2 variant. In particular, the IL-2 variant promotes these activities of T-reg cell growth/survival but have a reduced ability, as compared to wild-type IL-2, to promote non-regulatory T-cell (FOXP3 CD25−) and NK cell proliferation, survival, activation and/or function, thus minimizing side-effects.

In certain embodiments, such IL-2 variants function through a combination of elevated affinity for the IL-2R subunit IL-2Rα (CD25) and a reduced affinity for the signaling subunits IL-2Rβ and/or IL-2Rγ. Whereas IL-2 and variants thereof have been used in the art as immunostimulatory agents, e.g., in methods of treating cancer or infectious diseases, the IL-2 variants described herein are particularly useful as immunosuppressive agents, e.g., in methods of treating inflammatory disorders.

IL-2 Fusion Proteins

In some embodiments, a suitable IL-2 mutein described herein can be fused to another peptide. For example, a recombinant IL-2 mutein may be a fusion protein between an IL-2 domain and another domain or moiety that can facilitate a therapeutic effect of IL-2 by, for example, enhancing or increasing stability, potency and/or delivery of IL-2 protein, or reducing or eliminating immunogenicity, or clearance. Such suitable domains or moieties for a IL-2 fusion protein include but are not limited to Fc domain, XTEN domain, or human albumin fusions. In other embodiments, such suitable domains or moieties for an IL-2 fusion protein include a VH domain of an antibody.

Fc Domain

In some embodiments, a suitable recombinant IL-2 protein comprises an Fc domain or a portion thereof that binds to the FcRn receptor. As a non-limiting example, a suitable Fc domain may be derived from an immunoglobulin subclass such as IgG. In some embodiments, a suitable Fc domain is derived from IgG1, IgG2, IgG3, or IgG4. In some embodiments, a suitable Fc domain is derived from IgM, IgA, IgD, or IgE. Particularly suitable Fc domains include those derived from human or humanized antibodies. In some embodiments, a suitable Fc domain is a modified Fc portion, such as a modified human Fc portion.

In some embodiments, a suitable Fc domain comprises an amino acid sequence as provided in Table 1.

TABLE 1

Exemplary Fc domains

| Sequence ID No. (description) | Fc Domain* |
|---|---|
| SEQ ID NO: 9 (wild-type human IgG1 Fc) | DKTHTCPPCPAPELLGGPSVFLFPPKPKDTLMISRTPEVTCVVVDVSHEDPEVKENWYVD GVEVHNAKTKPREEQYNSTYRVVSVLTVLHQDWLNGKEYKCKVSNKALPAPIEKTISKAK GQPREPQVYTLPPSRDELTKNQVSLTCLVKGFYPSDIAVEWESNGQPENNYKTTPPVLDS DGSFFLYSKLTVDKSRWQQGNVFSCSVMHEALHNHYTQKSLSLSPGK |
| SEQ ID NO:10 (human IgG1 Fc-LALA) | DKTHTCPPCPAPEAAGGPSVFLFPPKPKDTLMISRTPEVTCVVVDVSHEDPEVKENWYVD GVEVHNAKTKPREEQYNSTYRVVSVLTVLHQDWLNGKEYKCKVSNKALPAPIEKTISKAK GQPREPQVYTLPPSRDELTKNQVSLTCLVKGFYPSDIAVEWESNGQPENNYKTTPPVLDS DGSFFLYSKLTVDKSRWQQGNVFSCSVMHEALHNHYTQKSLSLSPGK |

TABLE 1-continued

Exemplary Fc domains

| Sequence ID No. (description) | Fc Domain* |
|---|---|
| SEQ ID NO:11 (human IgG1 Fc-NHance) | DKTHTCPPCPAPELLGGPSVFLFPPKPKDTLMISRTPEVTCVVVDVSHEDPEVKENWYVD GVEVHNAKTKPREEQYNSTYRVVSVLTVLHQDWLNGKEYKCKVSNKALPAPIEKTISKAK GQPREPQVYTLPPSRDELTKNQVSLTCLVKGFYPSDIAVEWESNGQPENNYKTTPPVLDS DGSFFLYSKLTVDKSRWQQGNVFSCSVMHEALKFHYTQKSLSLSPGK |
| SEQ ID NO:12 (human IgG1 Fc-LALA + NHance) | DKTHTCPPCPAPEAAGGPSVFLFPPKPKDTLMISRTPEVTCVVVDVSHEDPEVKENWYVD GVEVHNAKTKPREEQYNSTYRVVSVLTVLHQDWLNGKEYKCKVSNKALPAPIEKTISKAK GQPREPQVYTLPPSRDELTKNQVSLTCLVKGFYPSDIAVEWESNGQPENNYKTTPPVLDS DGSFFLYSKLTVDKSRWQQGNVFSCSVMHEALKFHYTQKSLSLSPGK |

*numbering of amino acids based on EU numbering. LALA and NHance mutations are underlined.

In some embodiments, a suitable Fc domain comprises an amino acid sequence at least 50%, 55%, 60%, 65%, 70%, 75%, 80%, 85%, 90%, 91%, 92%, 93%, 94%, 95%, 96%, 97%, 98%, 99% or more homologous or identical to Fc domain sequences disclosed in Table 1.

It is contemplated that improved binding between the Fc domain and the FcRn receptor results in prolonged serum half-life of the recombinant protein. Thus, in some embodiments, a suitable Fc domain comprises one or more amino acid mutations that lead to improved binding to FcRn. Various mutations within the Fc domain that effect improved binding to FcRn are known in the art and can be adapted to practice the present invention. In some embodiments, a suitable Fc domain comprises one or more mutations at one or more positions corresponding to Thr 250, Met 252, Ser 254, Thr 256, Thr 307, Glu 380, Met 428, His 433 and/or Asn 434 of human IgG1, according to EU numbering.

In some embodiments, a suitable Fc domain comprises one or more mutations at one or more positions corresponding to L234, L235, H433 and N434 of human IgG1, according to EU numbering.

The Fc portion of a recombinant fusion protein may lead to targeting of cells that express Fc receptors leading to pro-inflammatory effects. Some mutations in the Fc domain reduce binding of the recombinant protein to the Fc gamma receptor and thereby inhibit effector functions. In one embodiment, effector function is antibody-dependent cell-mediated cytotoxicity (ADCC). For example, a suitable Fc domain may contain mutations of L234A (Leu234Ala) and/or L235A (Leu235Ala) (EU numbering). In some embodiments the L234A and L235A mutations are also referred to as the LALA mutations. As a non-limiting example, a suitable Fc domain may contain mutations L234A and L235A (EU numbering).

In some embodiments, a suitable Fc domain may contain mutations of H433K (His433Lys) and/or N434F (Asn434Phe) (EU numbering). As a non-limiting example, a suitable Fc domain may contain mutations H433K and N434F (EU numbering). In some embodiments the H433K and N434F mutations are also referred to as the NHance mutations.

In some embodiments, a suitable Fc domain may contain mutations of L234A (Leu234Ala), L235A (Leu235Ala), H433K (His433Lys) and/or N434F (Asn434Phe) (EU numbering). As a non-limiting example, a suitable Fc domain may contain mutations L234A, L235A, H433K and N434F (EU numbering). Additional amino acid substitutions that can be included in the Fc domain include those described in, e.g., U.S. Pat. Nos. 6,277,375; 8,012,476; and 8,163,881, which are incorporated herein by reference.

Exemplary IL-2 Fusion Proteins

The present invention provides IL-2 muteins that preferentially expand Tregs over, for example Teff or NK cells. The IL-2 muteins provided herein may be altered to include or fused to molecules that extend the serum half-life of the mutein without increasing the risk that such half-life extension would increase the likelihood or the intensity of a side-effect or adverse event in a patient. Subcutaneous dosing of such an extended serum half-life mutein may allow for prolonged target coverage with lower systemic maximal exposure ($C_{max}$). Extended serum half-life may allow a lower or less frequent dosing regimen of the mutein.

The IL-2 variant may comprise one or more compounds to increase the serum-half-life of the IL-2 variant when administered to a patient. Such half-life extending molecules include water soluble polymers (e.g., polyethylene glycol (PEG)), low- and high-density lipoproteins, antibody Fc (monomer or dimer), transthyretin (TTR), and TGF-β latency associated peptide (LAP). Also contemplated are IL-2 variants comprising a combination of serum half-life extending molecules, such as PEGylated TTR (US Pat. Appl. Publ. No. 2003/0195154).

The serum half-life of the IL-2 muteins provided herein may be extended by essentially any method known in the art. Such methods include altering the sequence of the IL-2 mutein to include a peptide that binds to the neonatal Fey receptor or bind to a protein having extended serum half-life, e.g., IgG or human serum albumin. In other embodiments, the IL-2 mutein is fused to a polypeptide that confers extended half-life on the fusion molecule. Such polypeptides include an IgG Fc or other polypeptides that bind to the neonatal Fey receptor, human serum albumin, or polypeptides that bind to a protein having extended serum half-life.

In some embodiments, the IL-2 mutein is fused to an IgG Fc molecule. The IL-2 mutein may be fused to the N-terminus or the C-terminus of the IgG Fc region.

One embodiment of the present invention is directed to a dimer comprising two Fc-fusion polypeptides created by fusing an IL-2 mutein to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain bonds form between the Fc moieties to yield the dimer.

The term "Fc polypeptide" Or "Fc region" as used herein includes native and mutein forms of polypeptides derived from the Fc region of an antibody and can be part of either the IL-2 mutein fusion proteins or the anti-IL-2 antibodies of the invention. Truncated forms of such polypeptides containing the hinge region that promotes dimerization also are included. In certain embodiments, the Fc region comprises an antibody CH2 and CH3 domain. Along with extended serum half-life, fusion proteins comprising Fc moieties (and oligomers formed therefrom) offer the advantage of facile purification by affinity chromatography over Protein A or Protein G columns. Preferred Fc regions are derived from human IgG, which includes IgG1, lgG2, lgG3, and lgG4. Herein, specific residues within the Fc are identified by position. All Fc positions are based on the EU numbering scheme.

One of the functions of the Fc portion of an antibody is to communicate to the immune system when the antibody binds its target. This is considered "effector function." Communication leads to antibody-dependent cellular cytotoxicity (ADCC), antibody-dependent cellular phagocytosis (ADCP), and/or complement dependent cytotoxicity (CDC). ADCC and ADCP are mediated through the binding of the Fc to Fc receptors on the surface of cells of the immune system. CDC is mediated through the binding of the Fc with proteins of the complement system, e.g., Clq.

The IgG subclasses vary in their ability to mediate effector functions. For example, IgG1 is superior to IgG2 and lgG4 at mediating ADCC and CDC. The effector function of an antibody can be increased, or decreased, by introducing one or more mutations into the Fc. Embodiments of the invention include IL-2 mutein Fc fusion proteins having an Fc engineered to increase effector function (U.S. Pat. No. 7,317,091 and Strohl, Curr. Opin. Biotech., 20:685-691, 2009; both incorporated herein by reference in its entirety).

Manufacturing Methods

The IL-2 variants described herein can be produced using any suitable method known in the art. Such methods include, for example, constructing a DNA sequence encoding the IL-2 variant and expressing those sequences in a suitably transformed host. This method will produce the recombinant variant of this invention. However, the variants may also be produced by chemical synthesis or a combination of chemical synthesis and recombinant DNA technology. Batch-wise production or perfusion production methods are known in the art. See Freshey, R. I. (ed), 3 "Animal Cell Culture: A Practical Approach," 2nd ed., 1992, IRL Press. Oxford, England; Mather, J. P. "Laboratory Scaleup of Cell Cultures (0.5-50 liters)," Methods Cell Biolog 57:219-527 (1998); Hu, W. S., and Aunins, J. G., "Large-scale Mammalian Cell Culture," Curr Opin Biotechnol 8:148-153 (1997); Konstantinov, K. B., Tsai, Y., Moles, D., Matanguihan, R., "Control of long-term perfusion Chinese hamster ovary cell culture by glucose auxostat.," Biotechnol Prag 12:100-109 (1996).

In some embodiments of producing the IL-2 variants described herein, a DNA sequence is constructed by isolating or synthesizing a DNA sequence encoding the wild type IL-2 and then changing one or more codons by site specific mutagenesis. See, e.g., Mark et. al., "Site-specific Mutagenesis Of The Human Fibroblast Interferon Gene", Proc. Natl. Acad. Sci. USA 81, pp. 5662-66 (1984); and U.S. Pat. No. 4,588,585, incorporated herein by reference. Various mutations and manners of creating same are known in the art and include, for example, amino acid and/or nucleic acid deletions, insertions, substitutions and/or fusions.

Another method of constructing a DNA sequence encoding the IL-2 variant would be chemical synthesis. This for example includes direct synthesis of a peptide by chemical means of the protein sequence encoding for an IL-2 variant exhibiting the properties described herein. This method may incorporate both natural and unnatural amino acids. Alternatively, a gene which encodes the desired IL-2 variant may be synthesized by chemical means using an oligonucleotide synthesizer. In some embodiments, such oligonucleotides are designed based on the amino acid sequence of the desired IL-2 variant, and selecting those codons that are favored in the host cell in which the recombinant variant will be produced. In this regard, it is well recognized that the genetic code is degenerate-that an amino acid may be coded for by more than one codon. For example, Phe (F) is coded for by two codons, TTC or TTT, Tyr (Y) is coded for by TAC or TAT and his (H) is coded for by CAC or CAT. Trp (W) is coded for by a single codon, TGG. Accordingly, it will be appreciated that for a given DNA sequence encoding a particular IL-2 variant, there will be many DNA degenerate sequences that will code for that IL-2 variant.

The DNA sequence encoding the IL-2 variant, whether prepared by site directed mutagenesis, chemical synthesis or other methods, may or may not also include DNA sequences that encode a signal sequence. In some embodiments, such signal sequence, if present, is one recognized by the cell chosen for expression of the IL-2 variant. It may be prokaryotic, eukaryotic or a combination of the two. It may also be the signal sequence of native IL-2. The inclusion of a signal sequence depends on whether it is desired to secrete the IL-2 variant from the recombinant cells in which it is made. In some embodiments, if the chosen cells are prokaryotic, the DNA sequence does not encode a signal sequence. In some embodiments, if the chosen cells are eukaryotic, a signal sequence is encoded and may have the wild-type IL-2 signal sequence.

Standard methods may be applied to synthesize a gene encoding an IL-2 variant. For example, the complete amino acid sequence may be used to construct a back translated gene. A DNA oligomer containing a nucleotide sequence coding for an IL-2 variant may be synthesized. For example, several small oligonucleotides coding for portions of the desired polypeptide may be synthesized and then ligated. The individual oligonucleotides may contain 5' or 3' overhangs for complementary assembly.

Once assembled (by synthesis, site-directed mutagenesis or another method), the DNA sequences encoding an IL-2 variant will be inserted into an expression vector and operatively linked to an expression control sequence appropriate for expression of the IL-2 variant in the desired transformed host. Proper assembly may be confirmed by nucleotide sequencing, restriction mapping, and expression of a biologically active polypeptide in a suitable host. As is known in the art, in order to obtain high expression levels of a transfected gene in a host, the gene is operatively linked to transcriptional and translational expression control sequences that are functional in the chosen expression host. The choice of expression control sequence and expression vector will depend upon the choice of host. A wide variety of expression host/vector combinations may be employed.

Any suitable host may be used to produce the IL-2 variant, including bacteria, fungi (including yeasts), plant, insect, mammal, or other appropriate animal cells or cell lines, as well as transgenic animals or plants. These hosts may include well known eukaryotic and prokaryotic hosts, such as strains of *E. coli*, *Pseudomonas*, *Bacillus*, *Streptomyces*, fungi, yeast, insect cells such as *Spodoptera frugiperda* (Sf9), animal cells such as Chinese hamster ovary (CHO) and mouse cells such as NS/0, African green monkey cells such as COS 1, COS 7, BSC 1, BSC 40, and BNT 10, and human cells, as well as plant cells in tissue culture. In some embodiments, for animal cell expression, CHO cells and COS 7 cells in cultures and the CHO cell line CHO (DHFR−) or the HKB line may be used.

It should be understood that not all vectors and expression control sequences will function equally well to express the DNA sequences described herein. Neither will all hosts function equally well with the same expression system. However, one of skill in the art may make a selection among these vectors, expression control sequences and hosts without undue experimentation. For example, in selecting a vector, the host cell is considered because the vector must replicate in it. The vector copy number, the ability to control that copy number, and the expression of any other proteins encoded by the vector, such as antibiotic markers, may also be considered. For example, in some embodiments, vectors for use in this invention include those that allow the DNA encoding the IL-2 variants to be amplified in copy number. Such amplifiable vectors are well known in the art. They include, for example, vectors able to be amplified by DHFR amplification (see, e.g., Kaufman, U.S. Pat. No. 4,470,461, Kaufman and Sharp, "Construction Of A Modular Dihydrafolate Reductase cDNA Gene: Analysis Of Signals Utilized For Efficient Expression", Mol. Cell. Biol., 2, pp. 1304-19 (1982)) or glutamine synthetase ("GS") amplification (see, e.g., U.S. Pat. No. 5,122,464 and European published application 338,841).

The IL-2 variants may be glycosylated or unglycosylated depending on the host organism used to produce the variant. In some embodiments, when bacteria are chosen as the host, then the IL-2 variant produced will be unglycosylated. In some embodiments, eukaryotic cells will glycosylate the IL-2 variant. The IL-2 variant produced by the transformed host can be purified according to any suitable method. Various methods are known for purifying IL-2. See, e.g., Current Protocols in Protein Science, Vol. 2. Eds: John E. Coligan, Ben M. Dunn, Hidde L. Ploehg, David W. Speicher, Paul T. Wingfield, Unit 6.5 (Copyright 1997, John Wiley and Sons, Inc).

Pharmaceutical Composition and Administration

The present invention further provides pharmaceutical compositions comprising therapeutically active ingredients in accordance with the invention (e.g., recombinant IL-2 mutein protein, recombinant IL-2 mutein fusion protein or recombinant IL-2 mutein-Fc fusion protein), together with one or more pharmaceutically acceptable carriers or excipients. Such pharmaceutical compositions may optionally comprise one or more additional therapeutically-active substances.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation.

Formulations of the pharmaceutical compositions described herein may be prepared by any method known or hereafter developed in the art of pharmacology. In general, such preparatory methods include the step of bringing the active ingredient into association with a diluent or another excipient or carrier and/or one or more other accessory ingredients, and then, if necessary and/or desirable, shaping and/or packaging the product into a desired single- or multi-dose unit.

A pharmaceutical composition in accordance with the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient or carrier, and/or any additional ingredients in a pharmaceutical composition in accordance with the invention will vary, depending upon the identity, size, and/or condition of the subject treated and further depending upon the route by which the composition is to be administered. By way of example, the composition may comprise between 0.1% and 100% (w/w) active ingredient.

Pharmaceutical formulations may additionally comprise a pharmaceutically acceptable excipient or carrier, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's *The Science and Practice of Pharmacy,* 21$^{st}$ Edition, A. R. Gennaro (Lippincott, Williams & Wilkins, Baltimore, MD, 2006; incorporated herein by reference) discloses various excipients used in formulating pharmaceutical compositions and known techniques for the preparation thereof. Except insofar as any conventional excipient medium or carrier is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, a pharmaceutically acceptable excipient or carrier is at least 95%, at least 96%, at least 97%, at least 98%, at least 99%, or 100% pure. In some embodiments, an excipient or carrier is approved for use in humans and for veterinary use. In some embodiments, an excipient or carrier is approved by United States Food and Drug Administration. In some embodiments, an excipient or carrier is pharmaceutical grade. In some embodiments, an excipient or carrier meets the standards of the United States Pharmacopoeia (USP), the European Pharmacopoeia (EP), the British Pharmacopoeia, and/or the International Pharmacopoeia.

Pharmaceutically acceptable excipients or carriers used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients or carriers may optionally be included in pharmaceutical formulations. Excipients or carriers such as cocoa butter and suppository waxes, coloring agents, coating agents, sweetening, flavoring, and/or perfuming agents can be present in the composition, according to the judgment of the formulator.

Suitable pharmaceutically acceptable excipients or carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, sugars such as mannitol, sucrose, or others, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents (e.g., lubricants, preservatives, stabilizers, wetting agents, emulsifiers, salts for influencing osmotic pressure, buffers, coloring, flavoring and/or aromatic substances and the like) which do not deleteriously react with the active compounds or interfere with their activity. In a preferred embodiment, a water-soluble carrier suitable for intravenous administration is used.

A suitable pharmaceutical composition or medicament, if desired, can also contain minor amounts of wetting or emulsifying agents, or pH buffering agents. A composition can be a liquid solution, suspension, emulsion, tablet, pill, capsule, sustained release formulation, or powder. A composition can also be formulated as a suppository, with traditional binders and carriers such as triglycerides. Oral formulations can include standard carriers such as pharmaceutical grades of mannitol, lactose, starch, magnesium stearate, polyvinyl pyrollidone, sodium saccharine, cellulose, magnesium carbonate, etc.

A pharmaceutical composition or medicament can be formulated in accordance with the routine procedures as a pharmaceutical composition adapted for administration to human beings. For example, in some embodiments, a composition for intravenous administration typically is a solution in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

A recombinant IL-2 mutein protein or recombinant IL-2 mutein-Fc fusion protein described herein can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

General considerations in the formulation and/or manufacture of pharmaceutical agents may be found, for example, *in Remington: The Science and Practice of Pharmacy* 21$^{st}$ ed., Lippincott Williams & Wilkins, 2005 (incorporated herein by reference).

Routes of Administration

A recombinant IL-2 mutein protein or recombinant IL-2 mutein-Fc fusion protein described herein (or a composition or medicament containing a recombinant IL-2 mutein protein described herein) can be administered by any appropriate route. In some embodiments, a recombinant IL-2 mutein protein, recombinant IL-2 mutein-Fc fusion protein or a pharmaceutical composition containing the same is administered systemically. Systemic administration may be intravenous, intradermal, inhalation, transdermal (topical), intraocular, intramuscular, subcutaneous, intramuscular, oral and/or transmucosal administration. In some embodiments, a recombinant IL-2 mutein protein, recombinant IL-2 mutein-Fc fusion protein or a pharmaceutical composition containing the same is administered subcutaneously. As used herein, the term "subcutaneous tissue", is defined as a layer of loose, irregular connective tissue immediately beneath the skin. For example, the subcutaneous administration may be performed by injecting a composition into areas including, but not limited to, the thigh region, abdominal region, gluteal region, or scapular region. In some embodiments, a recombinant IL-2 mutein protein, recombinant IL-2 mutein-Fc fusion protein or a pharmaceutical composition comprising the same is administered intravenously. In some embodiments, a recombinant IL-2 mutein protein, recombinant IL-2 mutein-Fc fusion protein or a pharmaceutical composition containing the same is administered orally. In some embodiments, a recombinant IL-2 mutein protein, recombinant IL-2 mutein-Fc fusion protein or a pharmaceutical composition containing the same is administered intramuscularly. In some embodiments, more than one route can be used concurrently.

In some embodiments, administration results only in a localized effect in an individual, while in other embodiments, administration results in effects throughout multiple portions of an individual, for example, systemic effects. Typically, administration results in delivery of a recombinant IL-2 mutein protein or recombinant IL-2 mutein-Fc fusion protein systemically. In some embodiments, the recombinant IL-2 mutein protein or recombinant IL-2 mutein-Fc fusion protein is delivered to one or more target tissues including, but not limited to, heart, brain, spinal cord, striated muscle (e.g., skeletal muscle), smooth muscle, kidney, liver, lung, and/or spleen.

Dosage Forms and Dosing Regimen

In some embodiments, a composition is administered in a therapeutically effective amount and/or according to a dosing regimen that is correlated with a particular desired outcome (e.g., with treating or reducing risk for autoimmune disease).

Particular doses or amounts to be administered in accordance with the present invention may vary, for example, depending on the nature and/or extent of the desired outcome, on particulars of route and/or timing of administration, and/or on one or more characteristics (e.g., weight, age, personal history, genetic characteristic, lifestyle parameter, etc., or combinations thereof). Such doses or amounts can be determined by those of ordinary skill. In some embodiments, an appropriate dose or amount is determined in accordance with standard clinical techniques. Alternatively or additionally, in some embodiments, an appropriate dose or amount is determined through use of one or more in vitro or in vivo assays to help identify desirable or optimal dosage ranges or amounts to be administered.

In various embodiments, a recombinant IL-2 mutein protein is administered at a therapeutically effective amount. Generally, a therapeutically effective amount is sufficient to achieve a meaningful benefit to the subject (e.g., treating, modulating, curing, preventing and/or ameliorating the underlying disease or condition).

In some embodiments, a provided composition is provided as a pharmaceutical formulation. In some embodiments, a pharmaceutical formulation is or comprises a unit dose amount for administration in accordance with a dosing regimen correlated with achievement of the reduced incidence or risk of autoimmune disease.

In some embodiments, a formulation comprising a recombinant IL-2 mutein protein or recombinant IL-2 mutein-Fc fusion protein described herein administered as a single dose. In some embodiments, a formulation comprising a recombinant IL-2 mutein protein or recombinant IL-2 mutein-Fc fusion protein described herein is administered at regular intervals. Administration at an "interval," as used herein, indicates that the therapeutically effective amount is administered periodically (as distinguished from a one-time dose). The interval can be determined by standard clinical techniques. In some embodiments, a formulation comprising a recombinant IL-2 mutein protein or recombinant IL-2 mutein-Fc fusion protein described herein is administered bimonthly, monthly, twice monthly, triweekly, biweekly, weekly, twice weekly, thrice weekly, daily, twice daily, or every six hours. The administration interval for a single individual need not be a fixed interval, but can be varied over time, depending on the needs of the individual.

As used herein, the term "bimonthly" means administration once per two months (i.e., once every two months); the term "monthly" means administration once per month; the term "triweekly" means administration once per three weeks (i.e., once every three weeks); the term "biweekly" means administration once per two weeks (i.e., once every two weeks); the term "weekly" means administration once per week; and the term "daily" means administration once per day.

In some embodiments, a formulation comprising a recombinant IL-2 mutein protein or recombinant IL-2 mutein-Fc fusion protein described herein is administered at regular intervals indefinitely. In some embodiments, a formulation comprising a recombinant IL-2 mutein protein or recombinant IL-2 mutein-Fc fusion protein described herein is administered at regular intervals for a defined period.

As described herein, the term "therapeutically effective amount" is largely determined based on the total amount of the therapeutic agent contained in the pharmaceutical compositions of the present invention. A therapeutically effective amount is commonly administered in a dosing regimen that may comprise multiple unit doses. For any particular composition, a therapeutically effective amount (and/or an appropriate unit dose within an effective dosing regimen) may vary, for example, depending on route of administration or on combination with other pharmaceutical agents.

In some embodiments, the invention provides pharmaceutical compositions comprising a therapeutically effective amount of one or a plurality of IL-2 muteins described herein with a pharmaceutically acceptable diluent, carrier, solubilizer, emulsifier, preservative, and/or adjuvant.

Combination therapies: In further embodiments, IL-2 muteins described herein are administered in combination with other agents useful for treating a condition with which the patient is afflicted. Examples of such agents include both proteinaceous and non-proteinaceous drugs. When multiple therapeutics are co-administered, dosages may be adjusted accordingly, as is recognized in the pertinent art. "Co-administration" and combination therapy are not limited to simultaneous administration, but also include treatment regimens in which a T-reg-selective IL-2 variant is administered at least once during a course of treatment that involves administering at least one other therapeutic agent to the patient.

In certain embodiments, a IL-2 mutein is administered in combination with an inhibitor of the PI3-K/AKT/mTOR pathway, e.g., rapamycin (Rapamune, sirolimus). Inhibitors of this pathway in combination with IL-2 favor T-reg enrichment.

Although methods and materials similar or equivalent to those described herein can be used in the practice or testing of the present invention, suitable methods and materials are described below. All publications, patent applications, patents, and other references mentioned herein are incorporated by reference in their entirety. The references cited herein are not admitted to be prior art to the claimed invention. In addition, the materials, methods, and examples are illustrative only and are not intended to be limiting.

EXAMPLES

Example 1. Design and Construction of IL-2 Muteins

This example illustrates the design and construction of exemplary IL-2 muteins.

Standard recombinant DNA techniques were used to manipulate DNA (Sambrook et al., Molecular cloning: A laboratory manual; Cold Spring Harbor Laboratory Press, Cold Spring Harbor, N.Y., 1989) and design constructs containing heavy immunoglobulin light and heavy chain nucleotide sequences (Kabat, E. A. et al., (1991) Sequences of Proteins of Immunological Interest, Fifth Ed., NIH Publication No 91-3242). Sequencing of double stranded DNA was carried out to confirm the nucleotide sequence of the constructs.

Exemplary nucleotide residues in the WT IL-2 protein (SEQ ID NO: 1) were mutated to generate exemplary IL-2 muteins (Table 2), which were then characterized for their affinity to bind IL-2Rα, IL-2Rβ, CD25 or CD122. Exemplary IL-2 muteins include at least one amino acid substitution in relation to the wild type IL-2 protein (SEQ ID NO: 1) selected from a group consisting of T111H, T37Y, E15T, M23L, P34F, E68F and E62A.

Further, IgG fusion IL-2 muteins were constructed. In order to prevent intermolecular disulfide bond formation, a C125A mutation was introduced in all IL-2 muteins generated. Accordingly, in some embodiments of the present invention, the IL-2 muteins comprise a C125A mutation. In order to minimize avidity effects and heterodimerization, knob into hole mutations were introduced in IgG Fc region and all IL-2 muteins were fused with only knob mutation introduced IgG.

This example demonstrated the design and construction of exemplary IL-2 muteins (Table 2).

TABLE 2

IL-2 muteins (mutated residues in bold).

| | |
|---|---|
| SEQ ID NO: 1<br>(IL2 WT) | APTSSSTKKTQLQLEHLLLDLQMILNGINNYKNPKLTRMLTFKFYMPKKATELK<br>HLQCLEEELKPLEEVLNLAQSKNFHLRPRDLISNINVIVLELKGSETTFMCEYA<br>DETATIVEFLNRWITFCQSIISTLT |

TABLE 2-continued

| IL-2 muteins (mutated residues in bold). | |
|---|---|
| SEQ ID NO: 2 (T111H) | APTSSSTKKTQLQLEHLLLDLQMILNGINNYKNPKLTRMLTFKFYMPKKATELK<br>HLQCLEEELKPLEEVLNLAQSKNFHLRPRDLISNINVIVLELKGSETTFMCEYA<br>DE**H**ATIVEFLNRWITF**A**QSIISTLT |
| SEQ ID NO: 3 (T37Y) | APTSSSTKKTQLQLEHLLLDLQMILNGINNYKNPKL**Y**RMLTFKFYMPKKATELK<br>HLQCLEEELKPLEEVLNLAQSKNFHLRPRDLISNINVIVLELKGSETTFMCEYA<br>DETATIVEFLNRWITF**A**QSIISTLT |
| SEQ ID NO: 4 (E15T) | APTSSSTKKTQLQL**T**HLLLDLQMILNGINNYKNPKLTRMLTFKFYMPKKATELK<br>HLQCLEEELKPLEEVLNLAQSKNFHLRPRDLISNINVIVLELKGSETTEMCEYA<br>DETATIVEFLNRWITF**A**QSIISTLT |
| SEQ ID NO: 5 (M23L) | APTSSSTKKTQLQLEHLLLDLQ**L**ILNGINNYKNPKLTRMLTFKFYMPKKATELK<br>HLQCLEEELKPLEEVLNLAQSKNFHLRPRDLISNINVIVLELKGSETTFMCEYA<br>DETATIVEFLNRWITF**A**QSIISTLT |
| SEQ ID NO: 6 (P34F) | APTSSSTKKTQLQLEHLLLDLQMILNGINNYKNFKLTRMLT**F**KFYMPKKATELK<br>HLQCLEEELKPLEEVLNLAQSKNFHLRPRDLISNINVIVLELKGSETTEMCEYA<br>DETATIVEFLNRWITF**A**QSIISTLT |
| SEQ ID NO: 7 (E68F) | APTSSSTKKTQLQLEHLLLDLQMILNGINNYKNPKLTRMLTFKFYMPKKATELK<br>HLQCLEEELKPLE**F**VLNLAQSKNFHLRPRDLISNINVIVLELKGSETTFMCEYA<br>DETATIVEFLNRWITF**A**QSIISTLT |
| SEQ ID NO: 8 (E62A) | APTSSSTKKTQLQLEHLLLDLQMILNGINNYKNPKLTRMLTFKFYMPKKATELK<br>HLQCLEE**A**LKPLEEVLNLAQSKNFHLRPRDLISNINVIVLELKGSETTFMCEYA<br>DETATIVEFLNRWITFCQSIISTLT |

Example 2. Production of IgG Fusion IL-2 Muteins

This example illustrates the production of exemplary IgG fusion IL-2 mutein proteins.

First, gene fragments were generated by synthetic gene synthesis and/or PCR from suitable templates and subcloned into standard mammalian expression vector. To produce the IgG IL-2 mutein fusion proteins, exponentially growing Expi293 cells were cotransfected with mammalian expression vectors of IgG light chain, IgG heavy chain with hole mutation, and IgG heavy chain with knob mutation fused to an IL-2 mutein using ExpiFectamine transfection reagent.

Subsequently, fusion proteins were purified from the supernatant by one-step affinity purification with protein A beads equilibrated in PBS. After loading of the supernatant, the column was first washed with PBS. Fusion proteins were eluted with 0.1 M Glycine-HCl/0.3 M NaCl (pH 3.0). Fractions were neutralized with 1 M Tris-HCl pH 8.0 (1:10) and were buffer-exchanged to PBS by dialysis. The protein concentration of purified protein samples was determined by measuring the optical density (OD) at 280 nm, using the molar extinction coefficient calculated on the basis of the amino acid sequence. Accordingly, purified IgG fusion IL-2 muteins were generated.

Example 3. Binding Affinity of IL-2 Mutein Fusion Proteins to IL-2 Receptors

This example measures the binding affinity of exemplary IL-2 mutein fusion proteins to IL-2 receptors. The affinity of the fusion proteins to IL-2 receptors was determined by BioLayer Interferometry (BLI) on a Octet Red96e (Forte Bio) for the human IL-2Rα and IL-2Rβ receptors using recombinant IL-2Rα and IL-2Rβ under the following conditions: ligands comprised biotinylated human IL-2Rα or IL-2Rβ immobilized on SA chip, analytes comprised single dose IgG fusion IL-2 muteins at a temperature of 25° C. in PBS buffer, association: 120 s, dissociation: 600 s, fitting: 1:1 Langmuir binding model. Affinities were determined based on the kinetic rate constants k on and k off (Table 3).

TABLE 3

Affinity measurements based on kinetics for IL-2Rα and IL-2Rβ

| | CD25 | | | | CD122 | | | |
|---|---|---|---|---|---|---|---|---|
| | KD (M) | ka (1/Ms) | kd (1/s) | Rmax | KD (M) | ka (1/Ms) | kd (1/s) | Rmax |
| V91I | 4.87E−08 | 3.03E+05 | 1.48E−02 | 0.5212 | ND | ND | ND | ND |
| V91L | 6.56E−08 | 3.24E+05 | 2.13E−02 | 0.4808 | ND | ND | ND | ND |
| V91W | 5.12E−08 | 2.57E+05 | 1.32E−02 | 0.5794 | ND | ND | ND | ND |
| E95Q | 1.34E−08 | 9.76E+05 | 1.31E−02 | 0.3375 | ND | ND | ND | ND |
| E95S | 1.25E−08 | 9.59E+05 | 1.20E−02 | 0.4495 | ND | ND | ND | ND |
| E95N | 7.30E−12 | 6.69E+04 | 4.88E−07 | 0.1866 | ND | ND | ND | ND |
| L12Y | 2.13E−08 | 1.05E+06 | 2.24E−02 | 0.2956 | ND | ND | ND | ND |
| L19V | 2.54E−08 | 8.55E+05 | 2.17E−02 | 0.4624 | ND | ND | ND | ND |
| D84E | 1.61E−08 | 1.05E+06 | 1.69E−02 | 0.346 | 1.73E−07 | 4.19E+07 | 7.23E+00 | 0.0063 |
| L19F | 1.64E−08 | 8.33E+05 | 1.37E−02 | 0.4624 | ND | ND | ND | ND |
| E95D | 2.28E−08 | 8.18E+05 | 1.86E−02 | 0.4739 | NC | ND | ND | ND |
| I92Y | 2.13E−08 | 8.71E+05 | 1.85E−02 | 0.4531 | 3.96E−07 | 2.55E+05 | 1.01E−01 | 0.0246 |
| E95T | 1.25E−08 | 8.14E+05 | 1.02E−02 | 0.3091 | ND | ND | ND | ND |
| I92V | <1.0E−12 | 4.83E+04 | <1.0E−07 | 0.3608 | ND | ND | ND | ND |

TABLE 3-continued

Affinity measurements based on kinetics for IL-2Rα and IL-2Rβ

| | CD25 | | | | CD122 | | | |
|---|---|---|---|---|---|---|---|---|
| | KD (M) | ka (1/Ms) | kd (1/s) | Rmax | KD (M) | ka (1/Ms) | kd (1/s) | Rmax |
| L12V | 2.14E−08 | 7.30E+05 | 1.56E−02 | 0.3252 | ND | ND | ND | ND |
| I92W | 8.96E−09 | 8.27E+05 | 7.41E−03 | 0.1353 | ND | ND | ND | ND |
| D84T | 1.58E−08 | 6.71E+05 | 1.06E−02 | 0.4242 | ND | ND | ND | ND |
| D84S | 1.16E−08 | 1.13E+06 | 1.31E−02 | 0.2454 | ND | ND | ND | ND |
| M23L | 1.94E−08 | 7.66E+05 | 1.48E−02 | 0.4742 | 1.40E−06 | 8.67E+04 | 1.21E−01 | 0.043 |
| I92F | 3.59E−08 | 4.67E+05 | 1.68E−02 | 0.0944 | ND | ND | ND | ND |
| M23I | 1.96E−08 | 7.86E+05 | 1.54E−02 | 0.4478 | ND | ND | ND | ND |
| H16Y | 5.50E−08 | 4.89E+05 | 2.69E−02 | 0.5193 | ND | ND | ND | ND |
| E15D | 1.48E−07 | 8.12E+03 | 1.20E−03 | 0.4746 | ND | ND | ND | ND |
| L12I | 2.27E−08 | 9.44E+05 | 2.15E−02 | 0.4263 | 3.07E−07 | 3.56E+05 | 1.09E−01 | 0.0158 |
| E15S | 2.40E−08 | 6.61E+05 | 1.58E−02 | 0.3472 | ND | ND | ND | ND |
| L12M | ND | ND | ND | ND | ND | ND | ND | ND |
| D20N | 1.63E−08 | 8.05E+05 | 1.32E−02 | 0.4397 | ND | ND | ND | ND |
| H16R | 3.99E−08 | 4.64E+05 | 1.85E−02 | 0.5379 | ND | ND | ND | ND |
| E15T | 1.00E−08 | 1.71E+06 | 1.71E−02 | 0.2889 | 2.20E−07 | 6.99E+05 | 1.54E−01 | 0.0104 |
| D20T | 5.16E−09 | 2.46E+05 | 1.27E−03 | 0.0403 | ND | ND | ND | ND |
| N88S | 2.54E−08 | 8.29E+05 | 2.11E−02 | 0.429 | ND | ND | ND | ND |
| S87T | 2.47E−08 | 5.97E+05 | 1.48E−02 | 0.3313 | ND | ND | ND | ND |
| V91F | 4.30E−08 | 3.80E+05 | 1.63E−02 | 0.5129 | ND | ND | ND | ND |
| V91M | 2.83E−08 | 7.22E+05 | 2.04E−02 | 0.5343 | ND | ND | ND | ND |
| H16K | 3.28E−08 | 1.31E+04 | 4.28E−04 | 0.4045 | ND | ND | ND | ND |
| L19M | ND | ND | ND | ND | ND | ND | ND | ND |
| L19I | 3.41E−08 | 6.64E+05 | 2.26E−02 | 0.4724 | 2.32E−07 | 2.41E+06 | 5.59E−01 | 0.0164 |
| T111W | 4.07E−08 | 2.55E+05 | 1.04E−02 | 0.0837 | ND | ND | ND | ND |
| F42R | ND | ND | ND | ND | ND | ND | ND | ND |
| T111F | ND | ND | ND | ND | ND | ND | ND | ND |
| D109H | 2.58E−08 | 2.38E+04 | 6.12E−04 | 0.5188 | ND | ND | ND | ND |
| P34Q | ND | ND | ND | ND | ND | ND | ND | ND |
| P34W | 7.38E−08 | 3.80E+05 | 2.80E−02 | 0.1874 | ND | ND | ND | ND |
| D109W | 9.83E−08 | 1.91E+04 | 1.88E−03 | 0.1879 | ND | ND | ND | ND |
| T111N | 9.21E−07 | 7.08E+04 | 6.52E−02 | 1.2377 | ND | ND | ND | ND |
| T41Y | 7.58E−08 | 2.71E+05 | 2.05E−02 | 0.2444 | ND | ND | ND | ND |
| Y45W | ND | ND | ND | ND | ND | ND | ND | ND |
| L72W | ND | ND | ND | ND | ND | ND | ND | ND |
| L72F | 3.32E−08 | 4.99E+05 | 1.66E−02 | 0.6366 | 3.57E−07 | 1.40E+06 | 5.02E−01 | 0.0168 |
| E68Q | 2.58E−08 | 3.00E+05 | 7.73E−03 | 0.9225 | ND | ND | ND | ND |
| P34F | 4.01E−08 | 4.81E+05 | 1.93E−02 | 0.3299 | ND | ND | ND | ND |
| P65R | 5.26E−08 | 4.34E+05 | 2.29E−02 | 0.5375 | ND | ND | ND | ND |
| P65E | 3.68E−08 | 5.65E+05 | 2.08E−02 | 0.041 | ND | ND | ND | ND |
| P65K | 9.08E−09 | 1.40E+05 | 1.27E−03 | 0.0233 | 1.25E−05 | 1.29E+05 | 1.62E+00 | 0.2343 |
| P65Q | 1.64E−08 | 4.56E+04 | 7.47E−04 | 0.2558 | ND | ND | ND | ND |
| E61W | 4.35E−06 | 2.57E+03 | 1.12E−02 | 0.0739 | ND | ND | ND | ND |
| T111H | 2.96E−08 | 5.80E+05 | 1.72E−02 | 0.3824 | ND | ND | ND | ND |
| F42M | 2.63E−08 | 8.34E+05 | 2.19E−02 | 0.105 | 2.28E−07 | 1.21E+06 | 2.76E−01 | 0.0146 |
| T37Y | 2.78E−08 | 5.54E+05 | 1.54E−02 | 0.4034 | 2.01E−07 | 1.55E+07 | 3.12E+00 | 0.0074 |
| K43W | ND | ND | ND | ND | ND | ND | ND | ND |
| T111M | 1.05E−08 | 6.31E+05 | 6.62E−03 | 0.1739 | 2.09E−06 | 3.76E+05 | 7.85E−01 | 0.0207 |
| E68F | 5.12E−08 | 6.36E+05 | 3.26E−02 | 0.3392 | ND | ND | ND | ND |
| T111Y | ND | ND | ND | ND | ND | ND | ND | ND |
| N71W | 7.19E−08 | 1.50E+05 | 1.08E−02 | 0.4301 | ND | ND | ND | ND |
| L72R | 1.31E−08 | 1.61E+05 | 2.11E−03 | 0.0829 | ND | ND | ND | ND |
| E68W | 3.03E−08 | 3.20E+05 | 9.70E−03 | 0.2677 | ND | ND | ND | ND |
| K35T | 3.94E−08 | 9.88E+05 | 3.89E−02 | 0.293 | 4.64E−07 | 6.69E+05 | 3.11E−01 | 0.0276 |
| E106W | 1.39E−07 | 8.33E+03 | 1.16E−03 | 0.616 | ND | ND | ND | ND |
| K48V | 1.18E−07 | 2.37E+04 | 2.78E−03 | 0.32 | ND | ND | ND | ND |
| P34Y | 3.04E−08 | 9.11E+04 | 2.77E−03 | 0.1383 | ND | ND | ND | ND |
| D109K | 1.36E−07 | 3.11E+05 | 4.23E−02 | 0.2363 | ND | ND | ND | ND |
| T111Q | 2.57E−08 | 1.37E+06 | 3.52E−02 | 0.1197 | 7.41E−08 | 4.86E+05 | 3.61E−02 | 0.0263 |
| D109M | 6.30E−08 | 1.34E+05 | 8.42E−03 | 0.1587 | ND | ND | ND | ND |
| E68L | 2.70E−08 | 3.97E+05 | 1.07E−02 | 0.4092 | 1.13E−04 | 5.22E+06 | 5.90E+02 | 0.8973 |
| T111S | 4.73E−08 | 6.10E+05 | 2.88E−02 | 0.4936 | 1.99E−07 | 4.07E+05 | 8.11E−02 | 0.0243 |
| E68R | 7.09E−08 | 2.47E+05 | 1.75E−02 | 0.0426 | 3.28E−06 | 7.51E+05 | 2.46E+00 | 0.0299 |
| K48S | 6.34E−08 | 4.12E+05 | 2.61E−02 | 0.3768 | 1.74E−06 | 5.81E+05 | 1.01E+00 | 0.0372 |
| K48H | ND | ND | ND | ND | ND | ND | ND | ND |
| P65N | 1.71E−08 | 4.63E+04 | 7.91E−04 | 0.3163 | 6.46E−06 | 1.08E+06 | 6.95E+00 | 0.1103 |
| E68Y | 5.95E−08 | 9.71E+05 | 5.78E−02 | 0.2917 | 2.13E−07 | 3.58E+05 | 7.63E−02 | 0.0273 |
| D109R | 4.32E−08 | 4.43E+05 | 1.91E−02 | 0.0917 | ND | ND | ND | ND |
| M104H | 4.53E−07 | 3.15E+03 | 1.43E−03 | 0.3194 | ND | ND | ND | ND |
| T41H | 1.14E−07 | 7.73E+05 | 8.83E−02 | 0.3765 | 5.09E−07 | 2.90E+05 | 1.48E−01 | 0.0294 |
| M104I | 7.62E−11 | 4.19E+03 | 3.20E−07 | 0.122 | ND | ND | ND | ND |
| K481 | ND | ND | ND | ND | ND | ND | ND | ND |
| S87E | 7.71E−07 | 9.09E+03 | 7.01E−03 | 0.5868 | ND | ND | ND | ND |
| WT | 4.12E−08 | 8.93E+05 | 3.68E−02 | 0.567 | 9.11E−07 | 5.47E+05 | 4.99E−01 | 0.0399 |

Figure 1B:
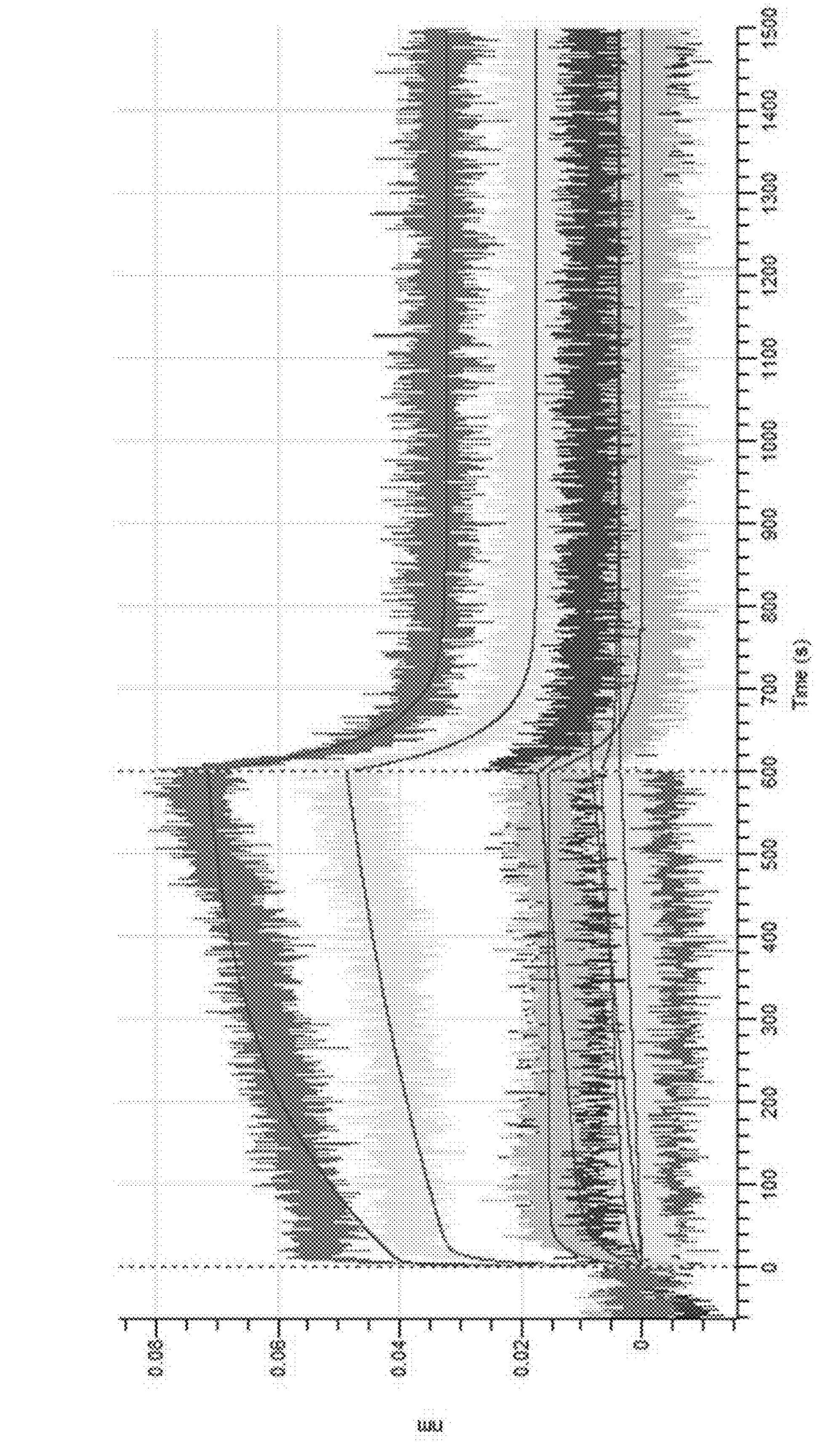
FIG. 1B shows that the IL-2 mutein K77A has similar binding affinity to IL-2Rα as WT IL-2.
Figure 1C:
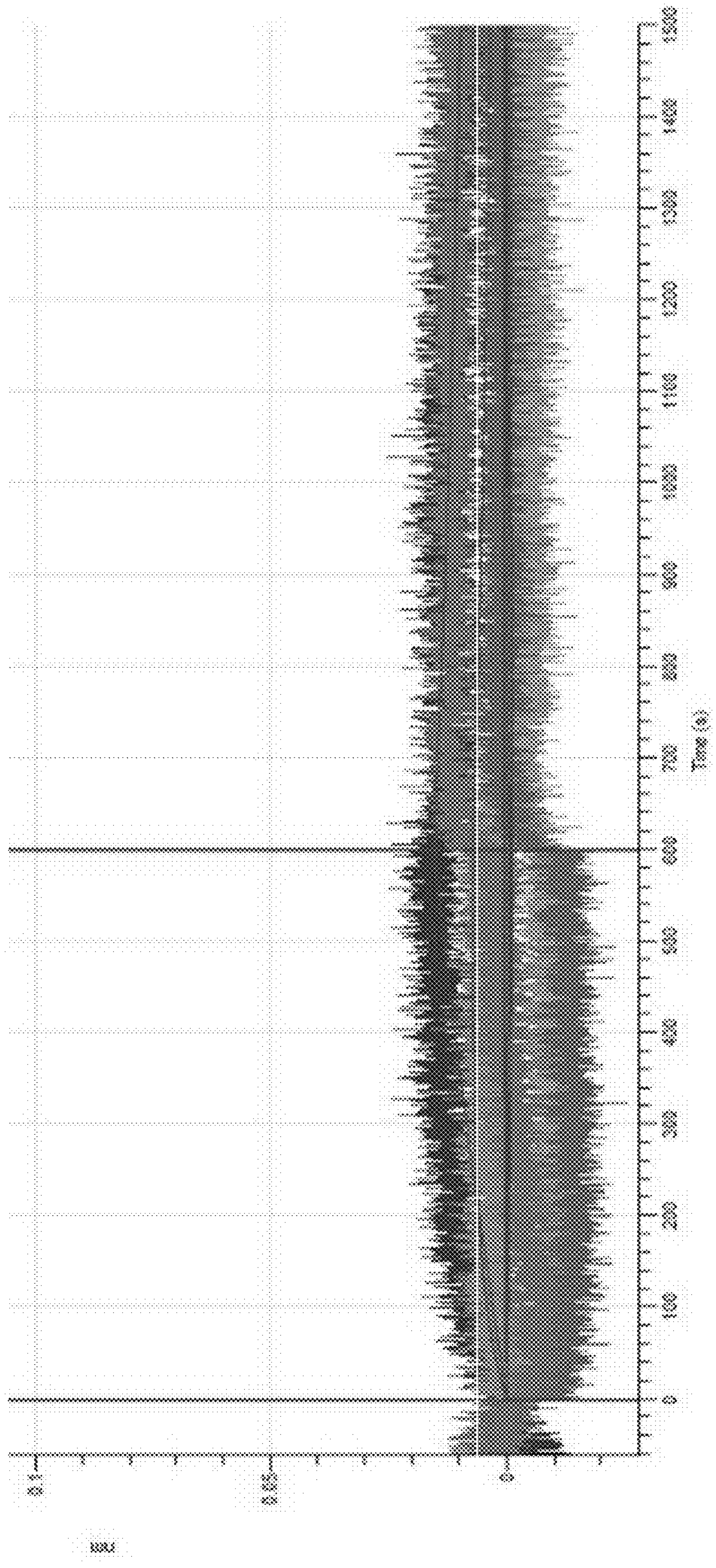
FIG. 1C shows that the E96A mutant does not bind IL-2Rα.

For example, the K77A IL-2 mutein exhibited binding affinity to IL-2Rα similar to WT IL-2 (FIG. 1A and FIG. 1B). In contrast, the mouse E96A mutant IL-2 showed reduced binding to IL-2Rα (CD25) (FIG. 1C).

This example illustrates the binding affinity of exemplary IL-2 muteins to IL-2 receptors.

Example 4. Induction of pSTAT5a in Human Peripheral Blood Cell Subsets

This example illustrates functional effects of exemplary IL-2 muteins on STAT5a phosphorylation in human CD4+ T cells and CD8+ T cells.

IL-2 binding to IL-2 receptor on the cell surface induces STAT5a phosphorylation, activating several signaling pathways resulting in the transcription of target genes that contribute to the various functions associated with the IL-2/IL-2R pathway. Therefore, in order to determine the integrated signaling response to IL-2 mediated by various combinations of the high and intermediate affinity receptors, pSTAT5a levels were measured within individual cells by flow cytometry.

The effects of single doses of IgG fusion IL-2 muteins (10 μM) on the induction ofSTAT5a phosphorylation were assessed in human CD4+ T cells and CD8+ T cells. Briefly, frozen PBMCs from a healthy human adult were incubated for 2 hours at 37° C. IgG fusion IL-2 mutein (10 pM) was added to 100 μl of PBMC at 0.5 million cells per well and incubated at 37° C. After 2 hours, the PBMCs were fixed and permeabilized using pre-warmed lysis/fixation buffer for 10 minutes at 37° C., washed 2× with PBS containing 0.2% BSA followed by permeabilization with −20° C. pre-cooled methanol for 20 minutes on ice. The cells were then extensively washed 4× with PBS containing 0.2% BSA before FACS staining was performed using a panel of fluorescent antibodies to distinguish CD4+ T cells, CD8+ T cells and the phosphorylation status of STAT5a in these cells. The antibodies utilized were anti-CD4-Alexa Fluor® 700 (clone RPA-T4), CD3-PerCP/Cy5.5 (UCHT1), CDS-Brilliant Violet 605 (RPA-T8), and pSTAT5a-Alexa Fluor® 488 (pY694) (BD®). Samples were acquired using an LSRFortessa cell analyzer (BD®) and data analyzed using FlowJo® software (Flow Jo, LLC). Intracellular pSTAT5a levels were quantified in 2 cell subsets and results are shown in CD4+ and CD8+ cells (Table 4).

TABLE 4 pSTAT5a levels in CD4+ and CD8+ T cells

| Mutation | CD4+ cells | CD8+ cells |
|---|---|---|
| V91I | 1.39E+00 | 1.05E+00 |
| V91L | 1.48E+00 | 1.12E+00 |
| V91W | 1.07E+00 | 1.05E+00 |
| E95Q | 1.56E+00 | 1.05E+00 |
| E95S | 1.47E+00 | 1.00E+00 |
| E95N | 9.81E−01 | 1.05E+00 |
| L12Y | 1.30E+00 | 1.01E+00 |
| L19V | 1.31E+00 | 9.53E−01 |
| D84E | 1.61E+00 | 9.57E−01 |
| L19F | 1.49E+00 | 1.06E+00 |
| E95D | 1.62E+00 | 1.02E+00 |
| I92Y | 1.94E+00 | 1.12E+00 |
| E95T | 1.64E+00 | 1.02E+00 |
| I92V | 9.81E−01 | 1.075539568 |
| L12V | 1.64E+00 | 1.03E+00 |
| I92W | 1.11E+00 | 9.86E−01 |
| D84T | 1.21E+00 | 9.60E−01 |
| D84S | 1.20E+00 | 1.05E+00 |

TABLE 4-continued pSTAT5a levels in CD4+ and CD8+ T cells

| Mutation | CD4+ cells | CD8+ cells |
|---|---|---|
| M23L | 1.91E+00 | 1.05E+00 |
| I92F | 1.77E+00 | 1.20E+00 |
| M23I | 1.83E+00 | 1.16E+00 |
| H16Y | 1.75E+00 | 1.21E+00 |
| E15D | 1.09E+00 | 1.01E+00 |
| L12I | 2.35E+00 | 1.59E+00 |
| E15S | 1.66E+00 | 9.32E−01 |
| D20N | 2.23E+00 | 1.50E+00 |
| H16R | 1.40E+00 | 1.63E+00 |
| E15T | 3.06E+00 | 1.79E+00 |
| D20T | 1.46E+00 | 1.70E+00 |
| N88S | 1.20E+00 | 1.04E+00 |
| S87T | 2.00E+00 | 1.07E+00 |
| V91F | 1.37E+00 | 1.04E+00 |
| V91M | 1.42E+00 | 1.05E+00 |
| H16K | 1.05E+00 | 1.09E+00 |
| L19I | 2.22E+00 | 1.04E+00 |
| T111W | 1.58E+00 | 1.15E+00 |
| D109H | 1.01E+00 | 1.10E+00 |
| P34W | 1.89E+00 | 1.10E+00 |
| D109W | 1.53E+00 | 1.05E+00 |
| T111N | 1.64E+00 | 1.08E+00 |
| T41Y | 1.53E+00 | 1.00E+00 |
| L72F | 1.65E+00 | 9.39E−01 |
| E68Q | 2.00E+00 | 1.40E+00 |
| P34F | 2.85E+00 | 1.88E+00 |
| P65R | 1.67E+00 | 1.15E+00 |
| P65E | 1.51E+00 | 1.05E+00 |
| P65K | 1.59E+00 | 1.31E+00 |
| P65Q | 1.60E+00 | 1.13E+00 |
| E61W | 1.30E+00 | 1.18E+00 |
| T111H | 1.90E+00 | 1.14E+00 |
| F42M | 1.98E+00 | 1.18E+00 |
| T37Y | 2.70E+00 | 1.67E+00 |
| K43W | 1.24E+00 | 1.16E+00 |
| T111M | 1.74E+00 | 1.23E+00 |
| E68F | 2.19E+00 | 9.46E−01 |
| N71W | 1.58E+00 | 1.02E+00 |
| L72R | 1.60E+00 | 9.30E−01 |
| E68W | 1.96E+00 | 9.97E−01 |
| K35T | 2.39E+00 | 1.19E+00 |
| E106W | 1.02E+00 | 1.18E+00 |
| K48V | 1.12E+00 | 1.18E+00 |
| P34Y | 1.11E+00 | 1.29E+00 |
| D109K | 1.77E+00 | 1.32E+00 |
| T111Q | 2.10E+00 | 1.28E+00 |
| D109M | 1.28E+00 | 9.06E−01 |
| E68L | 2.01E+00 | 1.16E+00 |
| T111S | 2.47E+00 | 1.24E+00 |
| E68R | 2.36E+00 | 1.22E+00 |
| K48S | 2.23E+00 | 1.16E+00 |
| P65N | 1.71E+00 | 1.07E+00 |
| E68Y | 2.60E+00 | 1.28E+00 |
| D109R | 1.77E+00 | 1.27E+00 |
| M104H | 1.01E+00 | 9.89E−01 |
| T41H | 1.19E+00 | 8.48E−01 |
| M104I | 1.25E+00 | 8.51E−01 |
| K48I | 9.44E−01 | 8.68E−01 |
| S87E | 1.00E+00 | 8.25E−01 |

Based on the results of affinity measurement to IL-2 receptors and induction of pSTAT5a in human PBMC, 6 clones were selected for further analysis (M23L, E15T, P34F, T111H, T37Y and E68F).

A dose response analysis of selected muteins in pSTAT5a assay was performed.

Briefly, frozen PBMCs from a healthy human adult was incubated for 2 hours at 37° C. Various concentrations (10 nM to 0.01 pM) of IgG fusion IL-2 muteins were added to 100 μl of PBMC at 0.5 million cells per well and incubated at 37° C. After 2 hours, the PBMCs were fixed and pSTAT5a level was measured as mentioned previously.

The results showed that all 6 muteins tested showed pSTAT5a induction activity in CD4+ cells that was equivalent to or greater than induction by wild type IL-2.

Figure 2A:
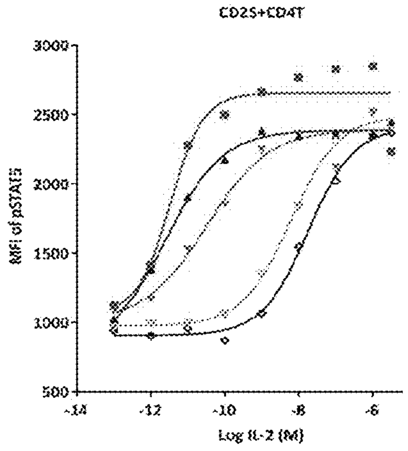
FIG. 2A is a graph showing median fluorescent intensity to quantify pSTAT5 induction in CD25+CD4T cells.
Figure 2B:
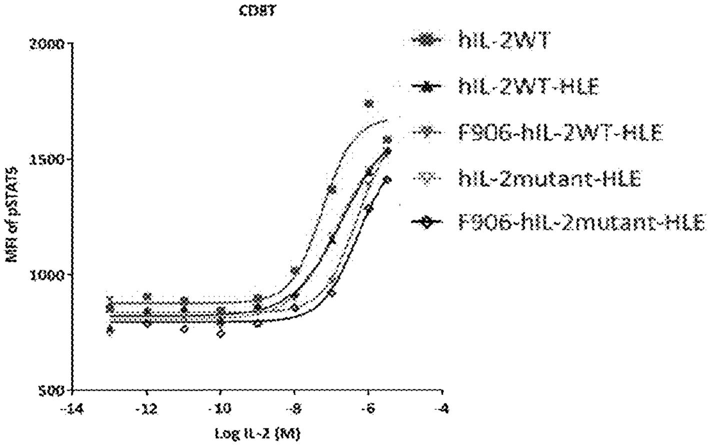
FIG. 2B shows a graph of pSTAT5 levels in CD8T cells.
Figure 2C:
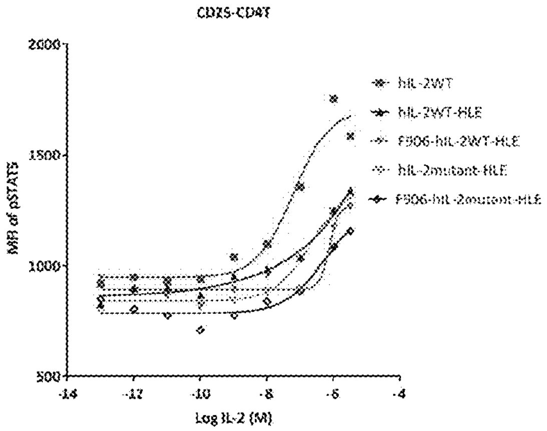
FIG. 2C shows a graph of pSTAT5 levels in CD25-CD4T cells.
Figure 2D:
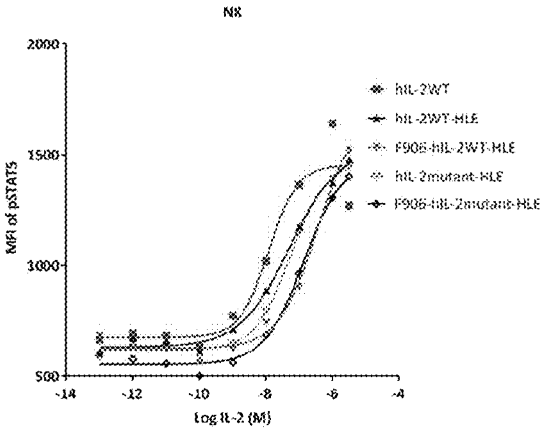
FIG. 2D shows a graph of pSTAT5 levels in CD25-NK cells.

Further, the exemplary E62A mutation inhibited human IL-2 mutant activity to induce pSTAT5 in CD25+ CD4 T cells, but not in CD8 T cells (FIG. 2A and FIG. 2B, Table 5). The E62A mutation did not inhibit human IL-2 mutant activity to induce pSTAT5 in CD25-CD4 T cells and in NK cells (FIG. 2C and FIG. 2D). F906 is a VH domain of an anti-CTLA-4 antibody. Wild-type human IL-2 or human IL-2 mutein coupled with F906 via a peptide linker is specifically delivered to Treg.

TABLE 5

Comparison of pSTAT5 EC50 (M) in CD25 + CD4T cells and CD8T cells

| Drug | EC50 (M) in CD25 + CD4T | EC50 (M) in CD8T |
|---|---|---|
| hIL-2 WT | 3.39E−12 | 5.53E−08 |
| hIL-2 WT + HLE | 2.54E−12 | 1.93E−07 |
| hIL-2 mutant + HLE | 6.06E−09 | 1.37E−07 |
| F906 + hIL-2 WT + HLE | 3.29E−11 | 4.73E−07 |
| F906 + hIL-2 mutant + HLE | 1.79E−08 | 4.88E−07 |

Figure 2E:
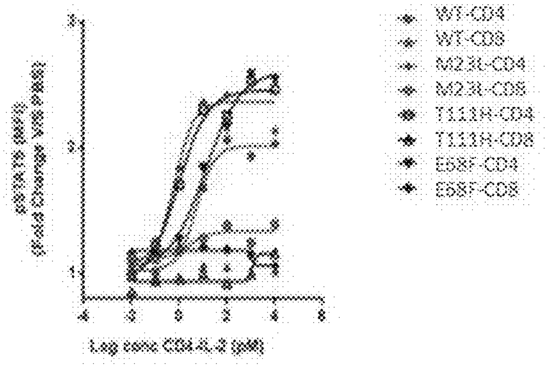
FIG. 2E depicts a series or graphs and associated tables that show pSTAT5a induction using IL-2 muteins M23L, T111H, E68F, E15T, P34F, T37Y in comparison to wild-type IL-2.
Figure 2E:
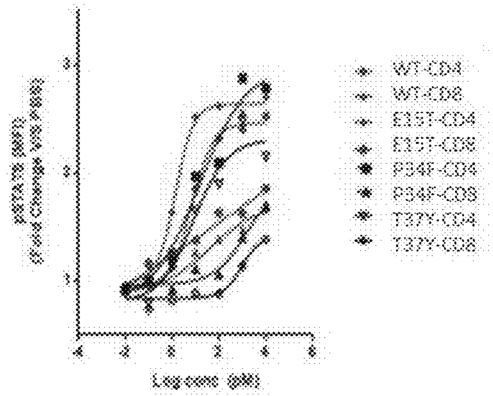
Figure 3:
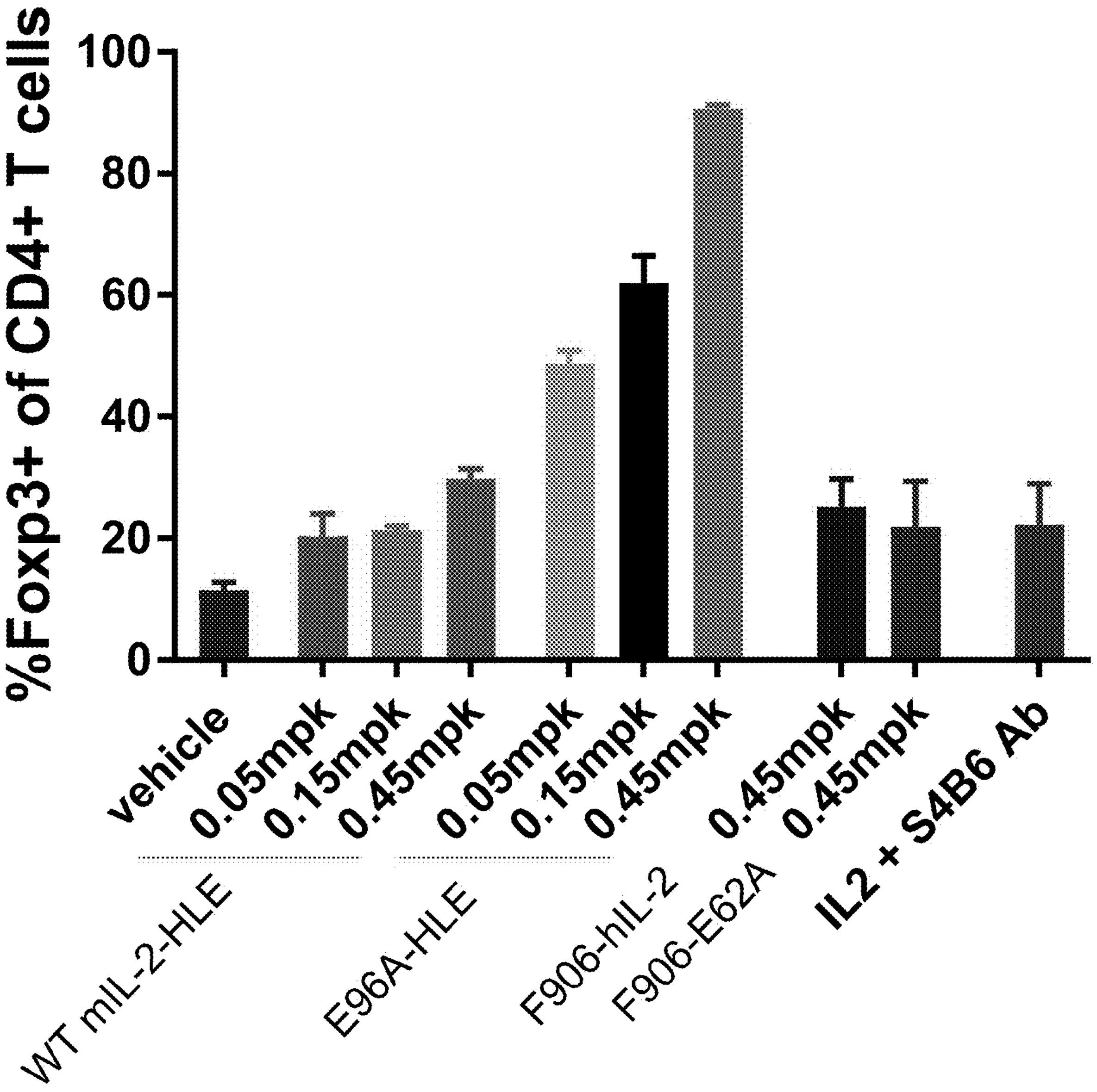
FIG. 3 is a graph showing a comparison of the dose-dependent increase in the number of Treg cells (% foxp3+ of CD4+ T cells) upon treatment with E96-HLE in comparison with WT mIL-2-HLE, F906-hIL2, F906-E62A and IL-2-S4B6 antibody.
Figure 4A:
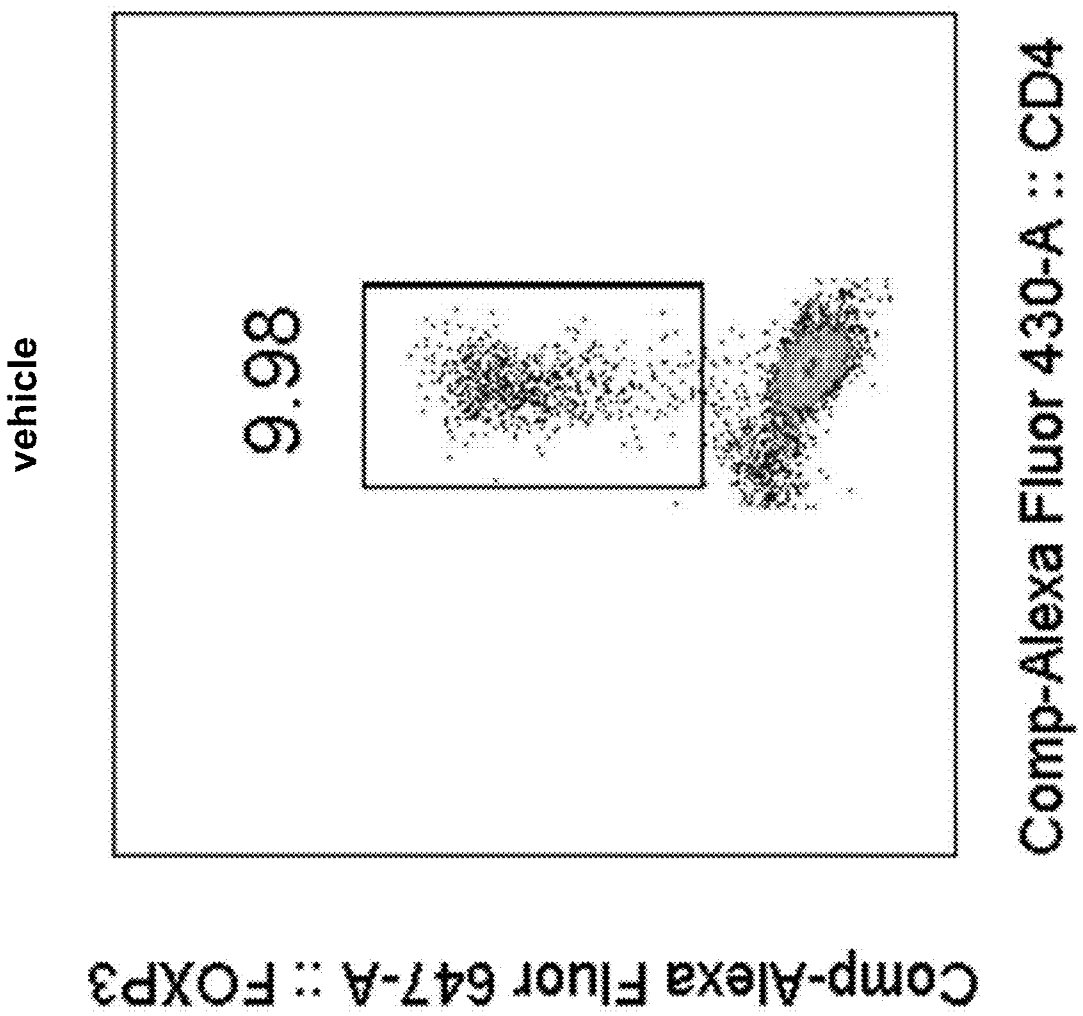
FIG. 4A shows representative Treg population in vehicle-treated cells measured by flow cytometry, graphed in FIG. 3.
Figure 4B:
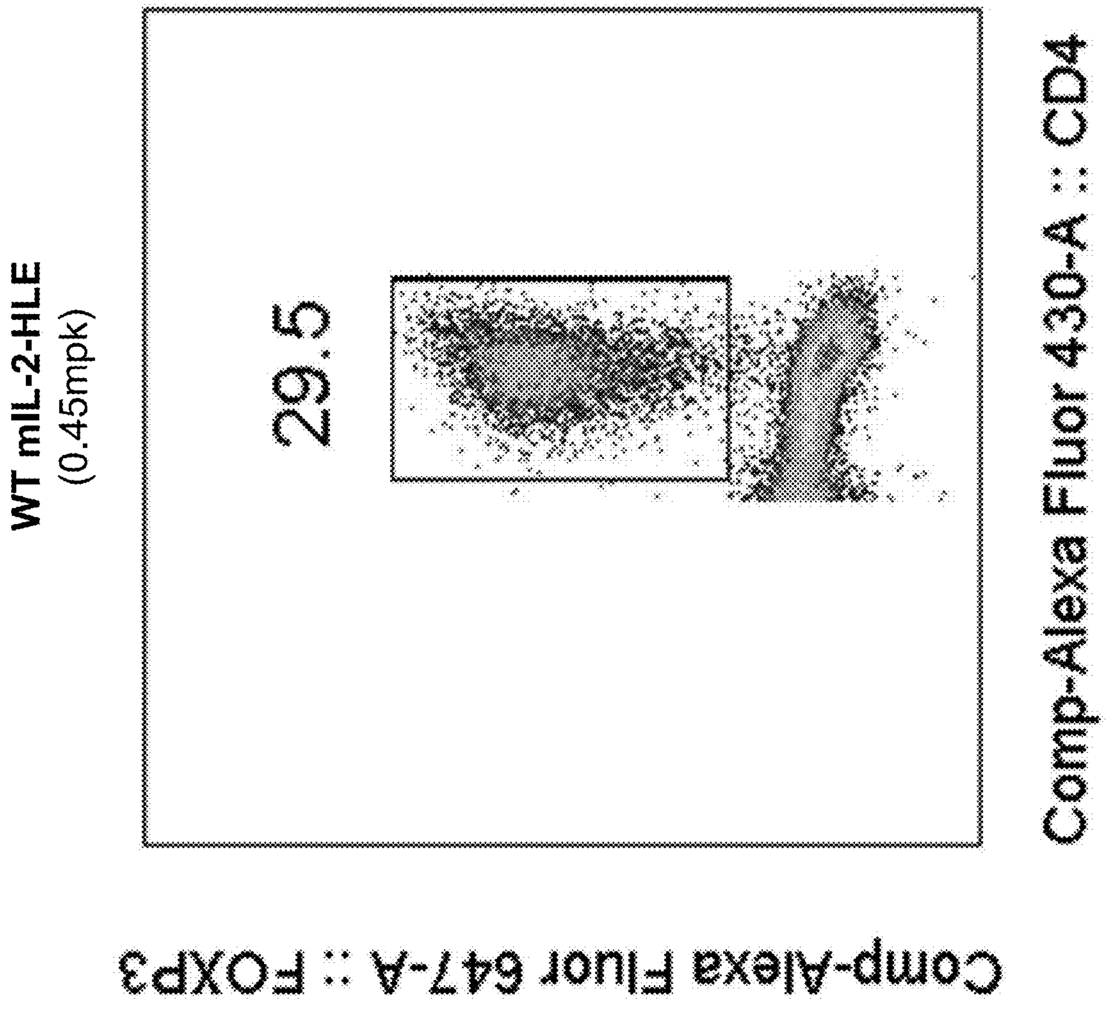
FIG. 4B shows exemplary Treg population in WT mIL-2 HLE cells.
Figure 4C:
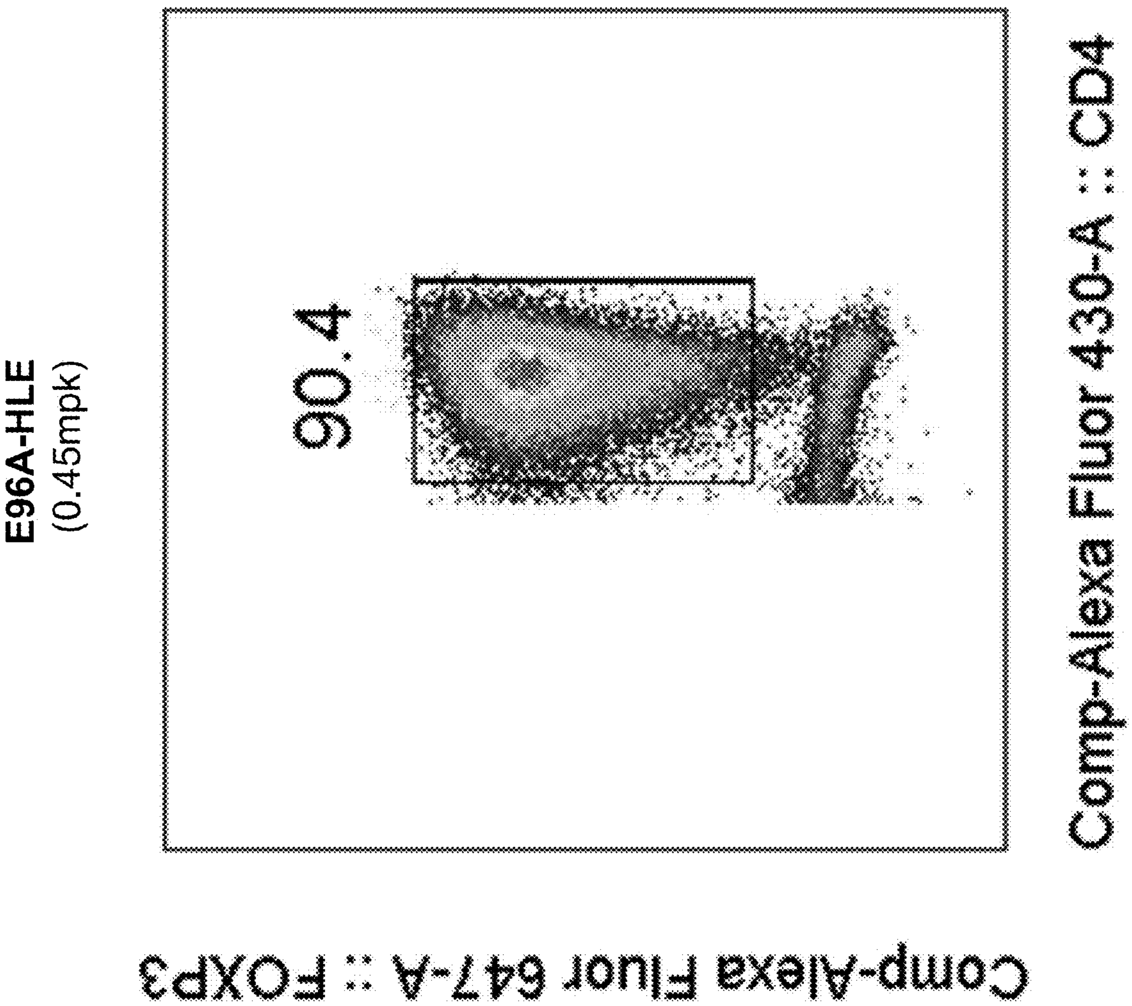
FIG. 4C, FIG. 4D and FIG. 4E show a dose-dependent increase in exemplary Treg populations with E96-HLE.
Figure 4D:
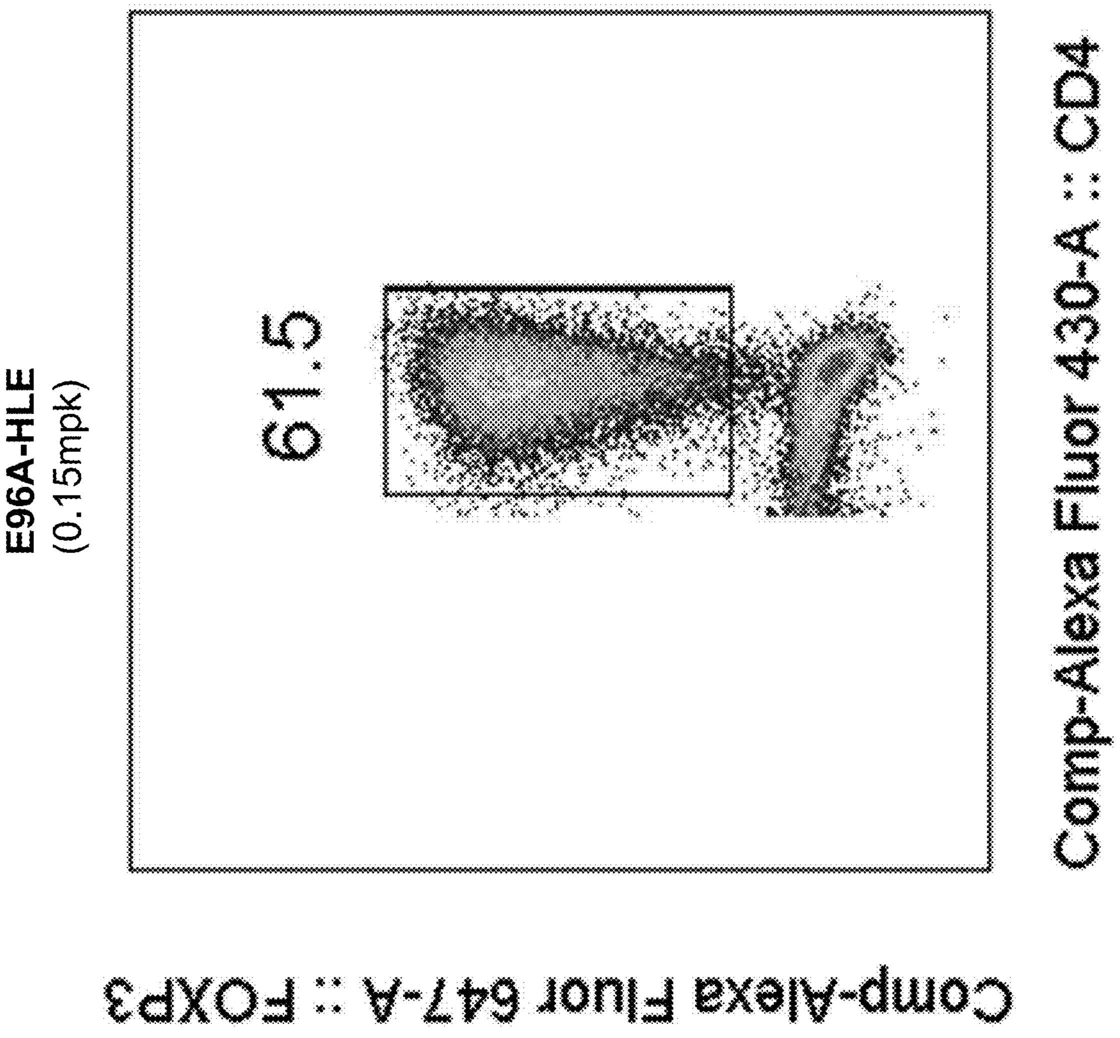
Figure 4E:
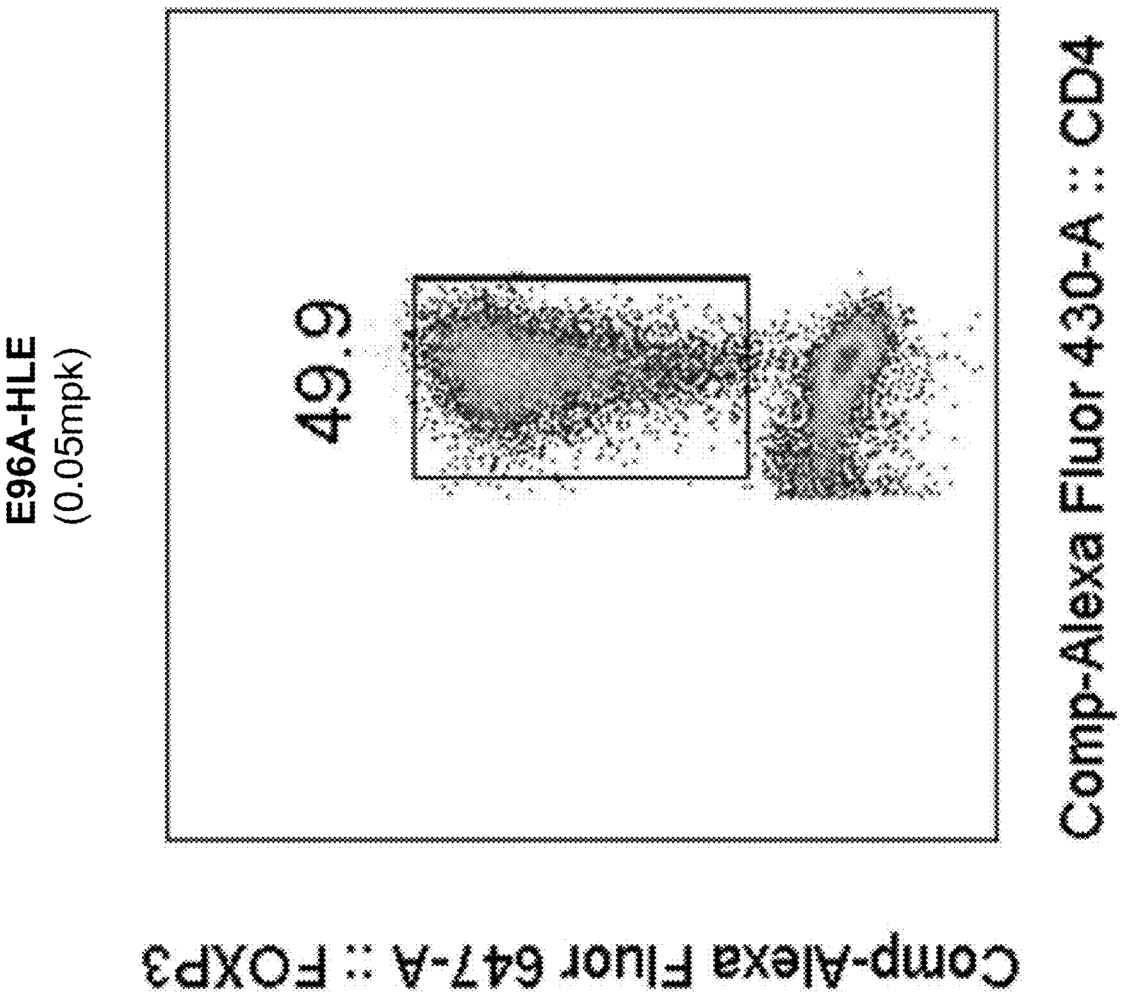
Figure 4F:
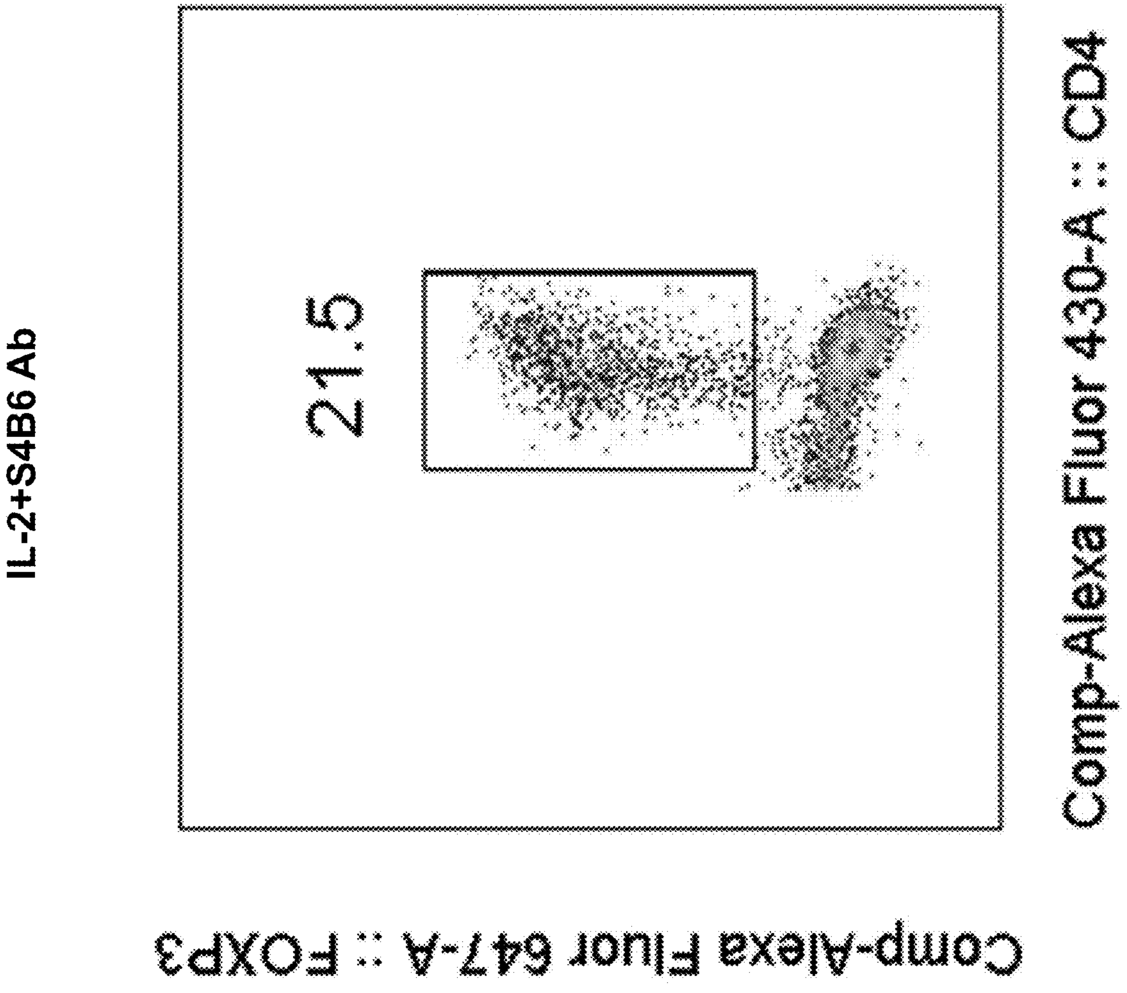
FIG. 4F shows representative control flow cytometry results with IL2+SB46 antibody.

FIG. 2E depicts a series of graphs that show pSTAT5a induction and a table with related EC50 and Emax values using IL-2 muteins M23L, T111H, E68F, E15T, P34F, T37Y in comparison to wild-type IL-2.

This example illustrates exemplary pSTAT5a induction by IL-2 muteins.

Example 5. Effects of E96A-HLE in WT Mice after Multiple Doses

This example illustrates in vivo effects exemplary E96A-HLE mutein in mice after administration of multiple doses.

To understand the biological activity of E96A-HLE compared to WT mIL-2-HLE (wild-type mouse IL-2-half-life extended), mice were treated with these cytokines. CD8 and CD4 T cells, including Tregs, were examined for changes in growth of immune cell subsets.

Each of the biologics was diluted in 1×PBS. For each condition, mice received 100 μL volume, intraperitoneally, based on an estimate of 20 g/mouse. Non tumor-bearing female C57BL/6 mice at 6-8 weeks of age were treated daily for 5 days, rested for 2 days, then treated again for 4 days. At 24 hrs after the final dose, mice were euthanized and spleens were isolated for PD analysis. Three mice were tested in each group.

Spleens were mashed through a 70 μm cell strainer in RP10. Cells were RBC lysed with RBC lysis buffer and viable splenocytes were counted by ViCell (Beckman Coulter). Spleens were stained by live/dead e780, anti-CD3, anti-CD4, anti-CD8, anti-CD25, and anti-foxp3 antibodies according to manufacturer's instructions. Splenocytes were washed and incubated with antibody in stain buffer, and intracellular staining was performed using foxp3 staining buffer set. Cells were analyzed on an LSRFortessa FACS machine (BD) and data were analyzed using FloJo software (TreeStar).

Lymphocytes were gated based on FSC/SSC and doublets were excluded. Naive T cells were identified as CD3+CD4+ foxp3+ (FIG. 4).

The results showed that treatment of mice with WT mIL-2-HLE resulted in some expansion of CD4+foxp3+ T cells while E96A-HLE resulted in a greater dose-dependent expansion of CD4+foxp3+ T cells (FIG. 3 and FIG. 4A-FIG. 4F).

Figure 5A:
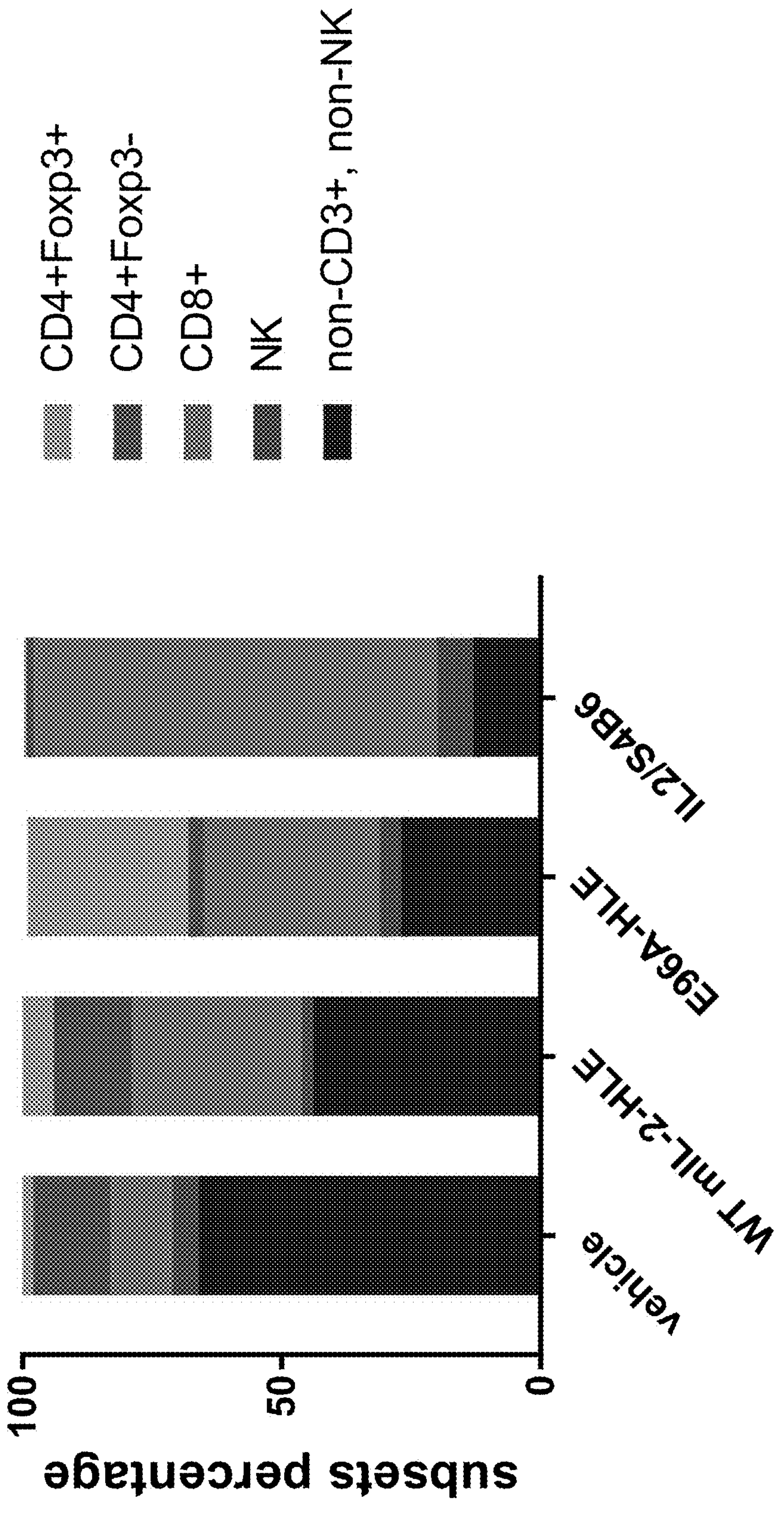
FIG. 5A is a graph that shows a comparison of dose-dependent expansion of the percentage of foxp3+ cells as a subset of CD3+ cells in E96-HLE treatment of mice relative to WT mIL-2-HLE.

Treatment of mice with WT mIL-2-HLE resulted in expansion of foxp3+ cells as a subset of CD3+ cells while treatment of mice with E96A-HLE resulted in a greater dose-dependent expansion of the percentage of foxp3+ cells as a subset of CD3+ cells (FIG. 5A).

Figure 5B:
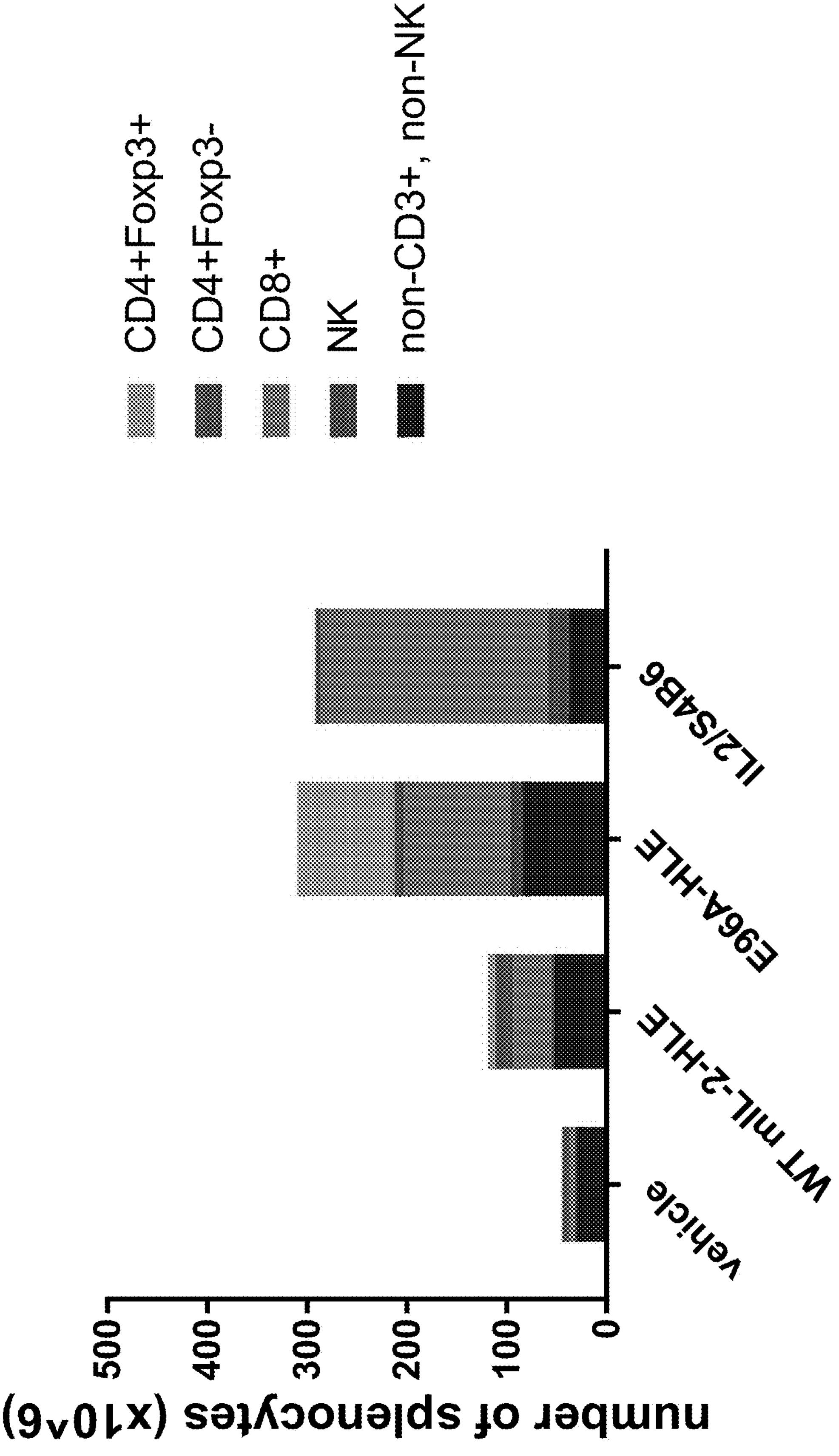
FIG. 5B is a graph that shows a comparison of dose-dependent expansion of splenocytes, including CD3+ cells in E96-HLE treated mice relative to WT mIL-2-HLE.

The treatment of mice with E96A-HLE resulted in a dose-dependent expansion of splenocytes, including CD3+ cells. (FIG. 5B).

The results showed in vivo activity of IL-2-HLE and dose-dependent increase in Tregs with administration of E96A-HLE.

Example 6. Effects of E62A-HLE and E96A-HLE in WT Mice after Single Administration This example illustrates the in vivo effects of E62A-HLE and E96A-HLE compared to WT hIL2-HLE and WT mIL2-HLE after a single dose administration.

Figure 6A:
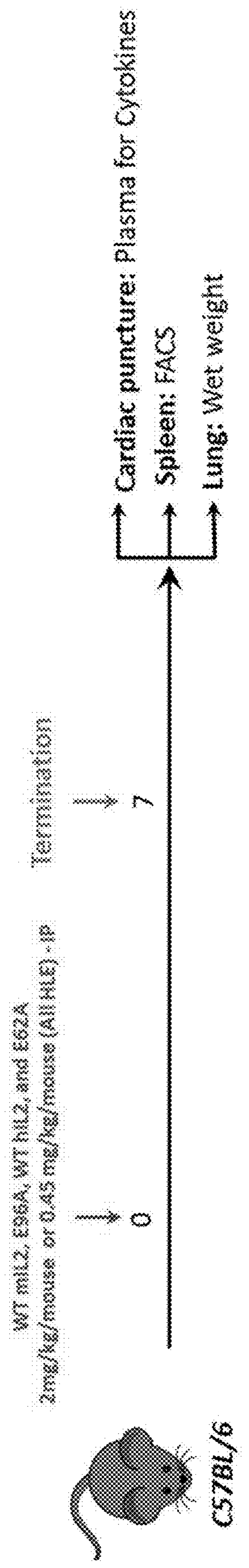
FIG. 6A is a schematic that shows the experimental design for testing the effects of E62A-HLE and E96A-HLE in WT mice after a single round of administration.

To understand the biological activity of E62A-HLE and E96A-HLE compared to WT hIL2-HLE (wild-type human IL-2-half-life extended) and WT mIL-2-HLE, mice were treated with these cytokines. CD8 and CD4 T cells, including Tregs, were examined for changes in growth of immune cell subsets. Each of the biologics was diluted in 1×PBS. For each biologic, mice received 100 μL volume, intraperitoneally, based on an estimate of 20g/mouse (FIG. 6A).

For each group, four non-tumor bearing female C57BL/6, 6-8 weeks of age, were administered a single treatment of mouse or human WT IL2 or IL2 mutein at either a low dose (0.45 mg/kg/mouse) or a high dose (2 mg/kg/mouse) and 7 days later, mice were euthanized. Wet weight of lungs was measured, cardiac puncture was obtained for plasma cytokine analysis and spleens were isolated for PD analysis.

Figure 6B:
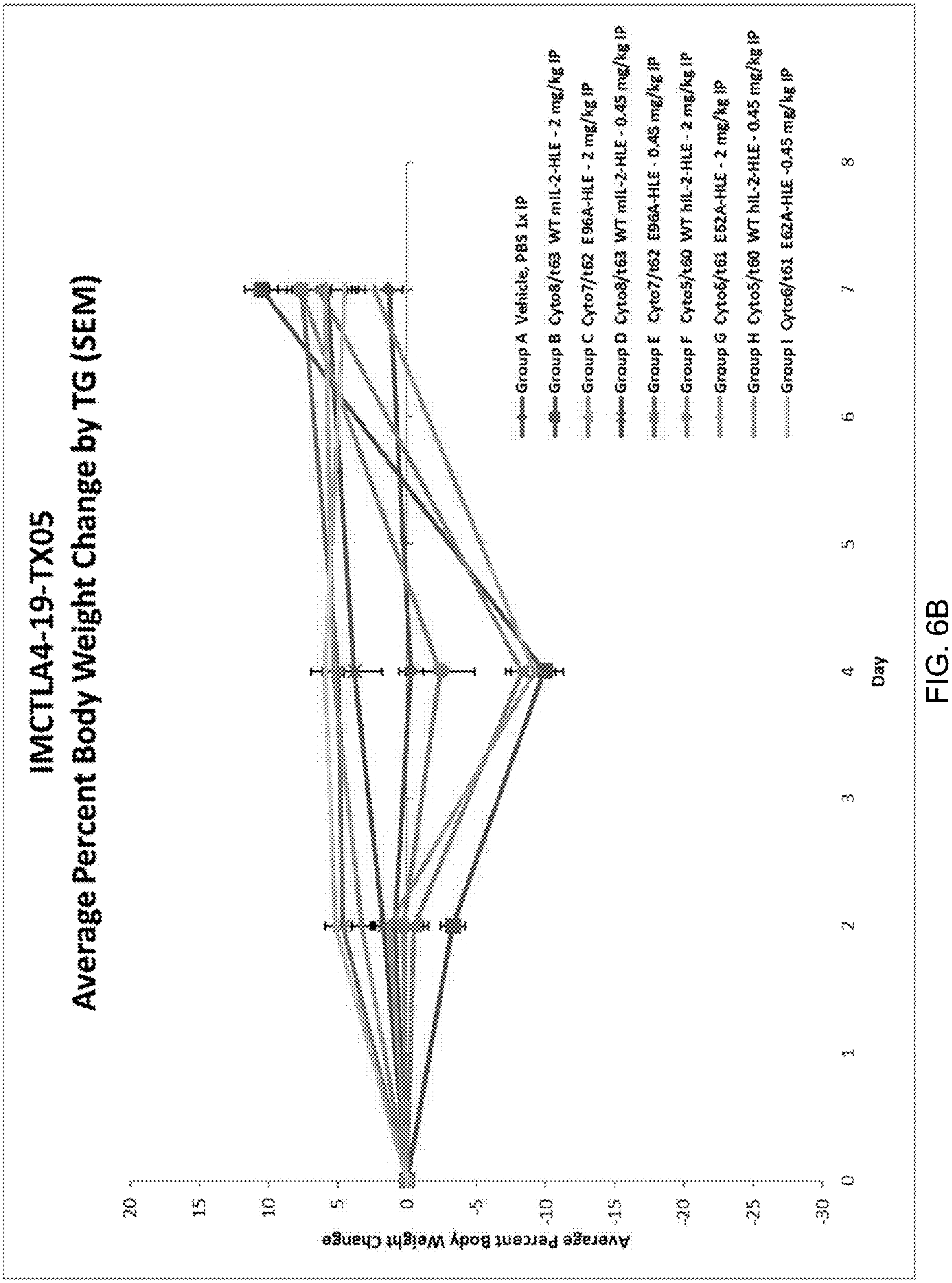
FIG. 6B is average percent body weight in mice administered with IL-2 muteins E62A-HLE and E96A-HLE relative to WT mice.

The average percent body weight change was measured by thermogravity (TG) (FIG. 6B).

Spleens were mashed through a 70 μm cell strainer in RP10. Cells were RBC lysed with RBC lysis buffer and viable splenocytes were counted by ViCell. Spleens were stained by live/dead e780, anti-CD3, anti-CD4, anti-CD8, anti-CD25, and anti-foxp3, all stained according to manufacturer's instructions. Splenocytes were washed and incubated with antibody in stain buffer, and intracellular staining was performed using foxp3 staining buffer set. Cells were analyzed on an LSRFortessa FACS machine and data were analyzed using FloJo software. Lymphocytes were gated based on FSC/SSC and doublets were excluded. Naive T cells were identified as CD3+CD4+foxp3+.

Figure 6C:
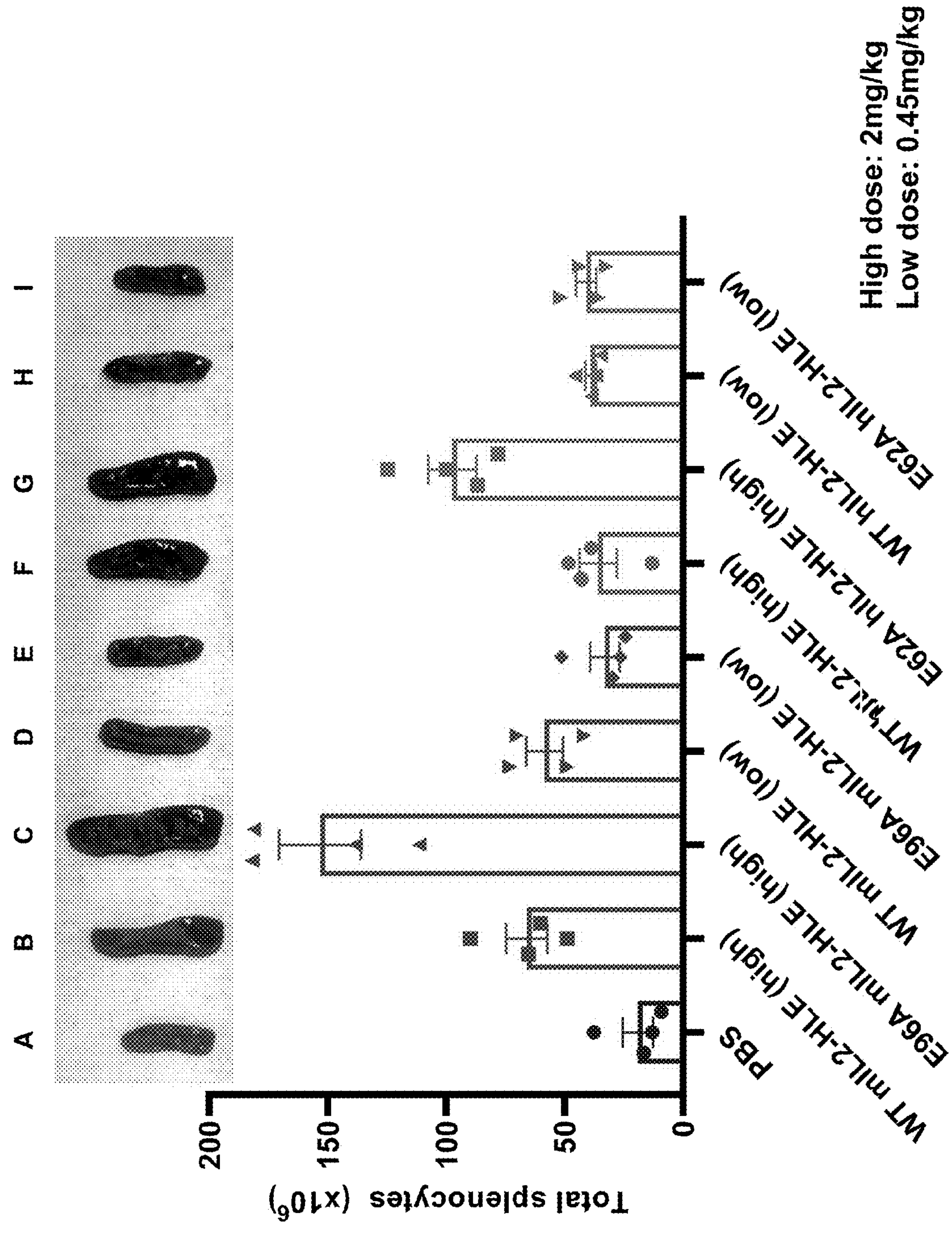
FIG. 6C is a graph scoring the total number of splenocytes upon treatment of mice with E62A-HLE or with E96A-HLE relative to WT mIL-2-HLE or WT hIL2-HLE at a low dose as well as a high dose administration.
Figure 8A:
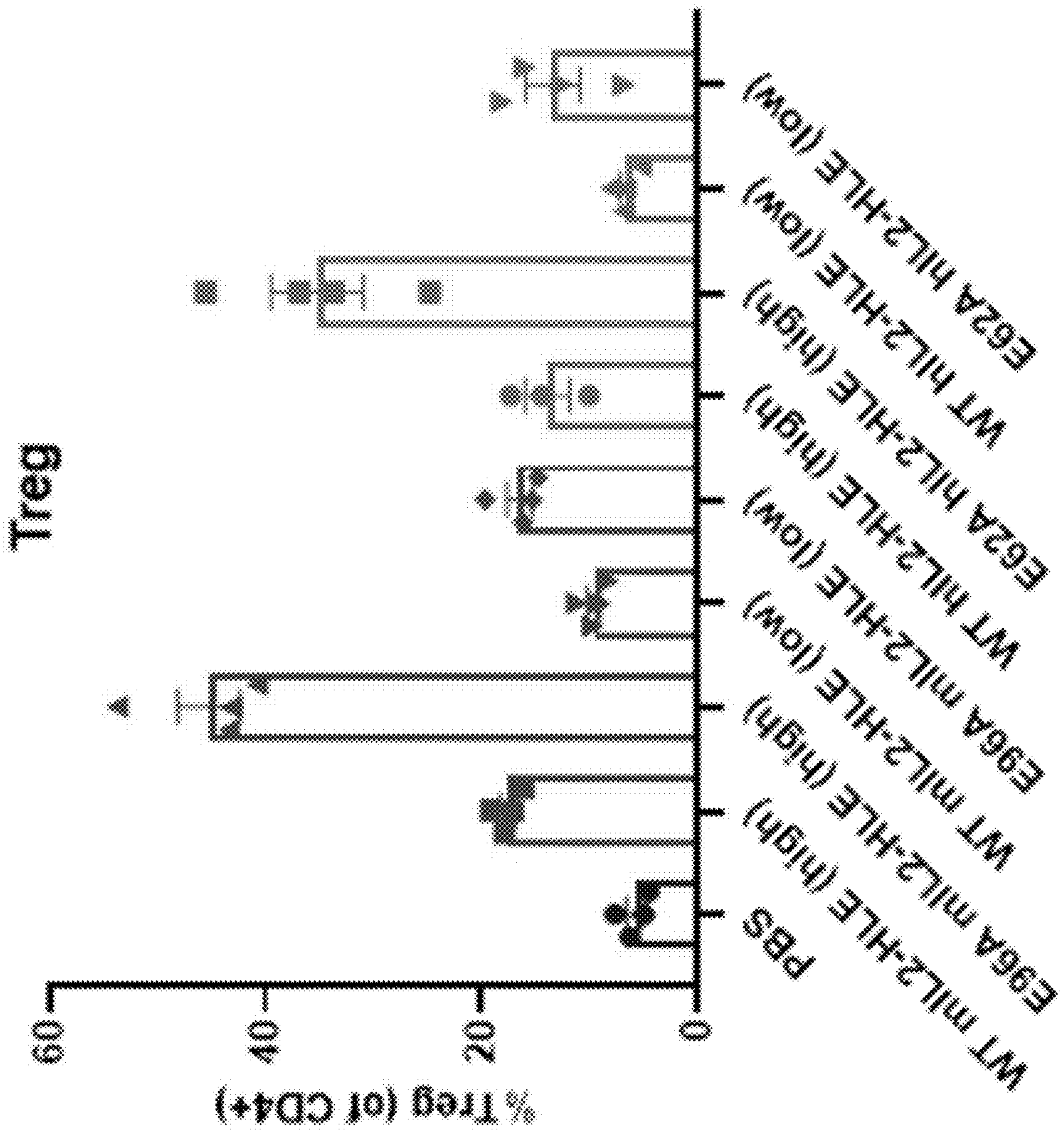
FIG. 8A and FIG. 8D are graphs that show percent Treg cells as a proportion of CD4+ cells following treatment of mice with WT or IL-2 E62A-HLE or E96A-HLE muteins.
Figure 8B:
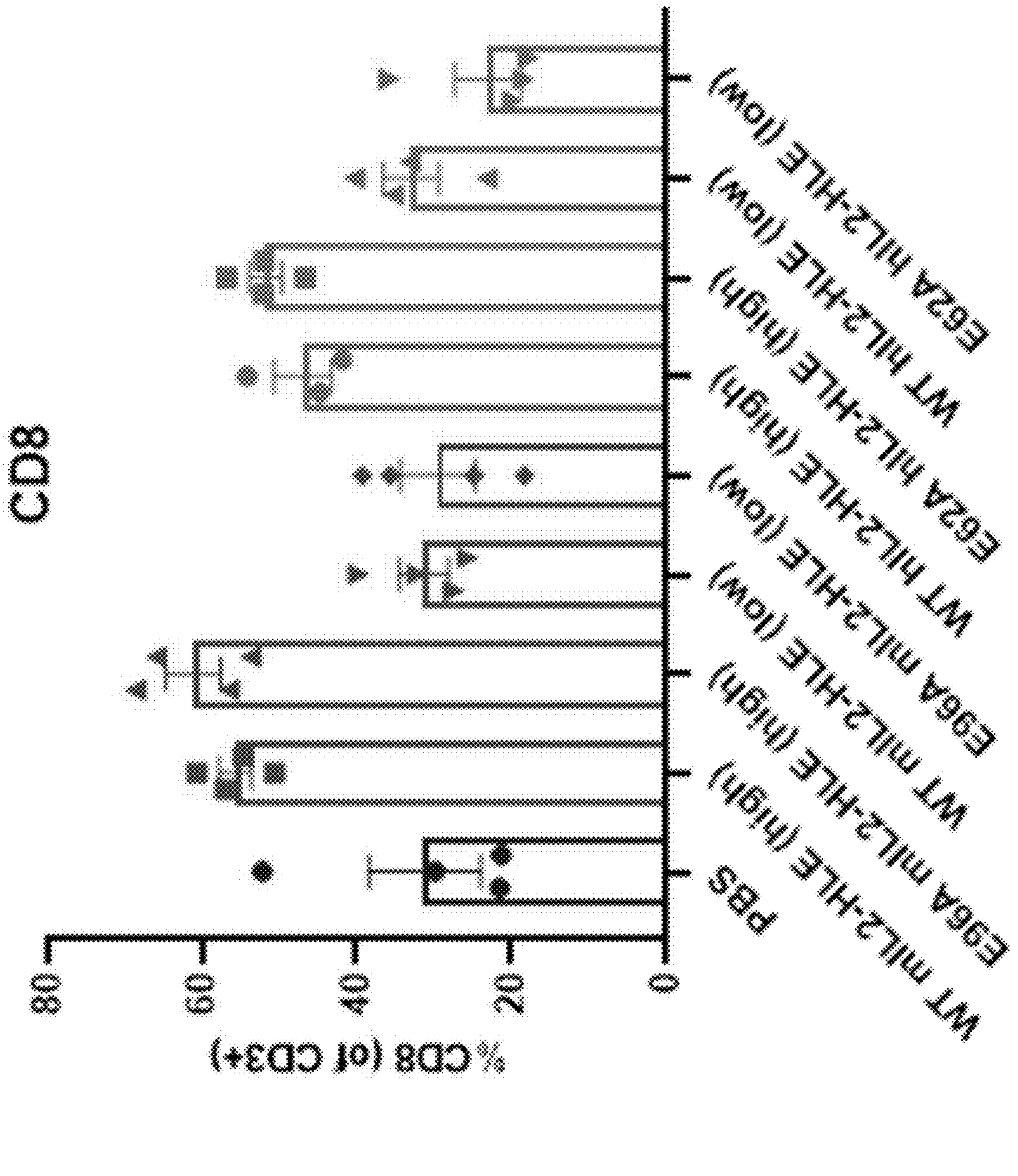
FIG. 8B and FIG. 8E are graphs that shows percent CD8+ cells as a proportion of CD3+ cells following treatment of mice with WT or IL-2 E62A-HLE or E96A-HLE muteins.
Figure 8C:
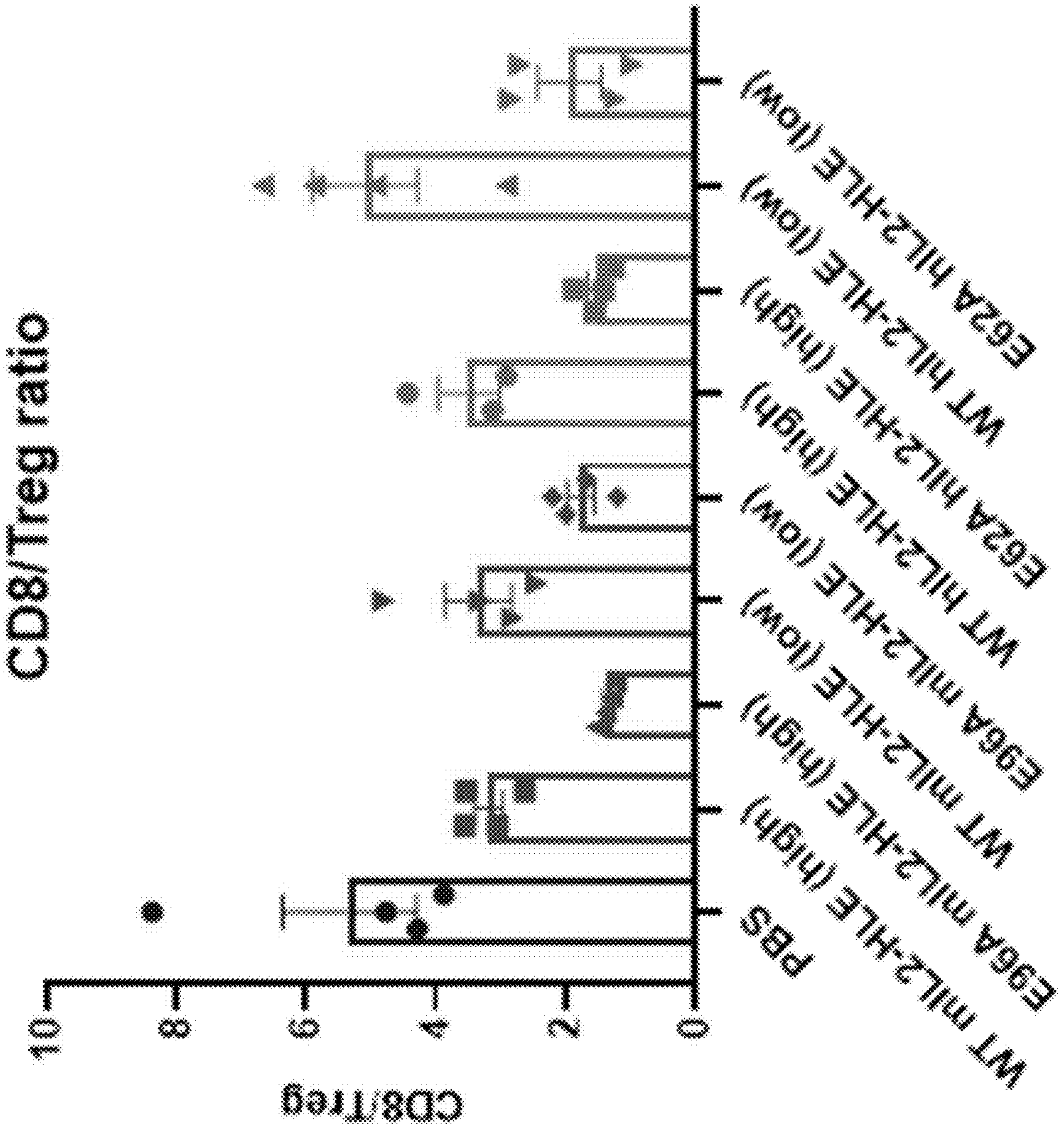
FIG. 8C and FIG. 8F are graphs that show the ratio of CD8:Tregs comparing treatment of mice with E62A-HLE or E96A-HLE with WT IL-2.

Treatment of mice with WT mIL-2-HLE or WT hIL2-HLE resulted in an increase in the number of splenocytes while treatment of mice with E62A-HLE or with E96A-HLE resulted in a greater dose-dependent expansion of splenocytes (FIG. 6C). Treatment of mice with E96A-HLE or with E62A-HLE resulted in a dose-dependent expansion of CD4+ foxp3+ T cells. Treatment of mice with WT hIL2-HLE or WT mIL-2-HLE resulted in a decrease in the ratio of CD8:Tregs, while treatment of mice with E62A-HLE or with E96A-HLE resulted in a greater decrease in the ratio of CD8:Tregs as a result of the preferential expansion of Tregs (FIG. 8A-FIG. 8C).

Example 7. Effects of E62A-HLE and E96A-HLE in WT Mice after Two Doses

This example illustrates the in vivo effects of E62A-HLE and E96A-HLE compared to WT hIL2-HLE and WT mIL2-HLE after a two dose administration.

Figure 7A:
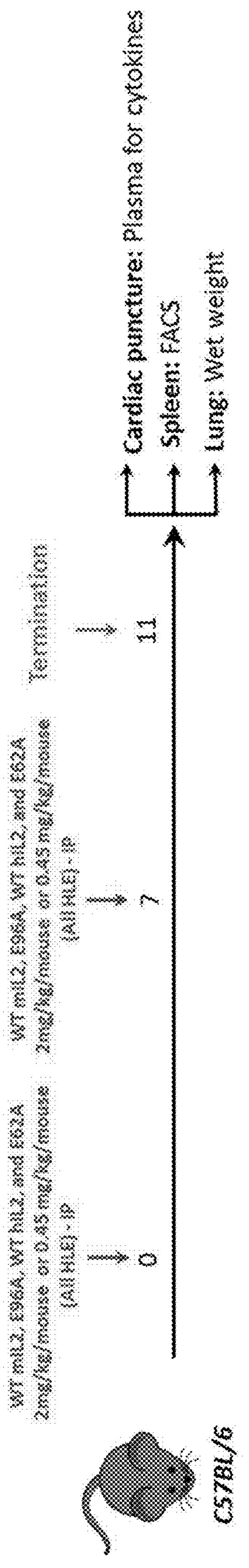
FIG. 7A is a schematic that shows the experimental design for testing the effects of E62A-HLE and E96A-HLE in WT mice after two rounds of administration.

To understand the biological activity of E62A-HLE and E96A-HLE compared to WT hIL2-HLE and WT mIL-2-HLE, mice were treated with these cytokines. CD8 and CD4 T cells, including Tregs, were examined for changes in growth of immune cell subsets. Each of the biologics was diluted in 1×PBS. For each biologic, mice received 100 μL volume, intraperitoneally, based on an estimate of 20g/mouse (FIG. 7A).

For each group, four non-tumor bearing female C57BL/6, 6-8 weeks of age, were administered a single treatment day 0 at either a low dose of 0.45 mg/kg/mouse or a high dose of 2 mg/kg/mouse, then again 7 days later, then 4 days later were euthanized. Wet weight of lungs was measured, cardiac puncture was obtained for plasma cytokine analysis and spleens were isolated for PD analysis.

Figure 7B:
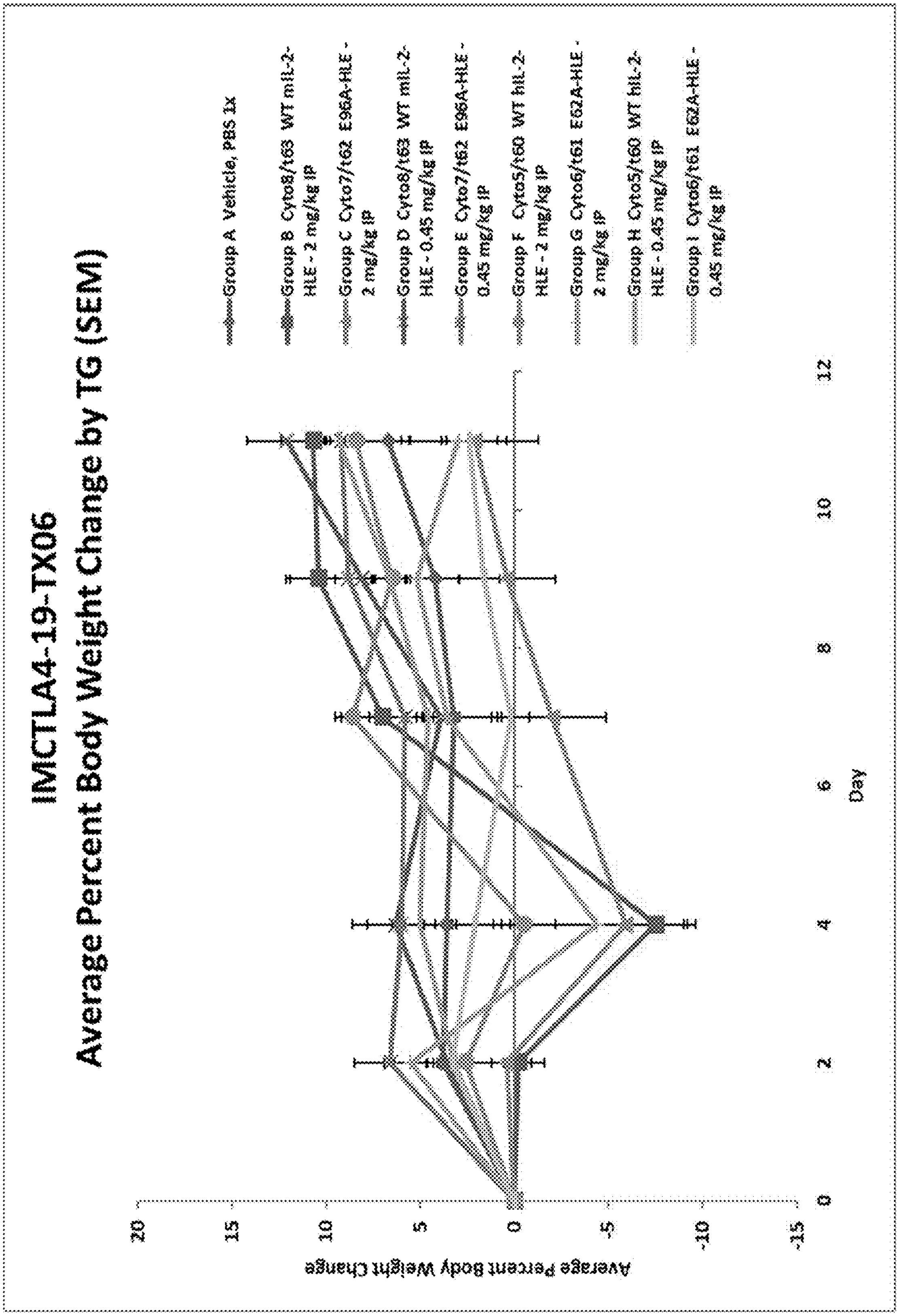
FIG. 7B is a graph that shows average percent body weight in mice administered with two rounds of IL-2 muteins E62A-HLE and E96A-HLE relative to WT mice.

Administration of high dose WT or mutant IL-2 resulted in a transient loss of body weight (FIG. 7B).

Figure 7C:
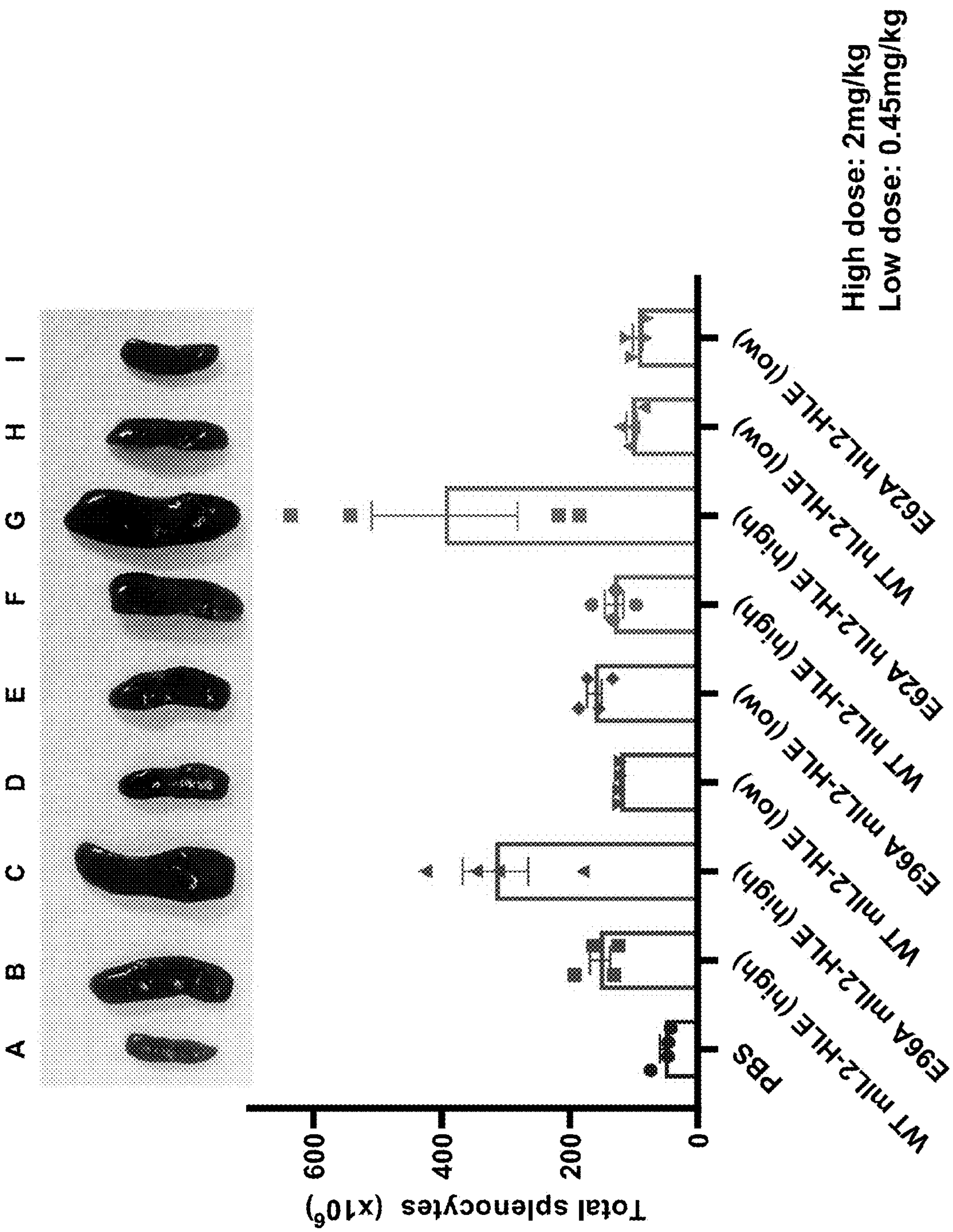
FIG. 7C is a graph scoring the total number of splenocytes upon treatment of mice with E62A-HLE or with E96A-HLE relative to WT mIL-2-HLE or WT hIL2-HLE at a low dose as well as a high dose administration.

Spleens were mashed through a 70 μm cell strainer in RP10. Cells were RBC lysed with RBC lysis buffer and viable splenocytes were counted by ViCell. Spleens were stained by live/dead e780, anti-CD3, anti-CD4, anti-CD8, anti-CD25, and anti-foxp3, all stained according to manufacturer's instructions. Splenocytes were washed and incubated with antibody in stain buffer, and intracellular staining was performed using foxp3 staining buffer set. Cells were analyzed on an LSRFortessa FACS machine, and data were analyzed using FloJo software (TreeStar). Lymphocytes were gated based on FSC/SSC and doublets were excluded. Naive T cells were identified as CD3+CD4+foxp3+. Treatment of mice with two doses of WT mIL-2-HLE or WT hIL2-HLE resulted in an increase in the number of splenocytes while treatment of mice with two doses of E62A-HLE resulted in a greater dose-dependent expansion of splenocytes (FIG. 7C).

Figure 8D:
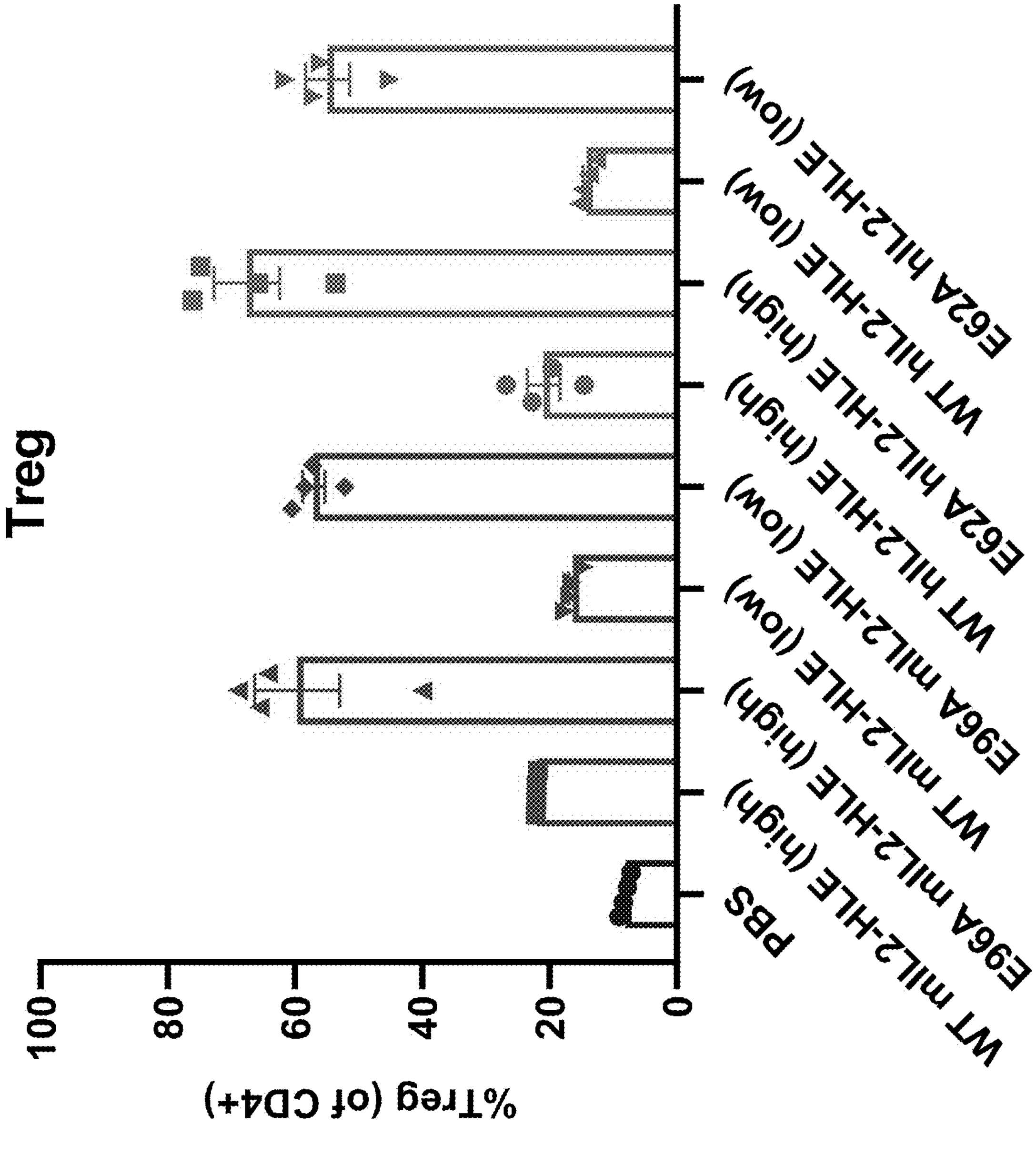
Figure 8E:
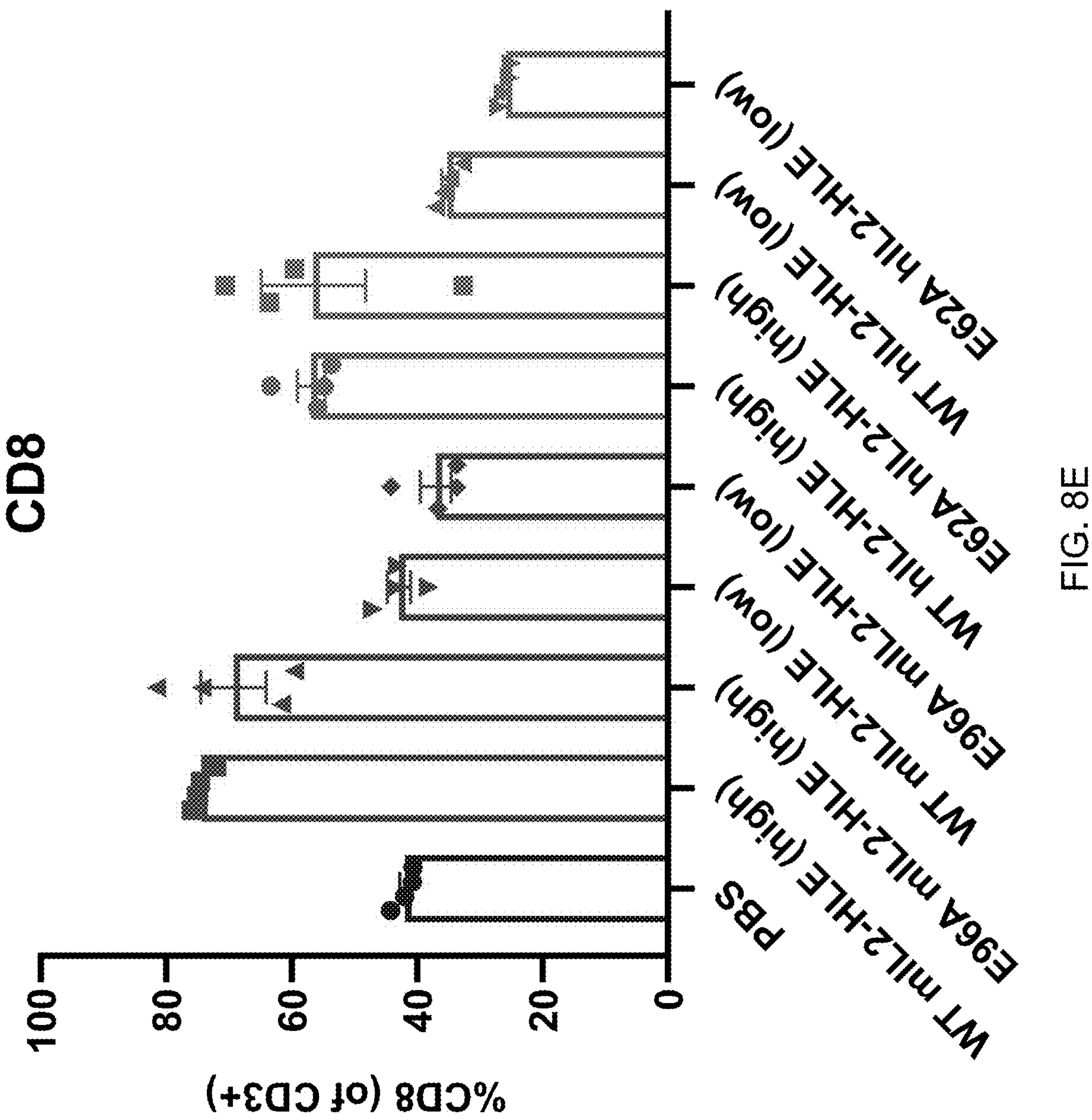
Figure 8F:
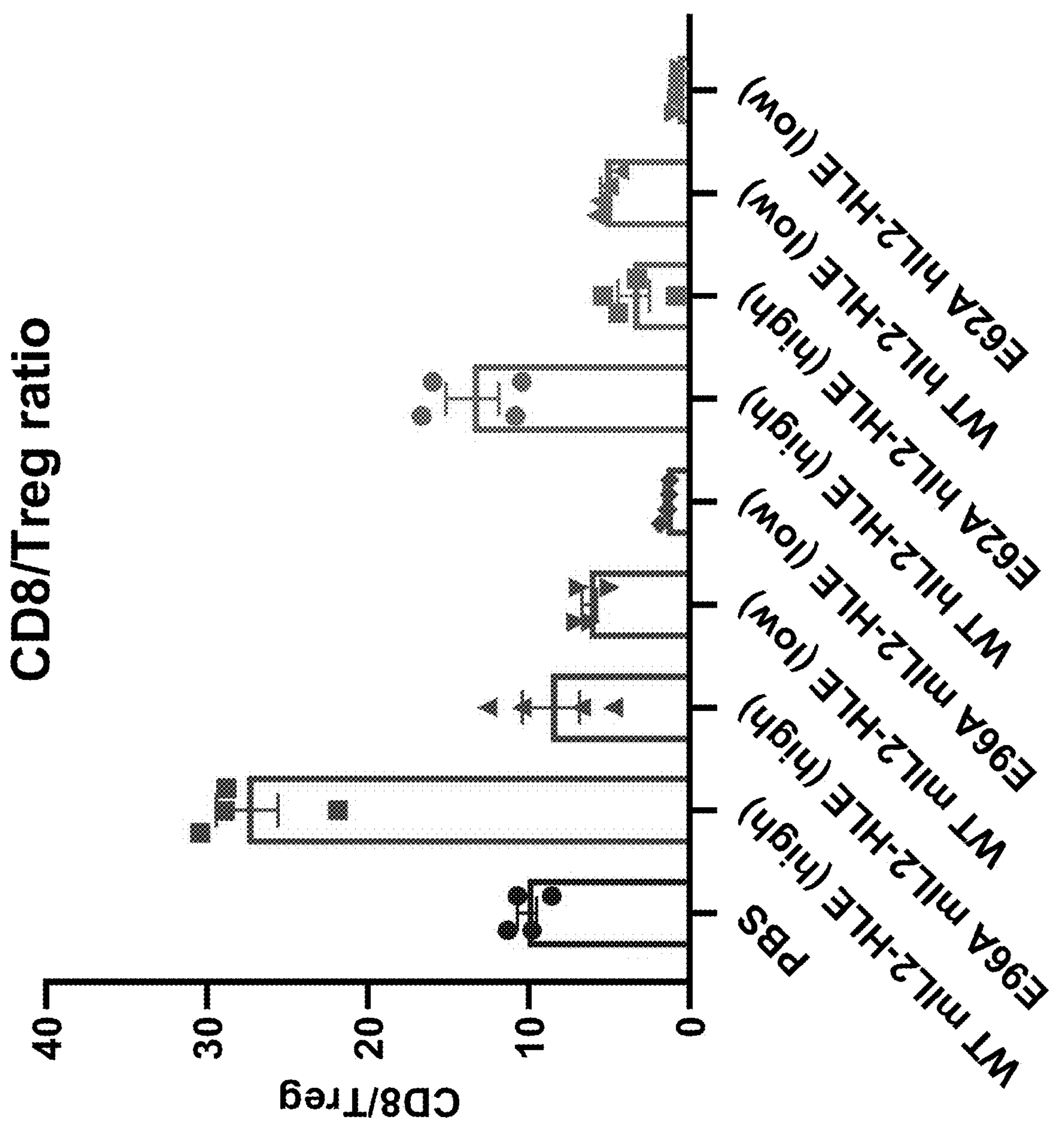

Treatment of mice with E96A-HLE or with E62A-HLE resulted in a greater dose-dependent expansion of CD4+ foxp3+ T cells. Treatment of mice with WT hIL2-HLE or WT mIL-2-HLE resulted in an increase in the ratio of CD8:Tregs, while treatment of mice with E62A-HLE or with E96A-HLE resulted in a greater decrease in the ratio of CD8:Tregs as a result of the preferential expansion of Tregs (FIG. 8D-8F).

Example 8. The Administration of E62A-HLE Protected Mice from Autoimmune Hyperglycemia This example demonstrates that administration of E62A-HLE resulted in increased Treg proliferation in vivo as well as increased protection of treated mice from an exemplary autoimmune condition, autoimmune hyperglycemia.

At 7 weeks of age, mice were assigned to treatment groups based on non-fasted blood glucose and were dosed according to Table 6 via intraperitoneal (IP) injection of 100 μl/mouse. Body weights, clinical observations, and non-fasted blood glucose were recorded weekly for study duration. Any animals with non-fasted blood glucose >250 mg/dL for two consecutive days were humanely euthanized.

TABLE 6

Mouse Study Dosing Schedule

| Group | N | Test Articles | Dose | Route | Dosing Schedule |
|---|---|---|---|---|---|
| 1 | 13 | Vehicle | N/A | i.p. | Once weekly for 2 weeks, then every other week up to 20 weeks of age (8 doses total) |
| 2 | 13 | Test | 0.1 mg/ml | i.p. | Once weekly for 3 weeks |
| 3 | 10 | Test1 | 0.1 mg/ml | i.p. | Once weekly for 2 weeks, then every other week up to 20 weeks of age (8 doses total) |

At 10 weeks of age, 3 mice from treatment groups 1 and 2 were humanely euthanized and splenocytes were assessed via flow cytometry using a standard T cell and NK cell panel.

At 30 weeks of age, the remaining mice on study were humanely euthanized and tissues were collected for flow cytometry using a standard T cell and NK cell panel.

Figure 9A:
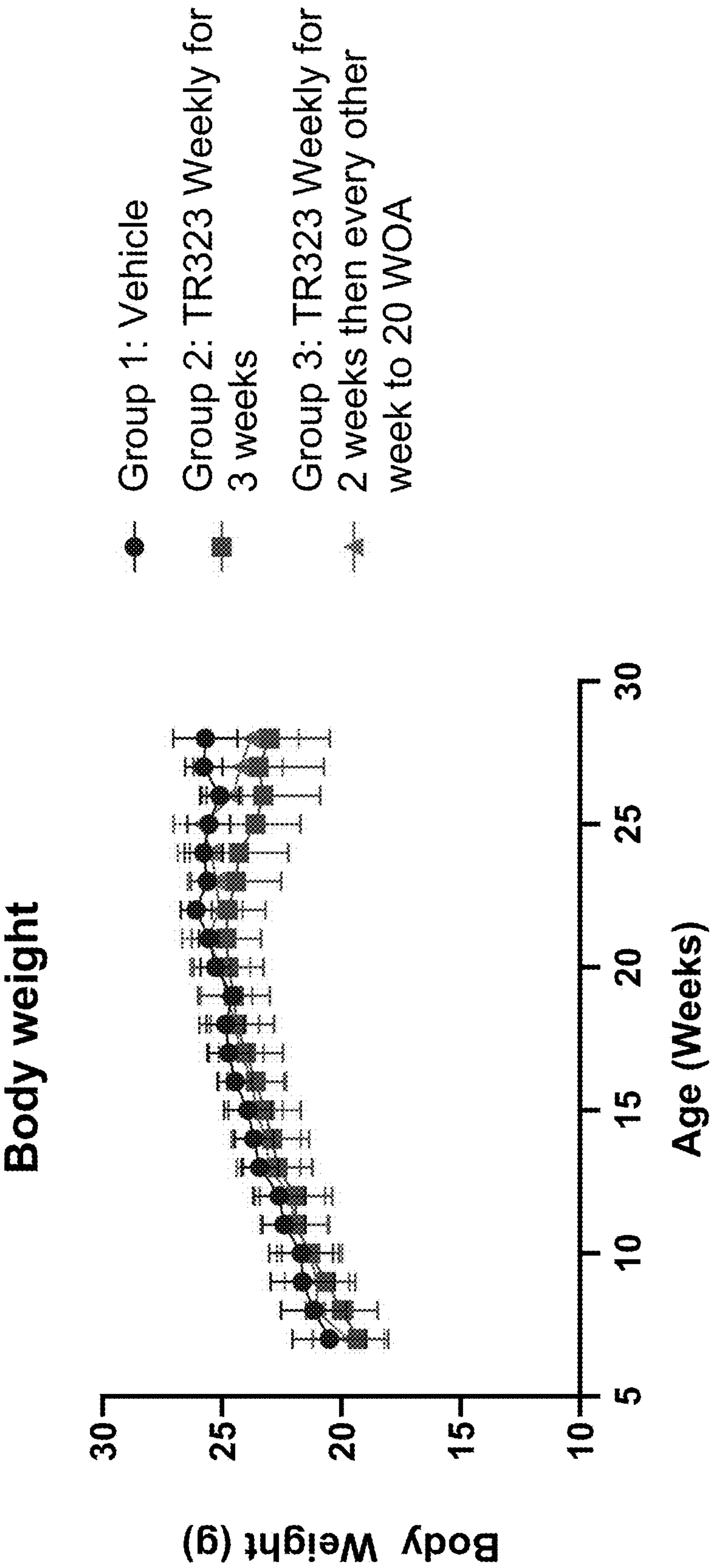
FIG. 9A is a graph of percent body weight monitored up to 30 weeks upon administration of IL-2 muteins in two dosing regimens.

Neither dosing regimen of E62A-HLE resulted in a loss of body weight (FIG. 9A).

Figure 9B:
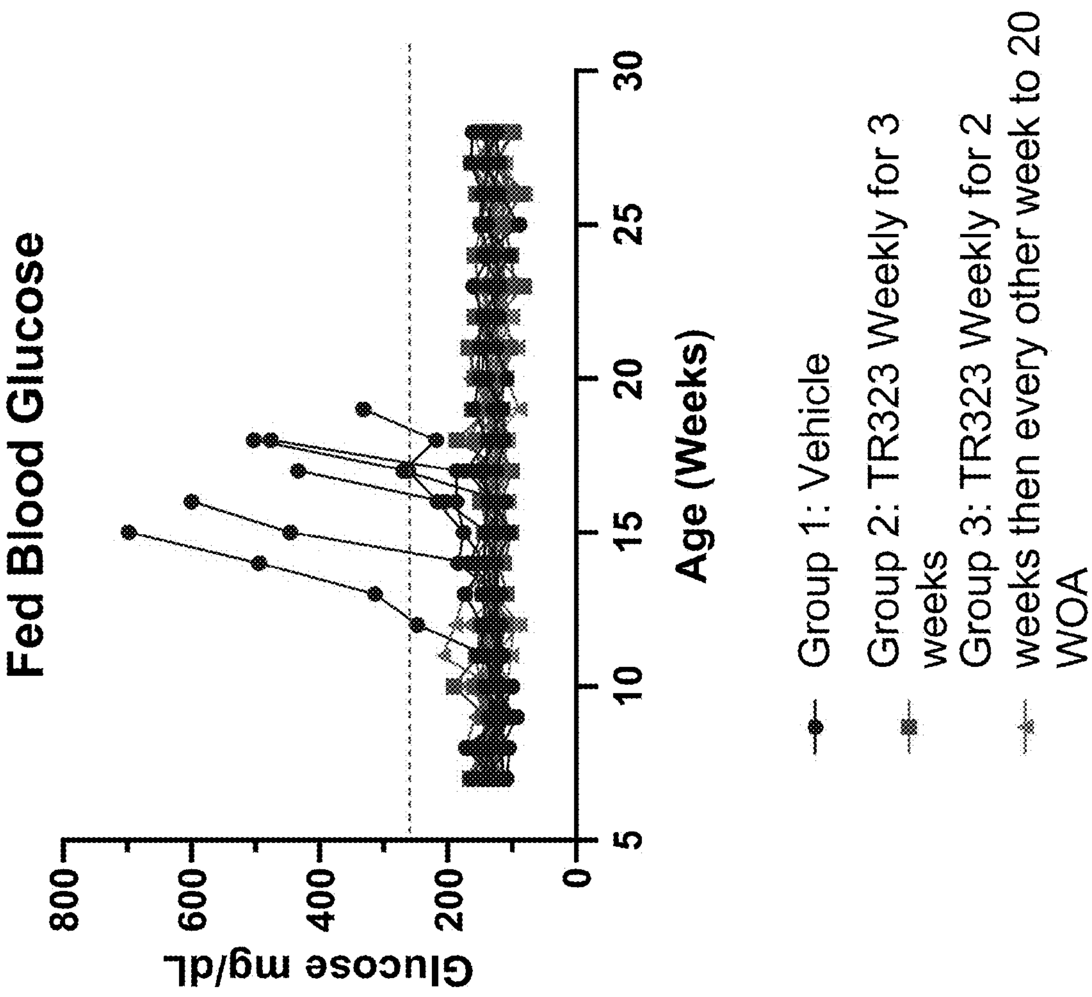
FIG. 9B is a graph of blood glucose levels measured in mice treated with IL-2 muteins in two dosing regimens.
Figure 9C:
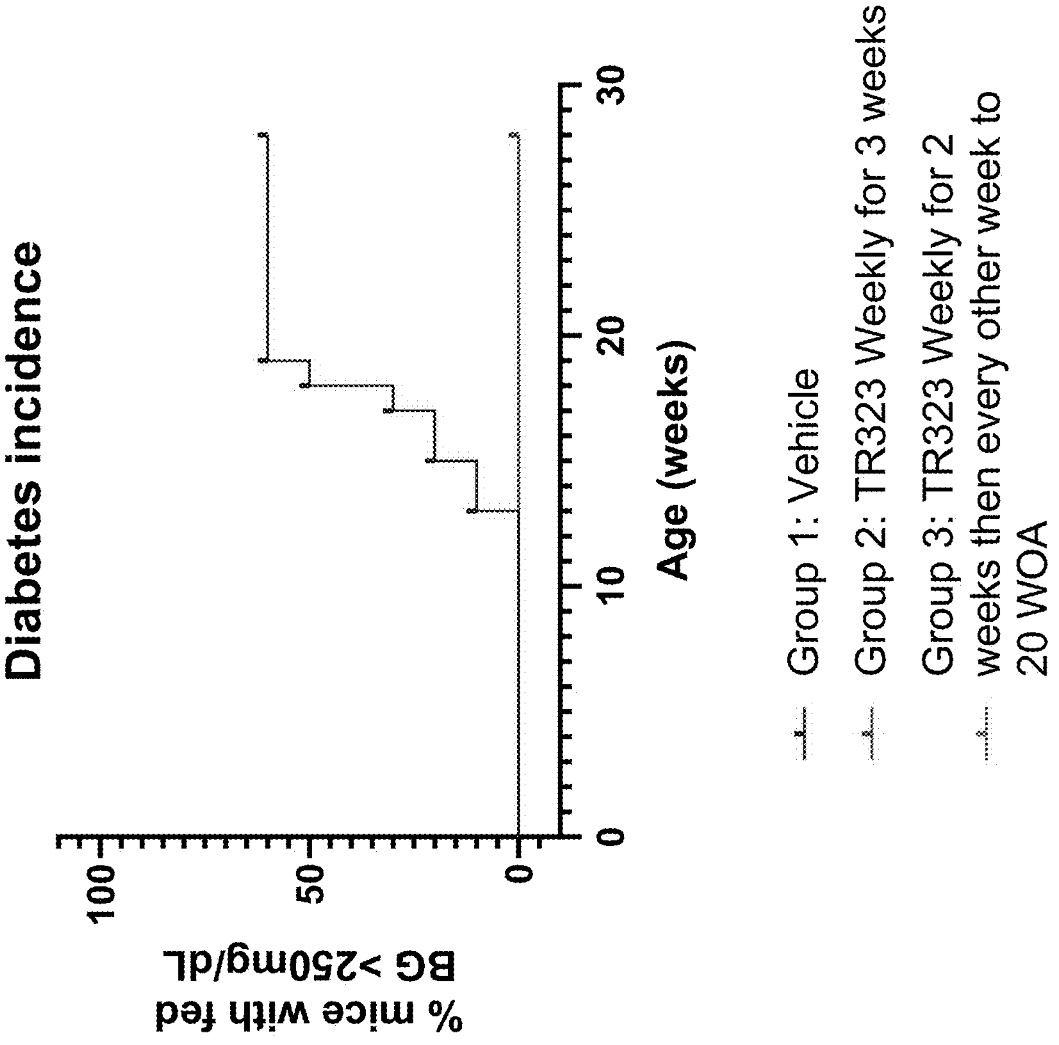
FIG. 9C is a graph that shows the incidence of diabetes in a population of mice treated with IL-2 muteins relative to vehicle controls.

Blood glucose was measured (FIG. 9B). The results showed that in contrast to control mice which demonstrated 60% incidence of hyperglycemia by 20 weeks of age (n=10), no mice treated with E62A-HLE developed hyperglycemia by 30 weeks of age (n=19) suggesting that expansion of Tregs protects mice from autoimmune hyperglycemia (FIG. 9C).

Figure 10B:
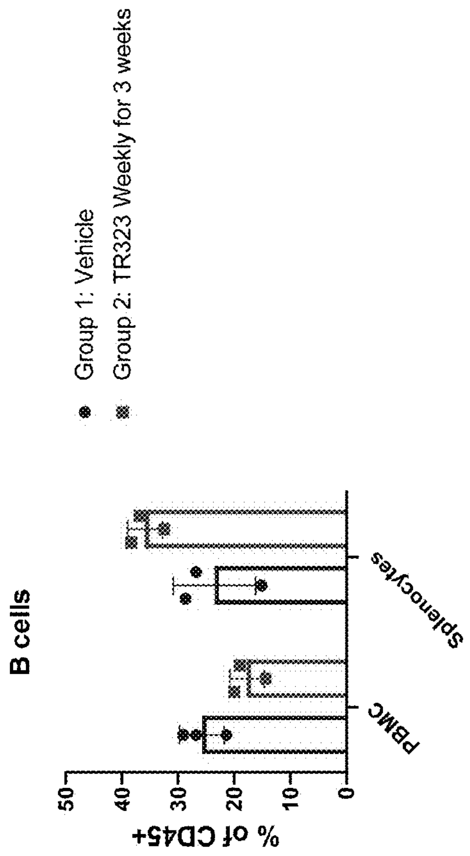
FIG. 10B is a graph of percent CD45+ cells in PBMC and splenocytes in B cells after IL-2 mutein treatment regimen relative to a vehicle control.
Figure 10A:
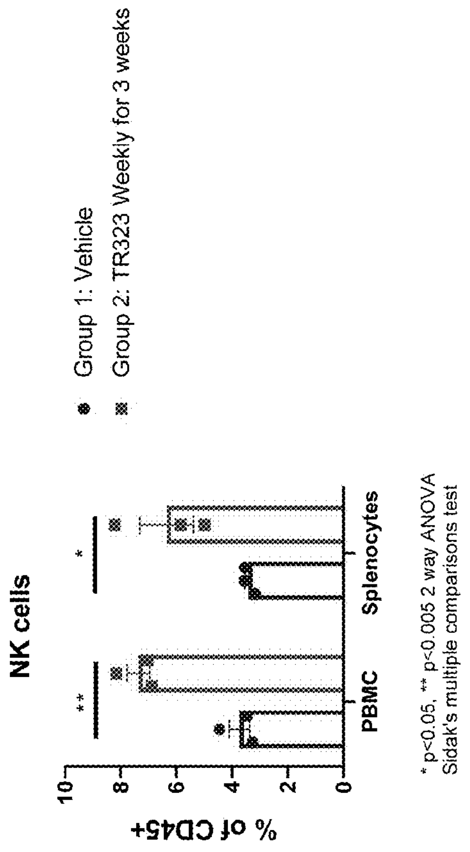
FIG. 10A is a graph of percent CD45+ cells in PBMC and splenocytes in NK cells after IL-2 mutein treatment regimen relative to a vehicle control.
Figure 10C:
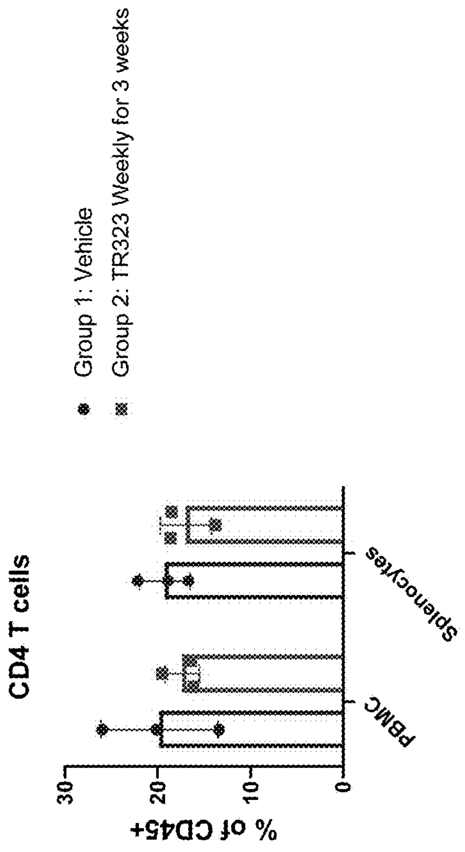
FIG. 10C is a graph of percent CD45+ cells in CD4+ T cells after IL-2 mutein treatment regimen relative to a vehicle control.
Figure 10D:
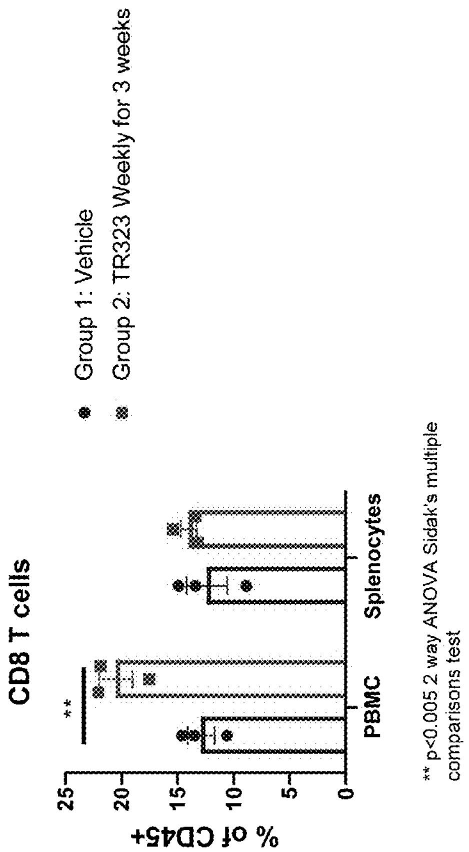
FIG. 10D is a graph of percent CD45+ cells in CD8+ T cells after IL-2 mutein treatment regimen relative to a vehicle control.
Figure 11A:
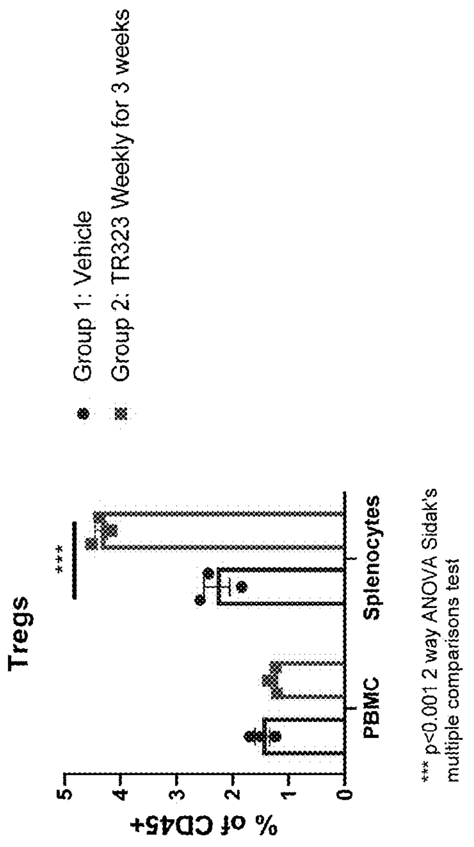
FIG. 11A is a graph of CD45+ Tregs in PBMC and splenocytes after IL-2 mutein treatment regimen relative to a vehicle control.
Figure 11B:
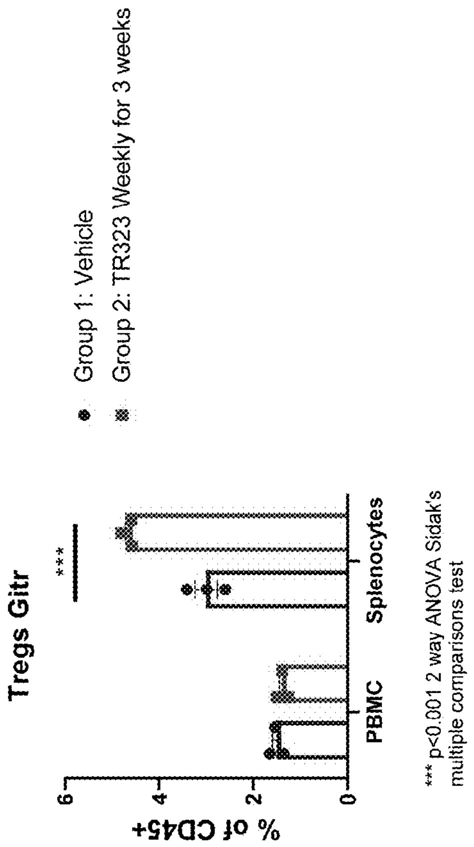
FIG. 11B is a graph of CD45+ GITR (Glucocorticoid-Induced Tumor Necrosis Factor) expressing Tregs in PBMC and splenocytes after IL-2 mutein treatment regimen relative to a vehicle control.

In splenocytes of E62A-HLE-treated mice, Tregs were expanded (FIG. 11A and FIG. 11B). NK cells (FIG. 10A) and CD8+ T cells (FIG. 10D) were also expanded in E62A-treated mice. B cells were increased in splenocytes from E62A treated mice (FIG. 10B), however, CD4+ T cells were not expanded (FIG. 10C).

Example 9. PD Following Single Administration of E62A-HLE at Multiple Timepoints and in Multiple Tissues This example demonstrates PD following single administration of E62A-HLE at multiple timepoints and in multiple tissues.

To understand the biological activity of E62A-HLE compared to WT hIL-2-HLE (referred to as Cyto5 (2124-T60) in figures), mice were treated with these cytokines. CD8 and CD4 T cells, including Tregs, were examined for changes in growth of immune cell subsets. Female C57BL/6 were inoculated B16F10 tumor ($8\times10^4$ cell suspension) subcutaneously in 0.1 mL volume. A single treatment of E62A-HLE was administered intraperitoneally. Following treatment with E62A-HLE, mice were euthanized 96 hrs, 168 hrs, and 240 hrs post-injection, and whole blood, lymph node, spleen, and tumor were harvested for analysis. Flow antibodies included: anti-CD45, anti-CD8, anti-CD4, anti-ICOS, live/dead, anti-hCTLA-4, Ki67, anti-NKp46, anti-CD19, anti-Ly6G, anti-CD25, anti-CD62L, anti-foxp3, anti-CD44, anti-TCRb, all stained according to manufacturer's instructions. Antibodies were washed and stained in stain buffer, and intracellular staining was performed using foxp3 staining buffer set. Cells were analyzed on an LSRFortessa FACS machine (BD) and data were analyzed using FloJo software (TreeStar). Lymphocytes were gated based on FSC/SSC and doublets were excluded. Naive T cells were identified as CD3+CD4+foxp3+.

Figure 12A:
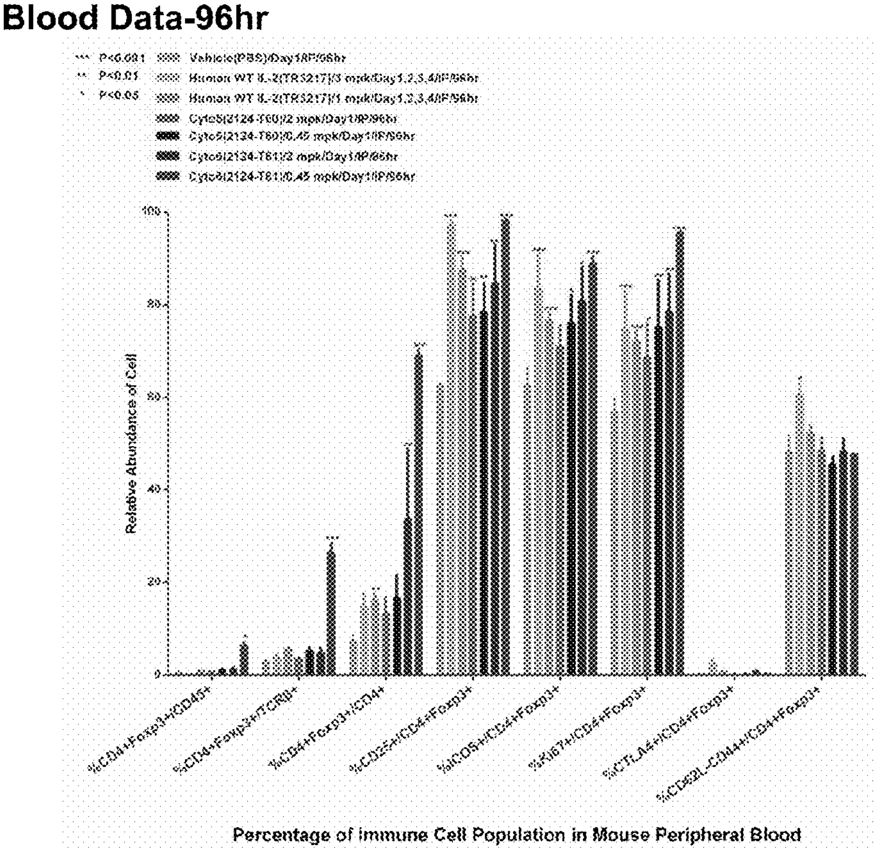
FIG. 12A and FIG. 12B are graphs of the percentage of immune cells in mouse peripheral blood at 96 hrs after IL-2 mutein treatment regimen relative to a vehicle control.
Figure 12B:
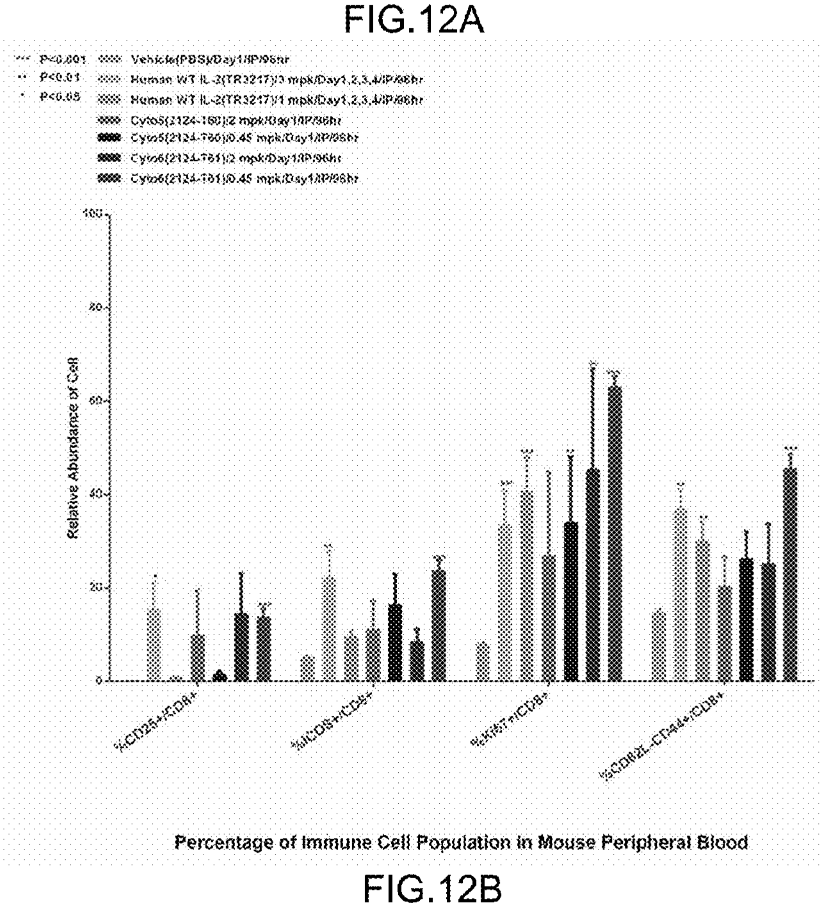

In the blood, at 96 hrs post-injection, a single administration of E62A-HLE (referred to as Cyto6 (2124-T61) in the figures) resulted in expansion of CD4+foxp3+ as a proportion of hematopoietic CD45+ cells. In the blood, at 96 hrs post-injection, a single administration of E62A-HLE resulted in expansion of CD4+foxp3+ as a proportion of TCRb+ cells. In the blood, at 96 hrs post-injection, a single administration of E62A-HLE resulted in expansion of CD4+ foxp3+ as a proportion of hematopoietic CD4+ cells (FIG. 12A and FIG. 12B).

Figure 13A:
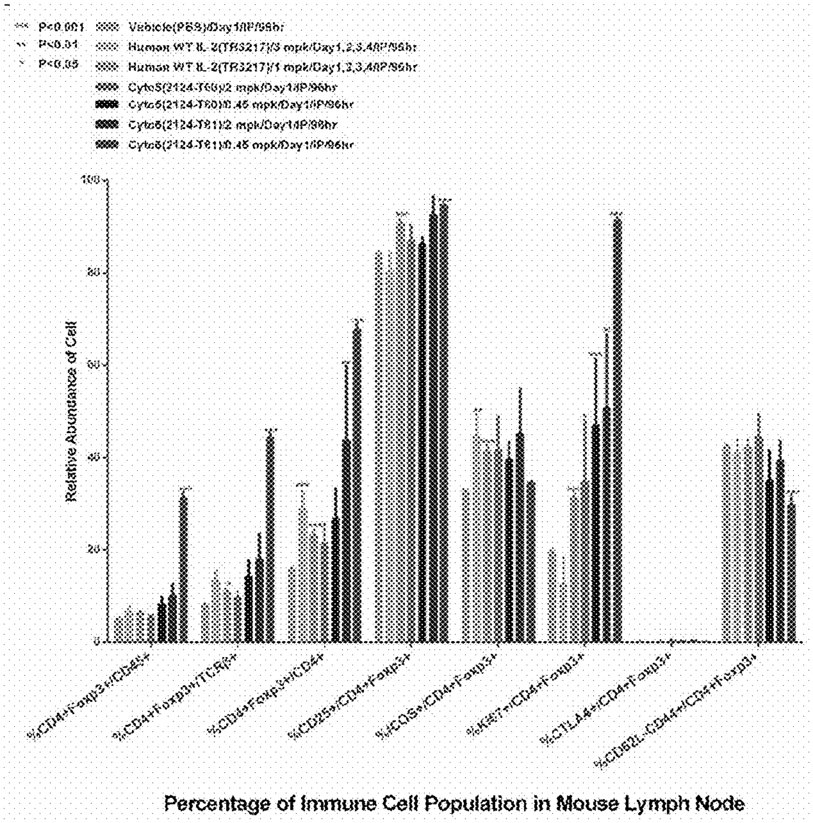
FIG. 13A and FIG. 13B are graphs of the percentage of immune cells in the lymph node at 96 hrs after IL-2 mutein treatment regimen relative to a vehicle control.
Figure 13B:
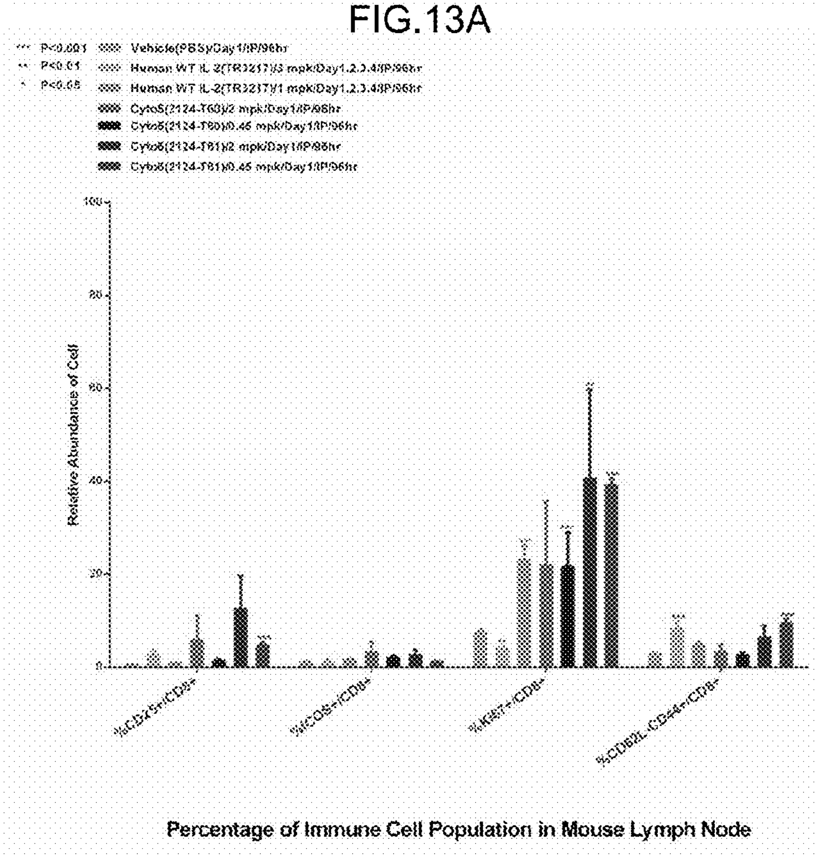

In the lymph node, at 96 hrs post-injection, a single administration of E62A-HLE resulted in expansion of CD4+ foxp3+ as a proportion of hematopoietic CD45+ cells. In the lymph node, at 96 hrs post-injection, a single administration of E62A-HLE resulted in expansion of CD4+foxp3+ as a proportion of TCRb+ cells. In the lymph node, at 96 hrs post-injection, a single administration of E62A-HLE resulted in expansion of CD4+foxp3+ as a proportion of hematopoietic CD4+ cells. In the lymph node, at 96 hrs post-injection, a single administration of E62A-HLE resulted in expansion of Ki67+Tregs (FIG. 13A and FIG. 13B).

Figure 14A:
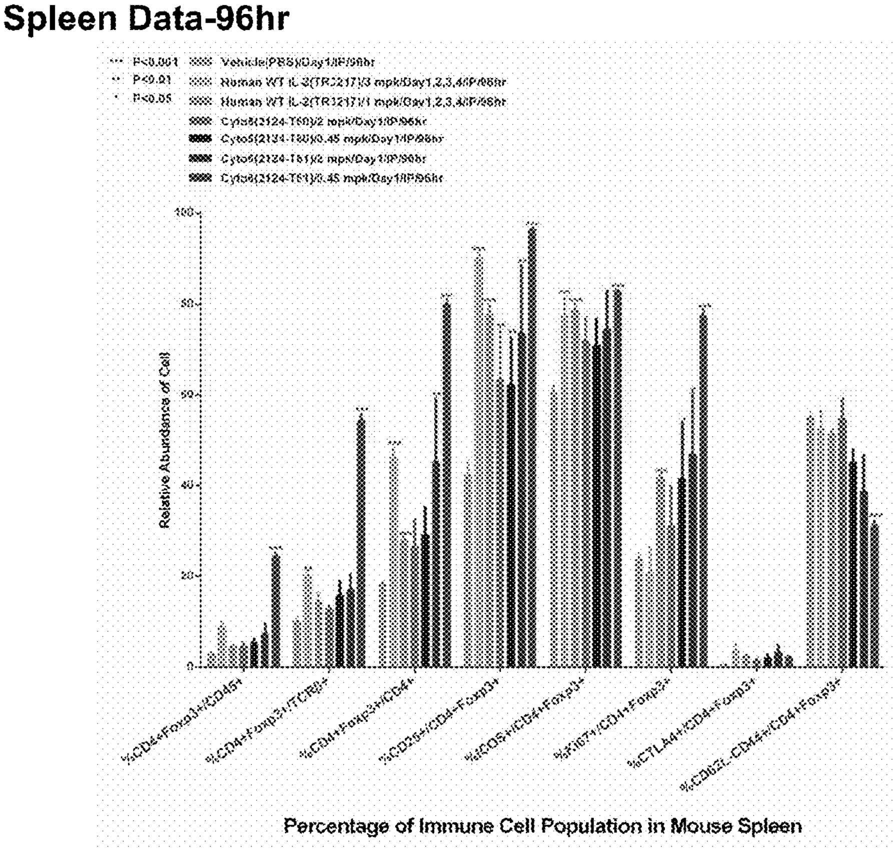
FIG. 14A and FIG. 14B are graphs of the percentage of immune cells in the spleen at 96 hrs after IL-2 mutein treatment regimen relative to a vehicle control.
Figure 14B:
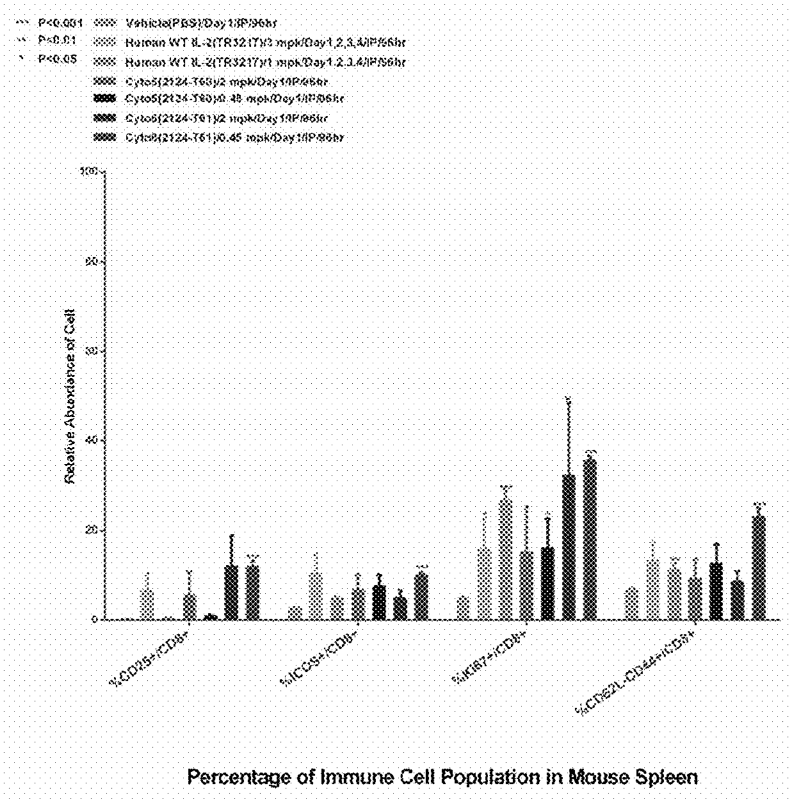

In the spleen, at 96 hrs post-injection, a single administration of E62A-HLE resulted in expansion of CD4+foxp3+ as a proportion of hematopoietic CD45+ cells. In the spleen, at 96 hrs post-injection, a single administration of E62A-HLE resulted in expansion of CD4+foxp3+ as a proportion of TCRb+ cells. In the spleen, at 96 hrs post-injection, a single administration of E62A-HLE resulted in expansion of CD4+foxp3+ as a proportion of hematopoietic CD4+ cells. In the spleen, at 96 hrs post-injection, a single administration of E62A-HLE resulted in expansion of Ki67+Tregs. In the spleen, at 96 hrs post-injection, a single administration of E62A-HLE resulted in expansion of CD44+CD62L-neg Tregs (FIG. 14A and FIG. 14B).

Figure 15A:
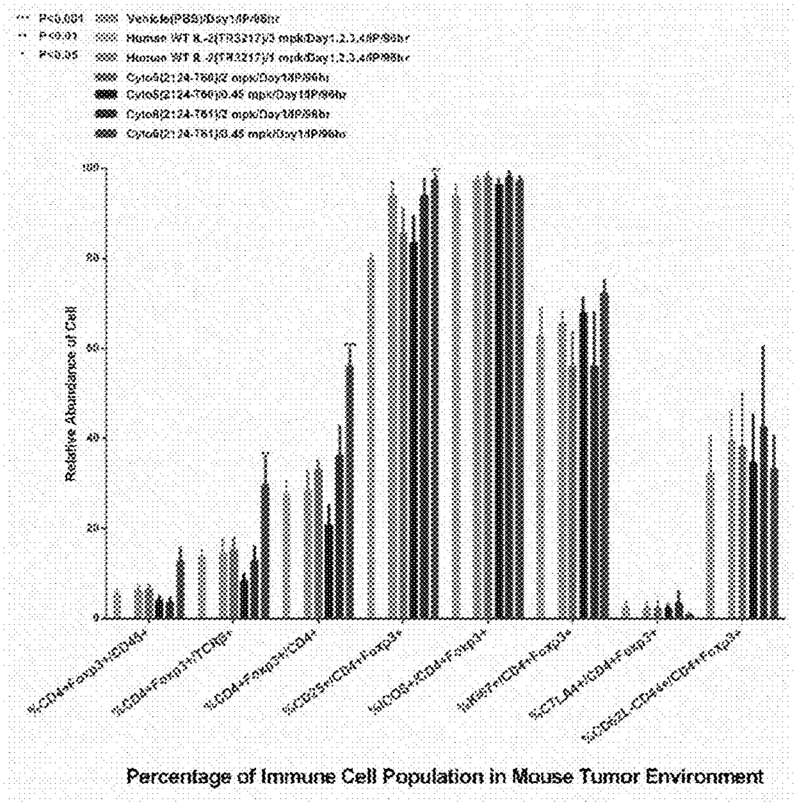
FIG. 15A and FIG. 15B are graphs of the percentage of immune cells in tumors at 96 hrs after IL-2 mutein treatment regimen relative to a vehicle control.
Figure 15B:
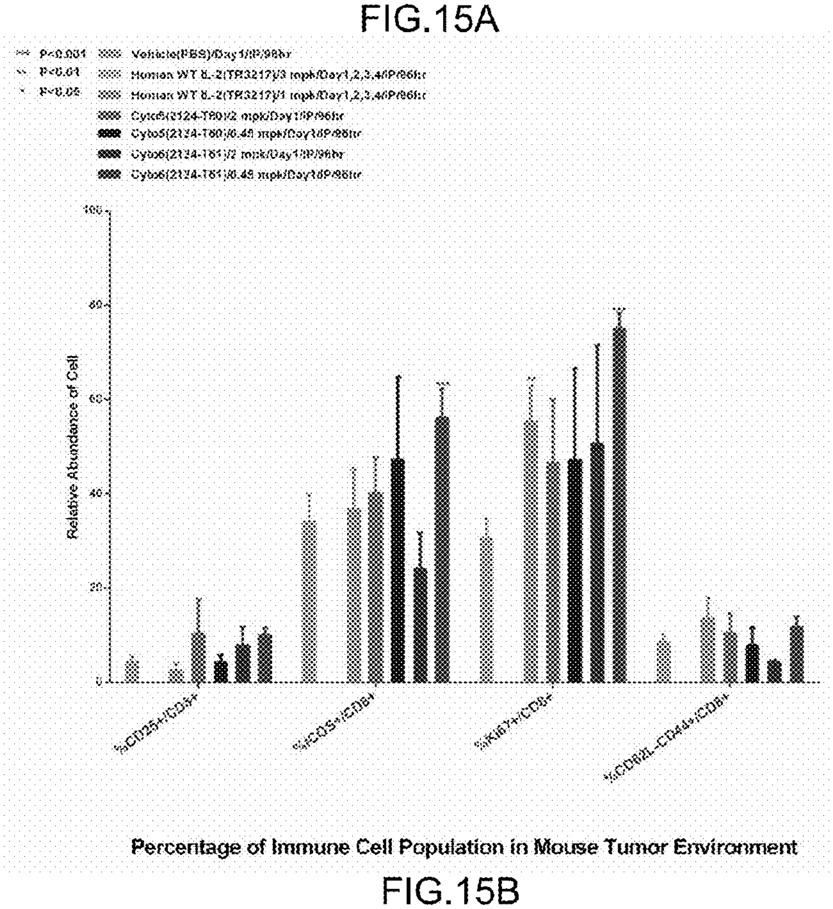

In the tumor, at 96 hrs post-injection, a single administration of E62A-HLE resulted in expansion of CD4+foxp3+ as a proportion of hematopoietic CD45+ cells. In the tumor, at 96 hrs post-injection, a single administration of E62A-HLE resulted in expansion of CD4+foxp3+ as a proportion of TCRb+ cells. In the tumor, at 96 hrs post-injection, a single administration of E62A-HLE resulted in expansion of CD4+foxp3+ as a proportion of hematopoietic CD4+ cells (FIG. 15A and FIG. 15B).

Figure 16A:
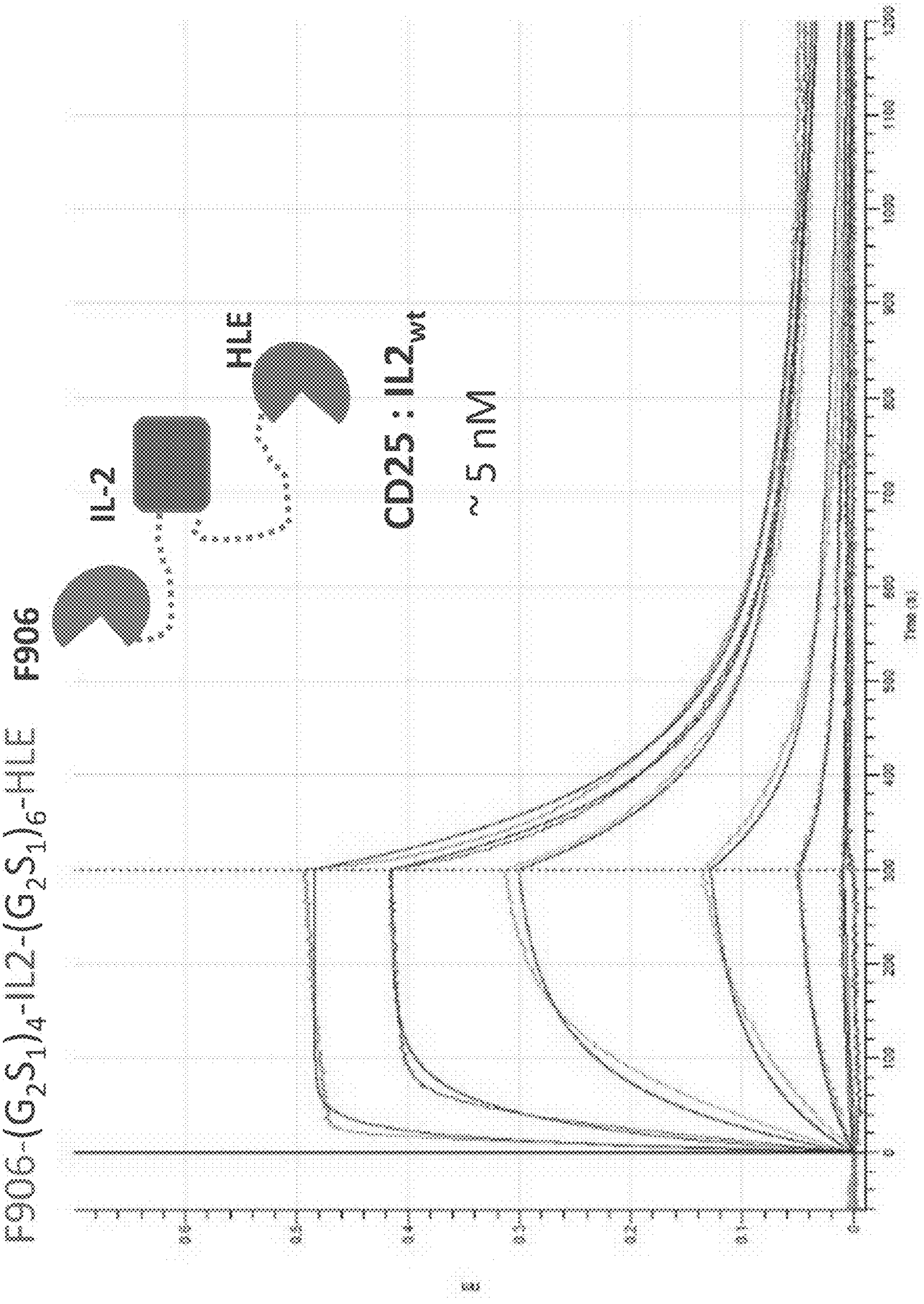
FIG. 16A is a graph of binding affinity between WT human IL-2 and human CD25 (IL-2Rα) receptor.
Figure 16B:
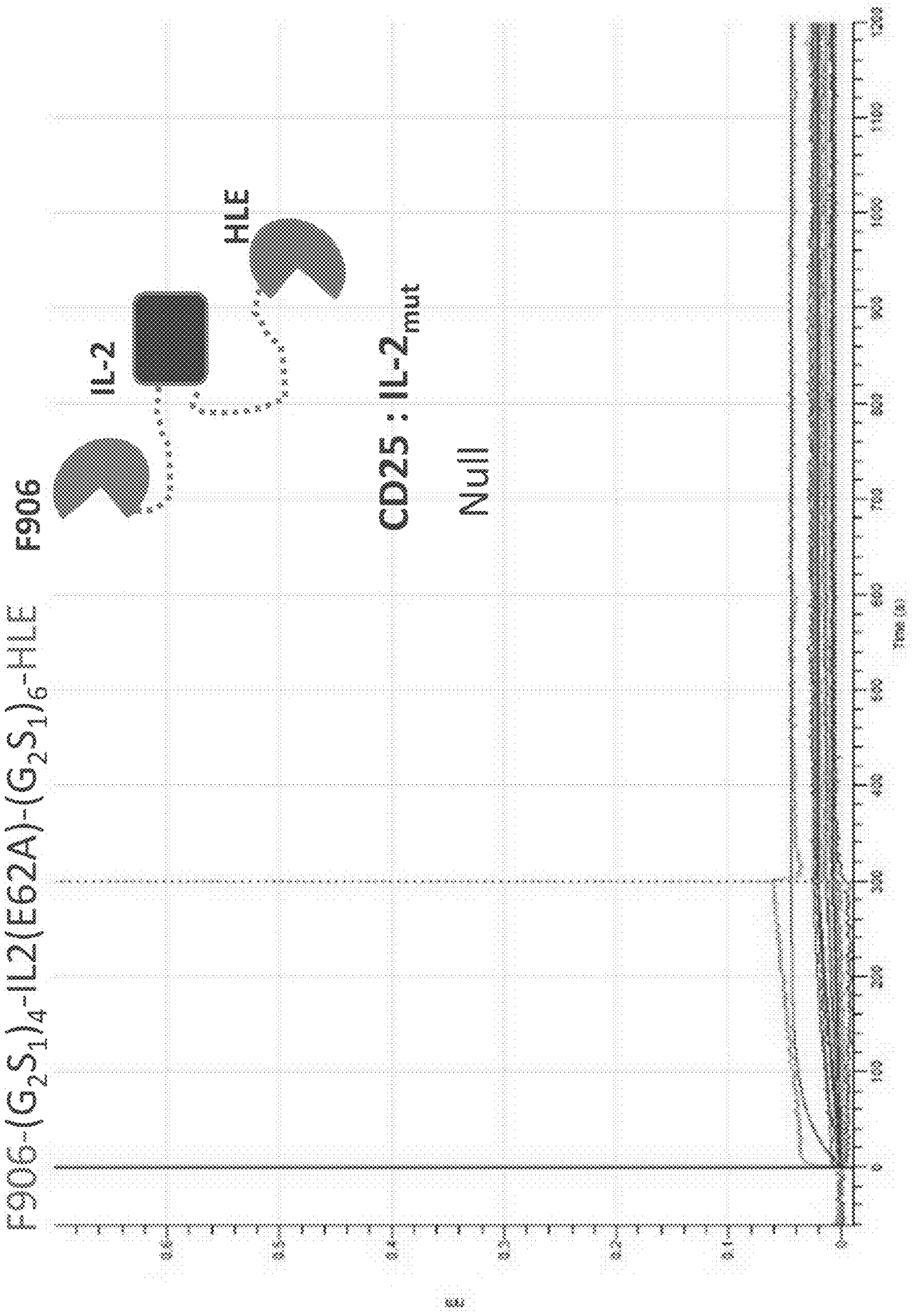
FIG. 16B is a graph of binding affinity between human IL-2 mutein and human CD25 (IL-2Rα) receptor.
Figure 17A:
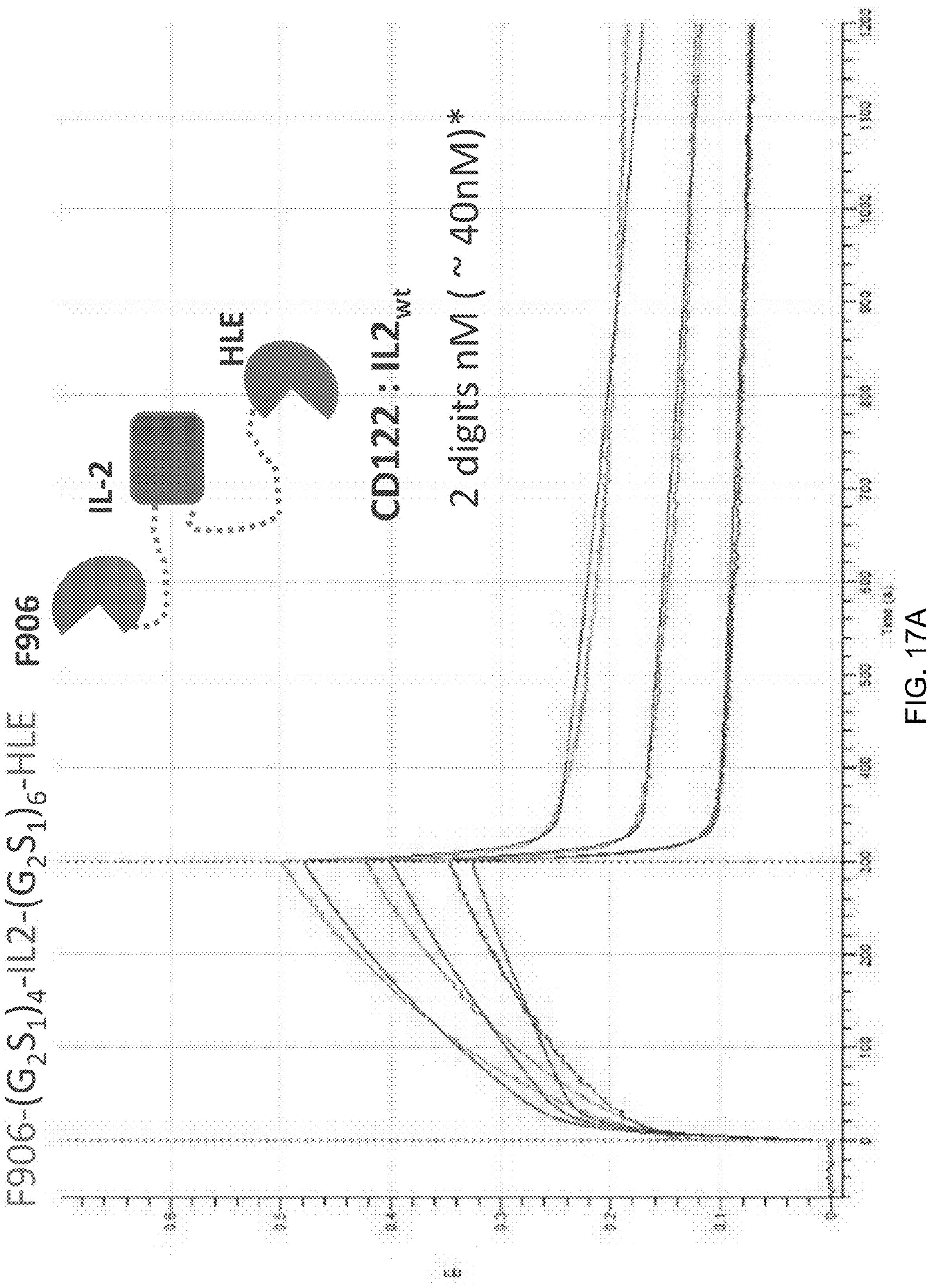
FIG. 17A is a graph of binding affinity between WT IL-2 and CD122 (IL-2Rβ) receptor.
Figure 17B:
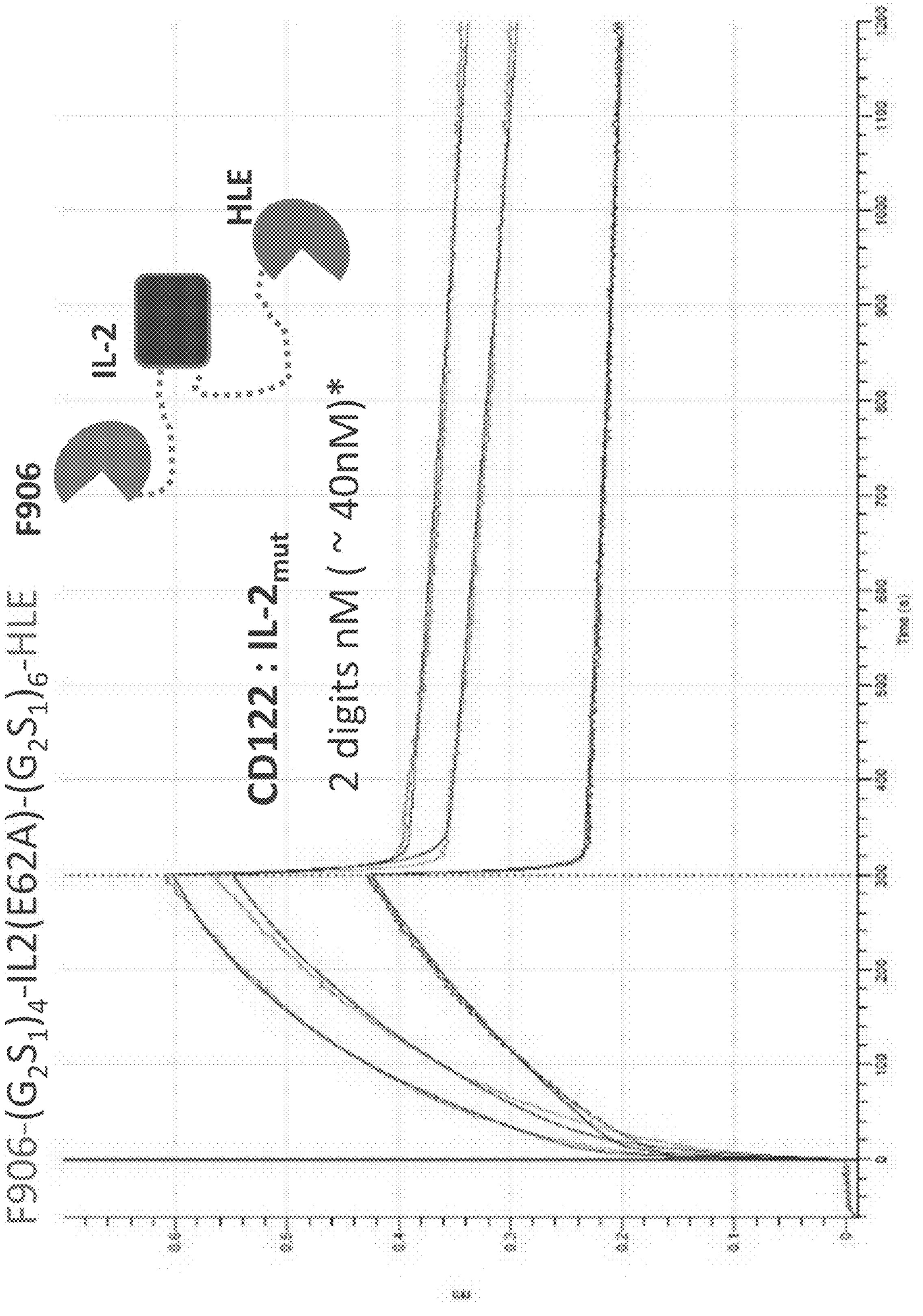
FIG. 17B is a graph of binding affinity between IL-2 mutein and CD25 (IL-2Rβ) receptor.

The results of binding assays showed that WT IL-2 binds IL-2Rα (CD25) (FIG. 16A) but this ability was lost in the E62A IL-2 mutein (FIG. 16B). Binding assays also showed that WT IL-2 as well as E62A IL-2Rα mutein binds IL-2Rβ CD122 (FIG. 17A and FIG. 17B).

Figure 18A:
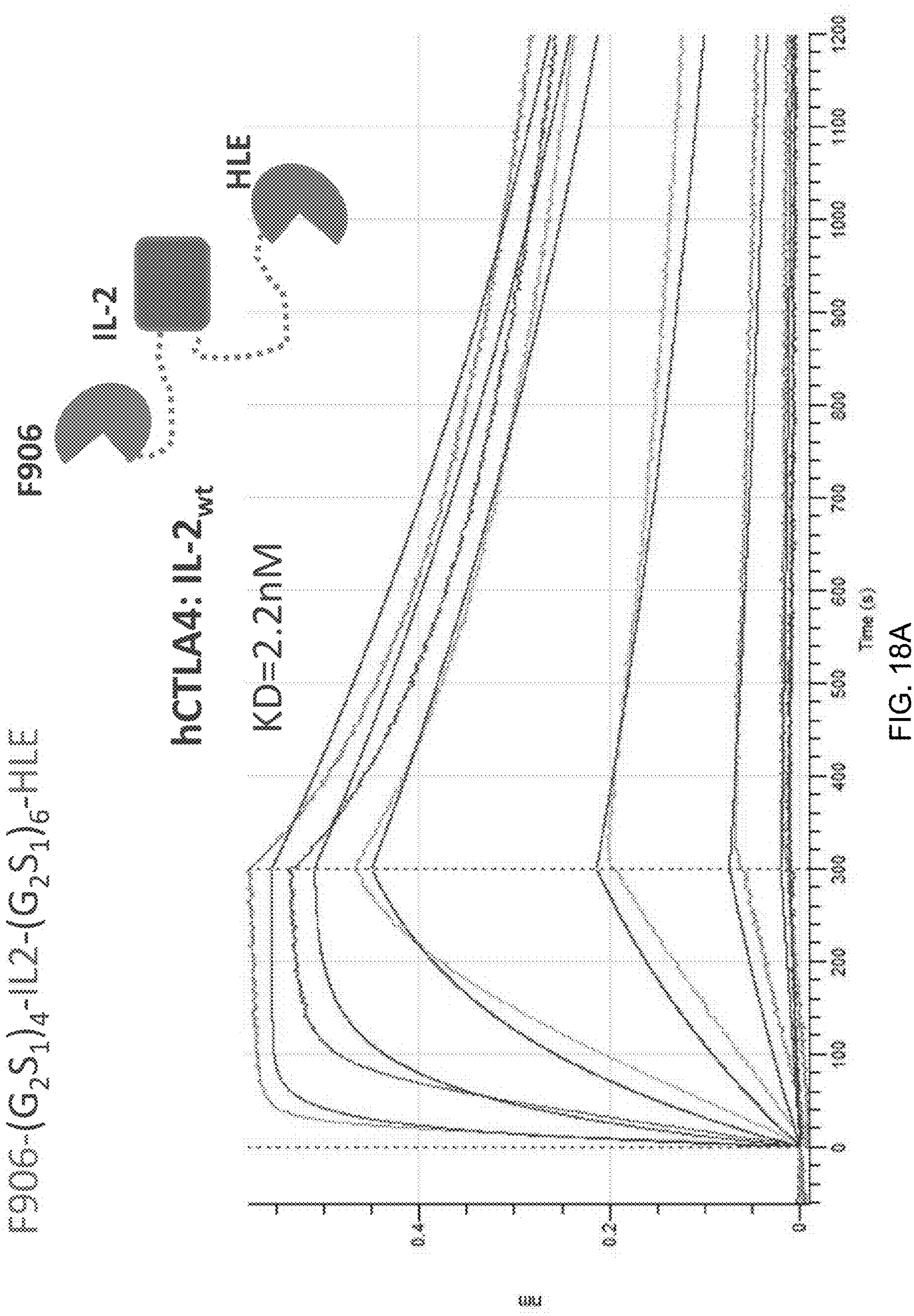
FIG. 18A is a graph of binding affinity between hCTLA4 and IL-2 WT fusion protein.
Figure 18B:
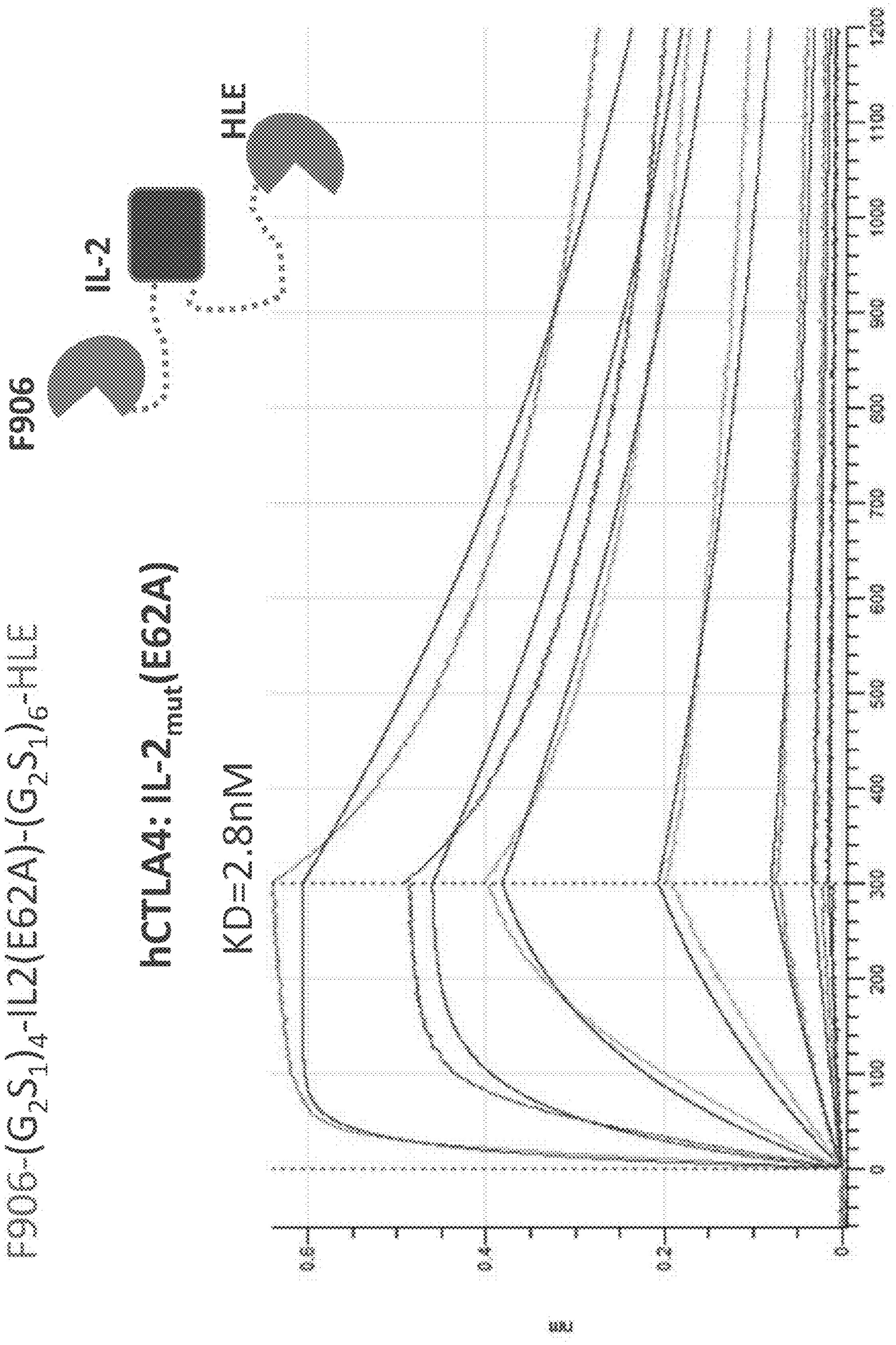
FIG. 18B is a graph of binding affinity between hCTLA4 and IL-2 mutein, E62A.

The results of binding assays showed that the WT IL-2 as well as the E62A IL-2 mutant fusion protein binds to hCTLA-4 (FIG. 18A and FIG. 18B).

Example 10. Effects of M23L and T111H in Cynomolgus Monkey after Multiple Doses of Administration This example illustrates the in vivo effects of exemplary M23L and T111H mutein compared to WT hIL-2 after administration of multiple doses in monkey.

Figure 19A:
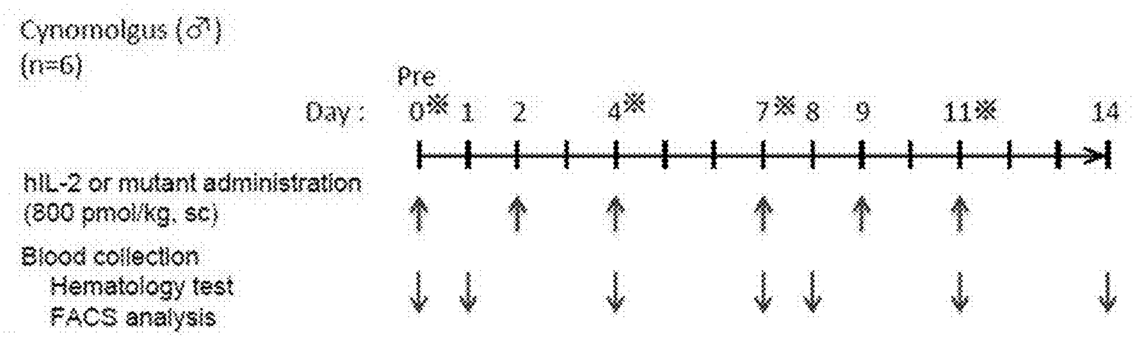
FIG. 19A is a schematic that shows the experimental design for testing the effects of M23L, T111H and WT hIL-2, in cynomolgus monkeys after multiple rounds of administration.

To understand the biological activity of M23L, T111H and WT hIL-2, monkeys were treated with these cytokines. CD8 and CD4 T cells, including Tregs, were examined for changes in growth of immune cell subsets. Each of the biologics was diluted in 1×PBS. For each biologic, monkeys received 800 μmol/kg of cytokines, subcutaneously, n=6 in each group, at day 0, 2, 4, 7, 9 and 11 (FIG. 19A).

For each group, four monkeys were administered multiple doses of treatment and blood was collected at day 0, 1, 4, 7, 8, 11 and 14. Blood cells were stained by anti-CD3, anti-CD4, anti-CD8, anti-CD25, anti-CD45RA, anti-CD56, anti-CD16 and anti-Foxp3, all stained according to manufacturer's instructions. Lymphocytes were washed and incubated with antibody in stain buffer, and intracellular staining was performed using foxp3 staining buffer set. Cells were analyzed on an LSRFortessa FACS machine and data were analyzed using FloJo software. Lymphocytes were gated based on FSC/SSC and doublets were excluded. Lymphocytes were gated to identify CD4 T-cell, memory CD4, Naïve CD4, CD4 Treg, memory Treg, Naïve Treg, CD8 T, NK and NKT cells.

Figure 19B:
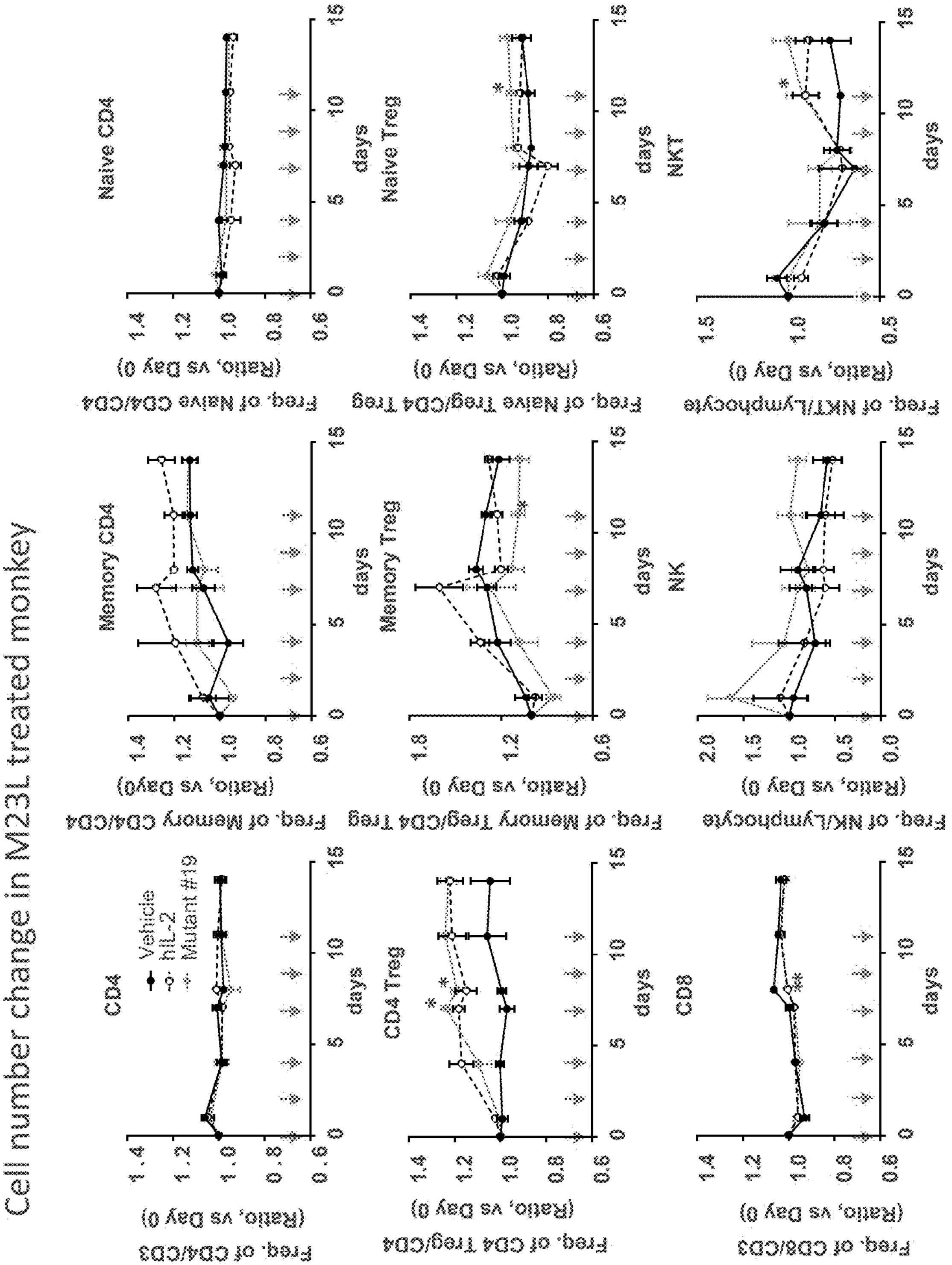
FIG. 19B depicts graphs showing the change in cell number of CD4, memory CD4, naïve CD4, CD4 Treg, memory Treg, naïve Treg, CD8, NK and NKT lymphocyte cells in vehicle-treated, WT hIL-2 treated, and IL-2 mutein, M23L-treated cynomolgus monkeys at days 0, 1, 4, 7, 8, 11 and 14 of treatment.
Figure 19C:
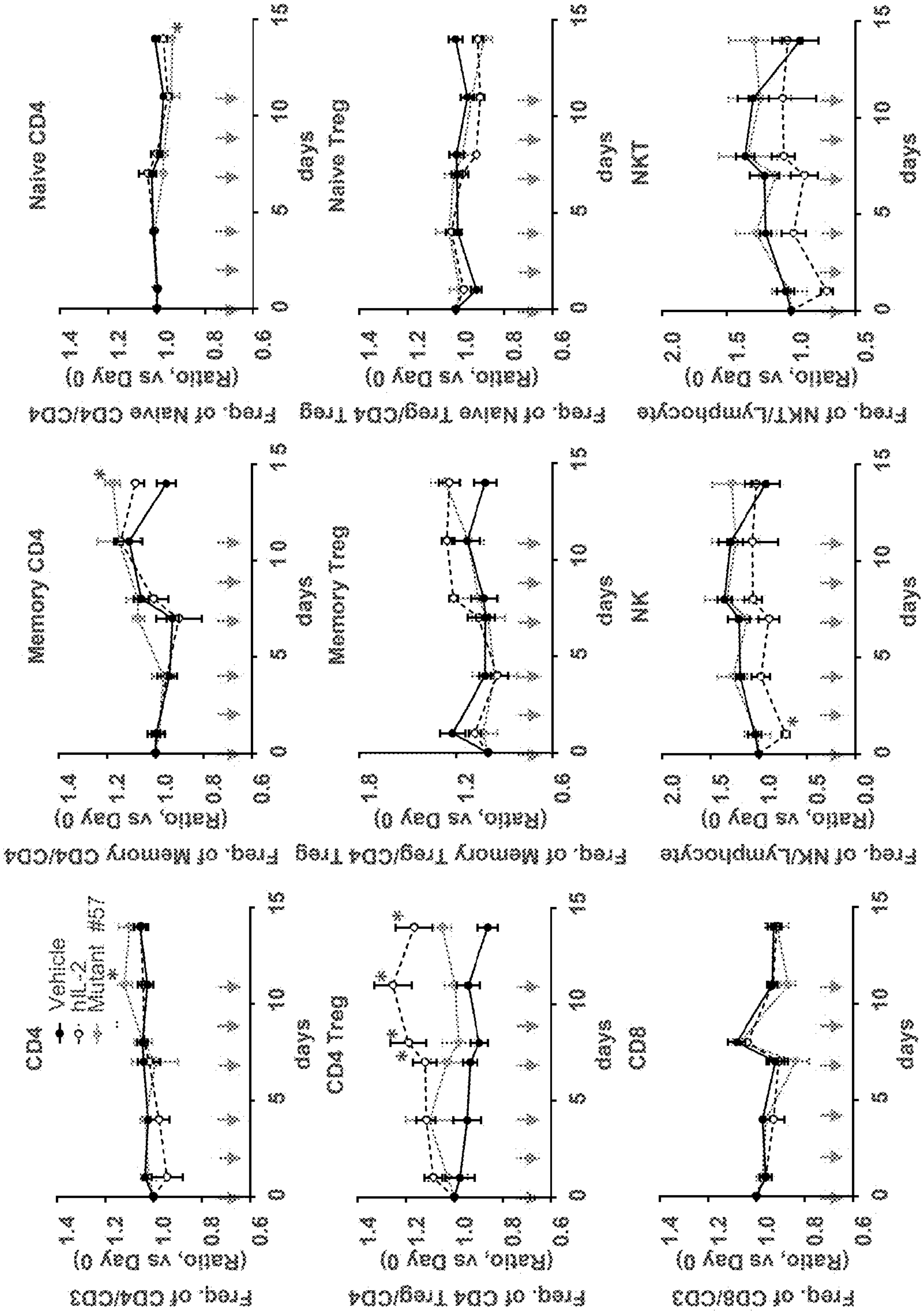
FIG. 19C depicts graphs showing the change in cell number of CD4, memory CD4, naïve CD4, CD4 Treg, memory Treg, naïve Treg, CD8, NK and NKT lymphocyte cells in vehicle-treated, WT hIL-2 treated, and IL-2 mutein, T111H-treated cynomolgus monkeys at days 0, 1, 4, 7, 8, 11 and 14 of treatment.

The results showed that treatment of monkeys with WT hIL-2 resulted in an increase in the number of memory CD4 cells and CD4 Treg cells. Treatment of monkeys with M23L mutein, referred to as Mutant #19 in the graph, resulted in an increase in the number of CD4 Treg cells and no increase in the number of memory CD4 cells (FIG. 19B). Treatment of monkeys with T111H, referred to as Mutant #57 in the graph, resulted in an increase in the number of memory CD4 cells and no increase in the number of CD4 Treg cells (FIG. 19C).

Example 11. Effects of M23L-HLE in Autoimmune Hyperglycemia Mice

This example demonstrates that administration of M23L-HLE resulted in protection of treated mice from an exemplary autoimmune condition, autoimmune hyperglycemia.

At 7 weeks of age, mice were assigned to treatment groups based on non-fasted blood glucose and were dosed according to Table 7 via intraperitoneal (IP) injection of 100 μl/mouse. Body weights, clinical observations, and non-fasted blood glucose were recorded weekly for study duration. Any animals with non-fasted blood glucose >250 mg/dL for two consecutive days were humanely euthanized.

TABLE 7

Mouse Study Dosing Schedule

| Group | N | Test Articles | Dose | Route | Dosing Schedule |
|---|---|---|---|---|---|
| 1 | 16 | PBS | N/A | i.p. | Once weekly for 2 weeks, then every other week up to 20 weeks of age (8 doses total) |
| 2 | 16 | E62A-HLE | 0.1 mg/ml | i.p. | Once weekly for 2 weeks, then every other week up to 20 weeks of age (8 doses total) |
| 3 | 10 | M23L-HLE | 0.1 mg/ml | i.p. | Once weekly for 2 weeks, then every other week up to 20 weeks of age (8 doses total) |
| 4 | 11 | IL-2-HLE | 0.1 mg/ml | i.p. | Once weekly for 2 weeks, then every other week up to 20 weeks of age (8 doses total) |

Figure 20A:
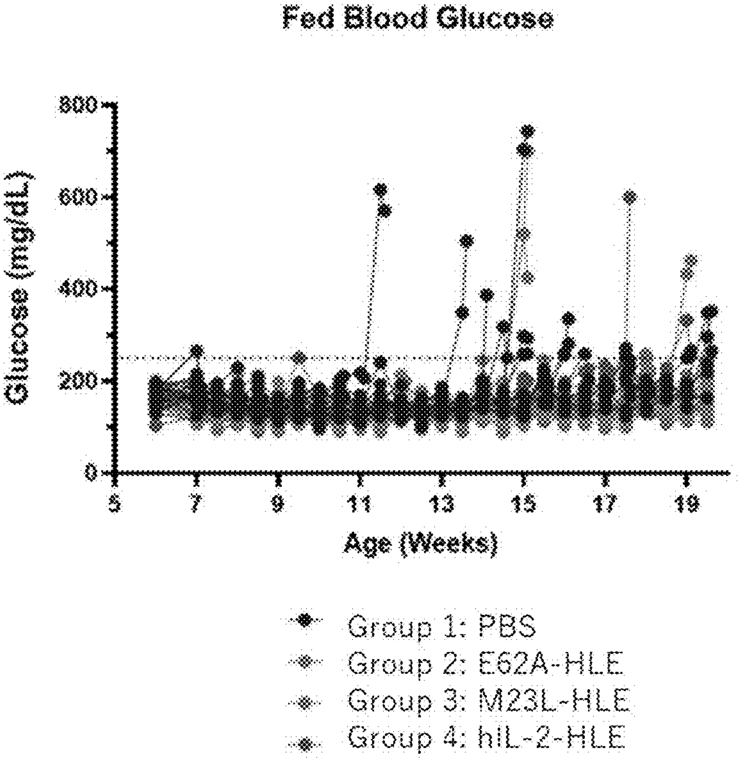
FIG. 20A shows a graph of blood glucose measurement in mice treated with PBS, E62A-HLE and M23L-HLE.
Figure 20B:
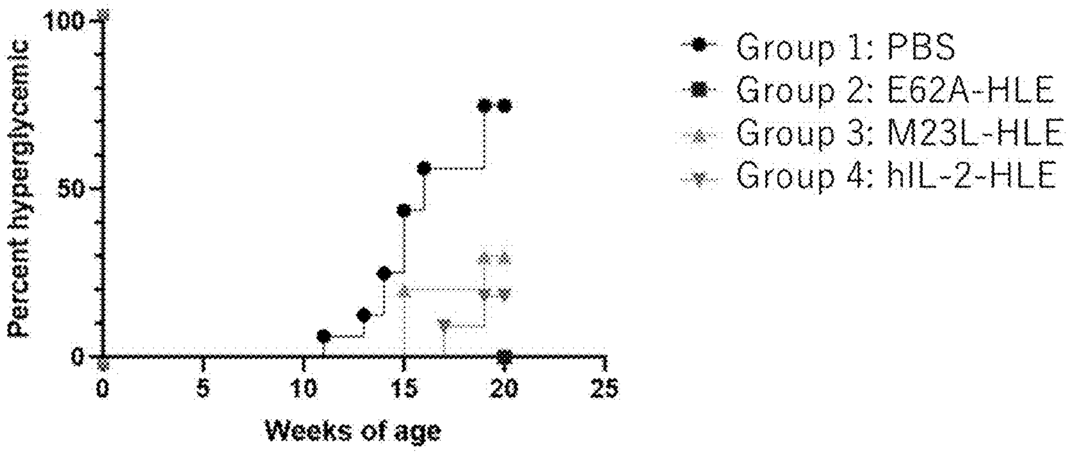
FIG. 20B shows a graph of the percent incidence of hyperglycemia over time in mice treated with E62A-HLE, M23L-HLE and WT hIL-2-HLE.

Blood glucose was measured (FIG. 20A). The results showed that in contrast to PBS treated mice which demonstrated 75% incidence of hyperglycemia by 20 weeks of age (n=16), no mice treated with E62A-HLE developed hyperglycemia by 20 weeks of age (n=16), 30% mice treated with M23L-HLE and 18% mice treated IL-2-HLE developed hyperglycemia suggesting that M23L-HLE protects mice from autoimmune hyperglycemia (FIG. 20B).

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

The invention claimed is:

1. An engineered human interleukin-2 (IL-2) variant comprising amino acid substitutions in the amino acid sequence set forth in SEQ ID NO: 1, wherein the substitutions are selected from a group consisting of:

(1) T111H;

(2) T111H and C125A;

(3) E15T; and (4) E15T and C125A.

2. The engineered human IL-2 variant of claim 1, wherein the substitution is a T111H mutation.

3. The engineered human IL-2 variant of claim 1, wherein the substitution is a E15T mutation.

4. A recombinant IL-2 fusion protein comprising the engineered human IL-2 variant of claim 1 fused to an IgG Fc domain.

5. A recombinant IL-2 fusion protein comprising the engineered human IL-2 variant of claim 1 fused to an anti-CTLA4 antibody.

6. A nucleotide encoding an amino acid sequence of the engineered human IL-2 variant of claim 1 or the recombinant IL-2 fusion protein of claim 4 or 5.

7. A pharmaceutical composition comprising the engineered human IL-2 variant of claim 1 or the recombinant IL-2 fusion protein of claim 4, or a salt thereof.

8. A method of proliferating regulatory T cells (Treg cells) in a subject in need thereof, the method comprising administering to the subject an effective amount of the engineered human interleukin-2 (IL-2) variant of claim 1 or a recombinant IL-2 fusion protein of claim 4.

9. A method for treating autoimmune disease in a subject in need thereof, the method comprising administering to the subject an effective amount of the engineered human interleukin-2 (IL-2) variant of claim 1 or the recombinant IL-2 fusion protein of claim 4.

10. The method of claim 9, wherein the administration increases levels of phosphorylated STAT5 (pSTAT5a) in human peripheral blood cells.

11. The method of claim 9, wherein the administration increases regulatory T cells (Treg cells).

12. The method of claim 9, wherein the autoimmune disease is multiple sclerosis, lupus, ankylosing spondylitis, arthritis, colitis, Type I diabetes, inflammatory disease, or Crohn's disease.

13. The method of claim 9, wherein the autoimmune disease is autoimmune hyperglycemia.

14. A method of proliferating regulatory T cells (Treg cells), comprising contacting a population of T cells with an effective amount of the engineered human interleukin-2 (IL-2) variant of claim 1 or the recombinant IL-2 fusion protein of claim 4.

15. The engineered human IL-2 variant of claim 1, wherein the substitutions are T111H and C125A mutations.

16. The engineered human IL-2 variant of claim 1, wherein the substitutions are E15T and C125A mutations.

17. A pharmaceutical composition comprising the engineered human IL-2 variant of claim 1 or the recombinant IL-2 fusion protein of claim 5, or a salt thereof.

18. A method of proliferating regulatory T cells (Treg cells) in a subject in need thereof, the method comprising administering to the subject an effective amount of the engineered human interleukin-2 (IL-2) variant of claim 1 or a recombinant IL-2 fusion protein of claim 5.

19. A method for treating autoimmune disease in a subject in need thereof, the method comprising administering to the subject an effective amount of the engineered human interleukin-2 (IL-2) variant of claim 1 or the recombinant IL-2 fusion protein of claim 5.

20. A method of proliferating regulatory T cells (Treg cells), comprising contacting a population of T cells with an effective amount of the engineered human interleukin-2 (IL-2) variant of claim 1 or the recombinant IL-2 fusion protein of claim 5.

* * * * *